(12) United States Patent
Martin et al.

(10) Patent No.: US 6,197,065 B1
(45) Date of Patent: Mar. 6, 2001

(54) METHOD AND APPARATUS FOR SEGMENTAL BONE REPLACEMENT

(75) Inventors: Daniel L. Martin, Palo Alto, CA (US); John Robert White, Winona Lake, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/003,061

(22) Filed: Jan. 5, 1998

Related U.S. Application Data

(63) Continuation-in-part of application No. 08/535,532, filed on Sep. 28, 1995, now abandoned, which is a continuation-in-part of application No. 08/146,510, filed on Nov. 1, 1993, now abandoned.

(51) Int. Cl.[7] .................................................... A61F 2/36
(52) U.S. Cl. ............................................... 623/23.17
(58) Field of Search ...................................... 623/18–23

(56) References Cited

U.S. PATENT DOCUMENTS

| | | |
|---|---|---|
| 2,397,545 | 4/1946 | Hardinge . |
| 3,947,897 | 4/1976 | Owens . |
| 4,016,874 | 4/1977 | Maffei et al. . |
| 4,080,666 | 3/1978 | Fixel . |
| 4,129,903 | 12/1978 | Huggler . |
| 4,158,895 | 6/1979 | Reswick et al. . |
| 4,314,381 | 2/1982 | Koeneman . |
| 4,502,160 | 3/1985 | Moore et al. . |
| 4,586,932 | 5/1986 | Scales . |
| 4,644,943 | 2/1987 | Thompson et al. . |
| 4,673,407 | 6/1987 | Martin . |
| 4,904,264 | 2/1990 | Scheunemann . |
| 4,938,768 | 7/1990 | Wu . |
| 4,946,459 | 8/1990 | Bradshaw et al. . |

(List continued on next page.)

FOREIGN PATENT DOCUMENTS

| | | |
|---|---|---|
| 3605630 | 9/1987 | (DE) . |
| 293485 | 9/1991 | (DE) . |
| 2519248 | 12/1981 | (FR) . |
| 1181652 | 9/1985 | (SU) . |

OTHER PUBLICATIONS

D.L. Martin, M.D., A.S. Turner, B.V.Sc., M.S., J.O. Johnston, M.D., Comparison of Cortical Bone Loss is Segmental Bone Prosthetic Replacement: Cemented Stem vs. Compliant Fixation.

*Primary Examiner*—Bruce Snow
(74) *Attorney, Agent, or Firm*—Harness, Dickey & Pierce, P.L.C.

(57) ABSTRACT

A bone attachment assembly for a remaining portion of a long bone diaphysis following resection is provided. The assembly includes a main body, an anchor for anchoring the device with respect to the remaining bone portion and an attachment portion for attaching the main body to the anchor. The assembly may be connected to an orthopedic appliance, an interposed orthopedic appliance connected to a second bone attachment assembly, or a transcutaneous bar for attaching an external appliance. A reaming device for creating an intramedullary cavity, a guide device for guiding an aperture-forming procedure in a remaining bone portion, and a milling device for shaping an interface surface of the bone in a preselected geometry are also provided. In the method of the present invention, a cavity is created within a remaining bone portion using the reaming device. At least one aperture is created using the guide device, and the bone surface is milled to a preselected geometry using the milling device. The above components are then assembled together within the cavity to form the device of the present invention. The device may then be connected to other devices as stated above. A bone attachment assembly may also be provided having a compliant section integrally disposed that is operable for being converted to a preselected condition of expansion prior to or following implantation.

10 Claims, 17 Drawing Sheets

U.S. PATENT DOCUMENTS

| | | |
|---|---|---|
| 4,947,502 | 8/1990 | Engelhardt . |
| 4,955,910 | 9/1990 | Bolesky . |
| 4,959,064 | 9/1990 | Engelhardt . |
| 4,986,834 | 1/1991 | Smith et al. . |
| 5,007,935 | 4/1991 | Vincent et al. . |
| 5,035,712 | 7/1991 | Hoffman . |
| 5,057,103 | 10/1991 | Davis . |
| 5,071,435 | 12/1991 | Fuchs et al. . |
| 5,108,398 | 4/1992 | McQueen et al. . |
| 5,133,760 | 7/1992 | Petersen et al. . |
| 5,180,383 | 1/1993 | Haydon . |
| 5,181,928 | 1/1993 | Bolesky et al. . |
| 5,197,989 | 3/1993 | Hinckfuss et al. . |
| 5,201,881 | 4/1993 | Evans . |
| 5,281,226 | 1/1994 | Davydov et al. . |
| 5,326,360 | 7/1994 | Kotz et al. . |
| 5,334,184 | 8/1994 | Bimman . |
| 5,352,227 | 10/1994 | O'Hara . |
| 5,358,524 | 10/1994 | Richelsoph . |
| 5,389,107 | 2/1995 | Nassar et al. . |
| 5,411,504 | 5/1995 | Vilas . |
| 5,800,553 | 9/1998 | Albrektsson et al. . |

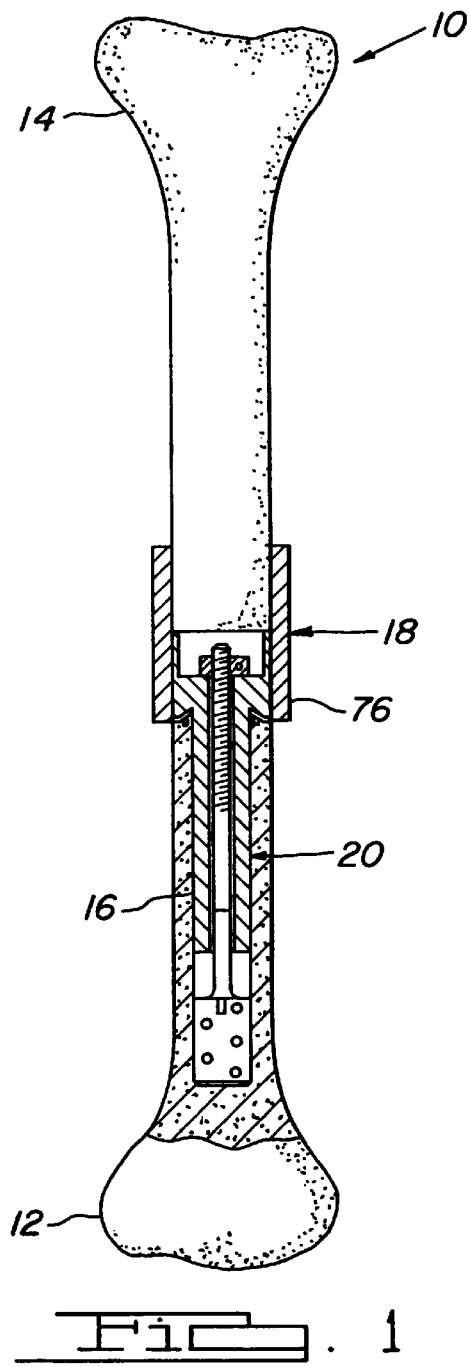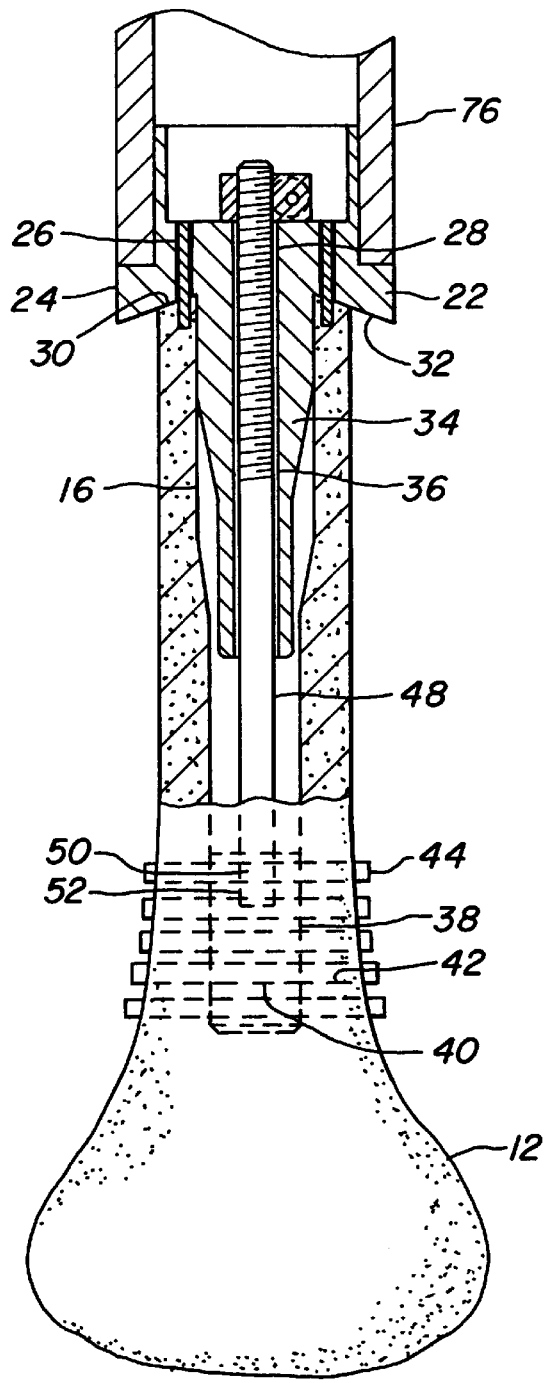

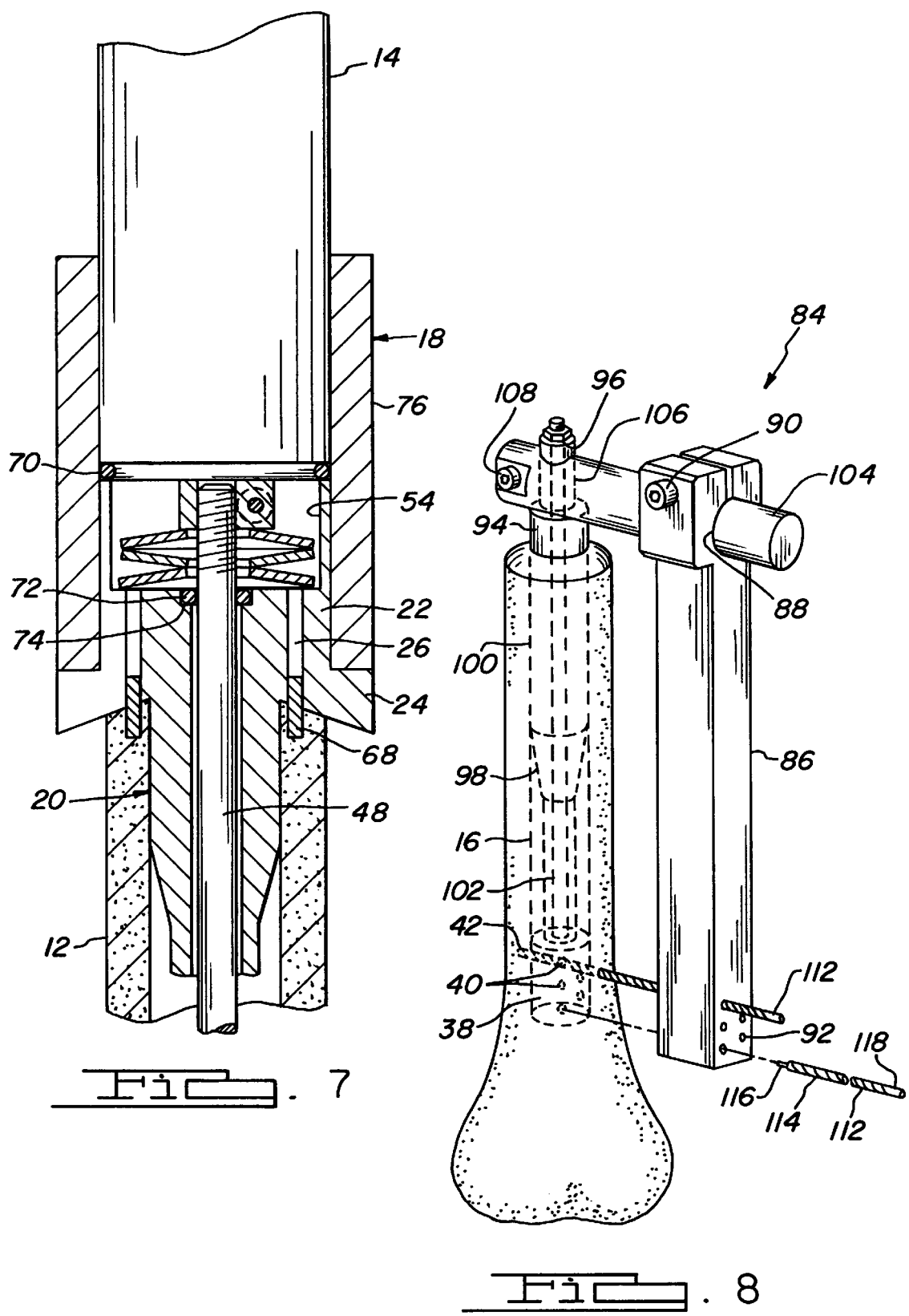

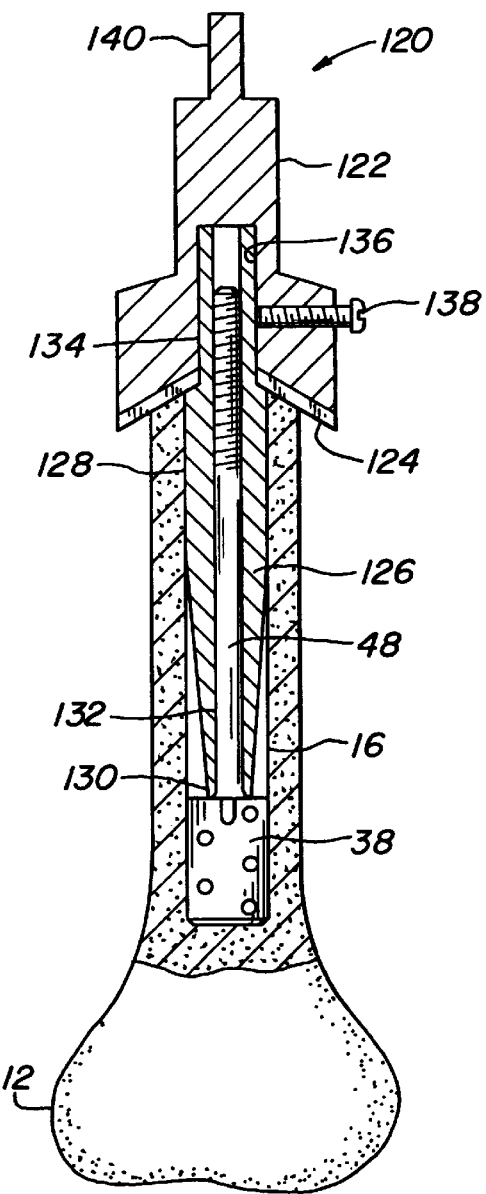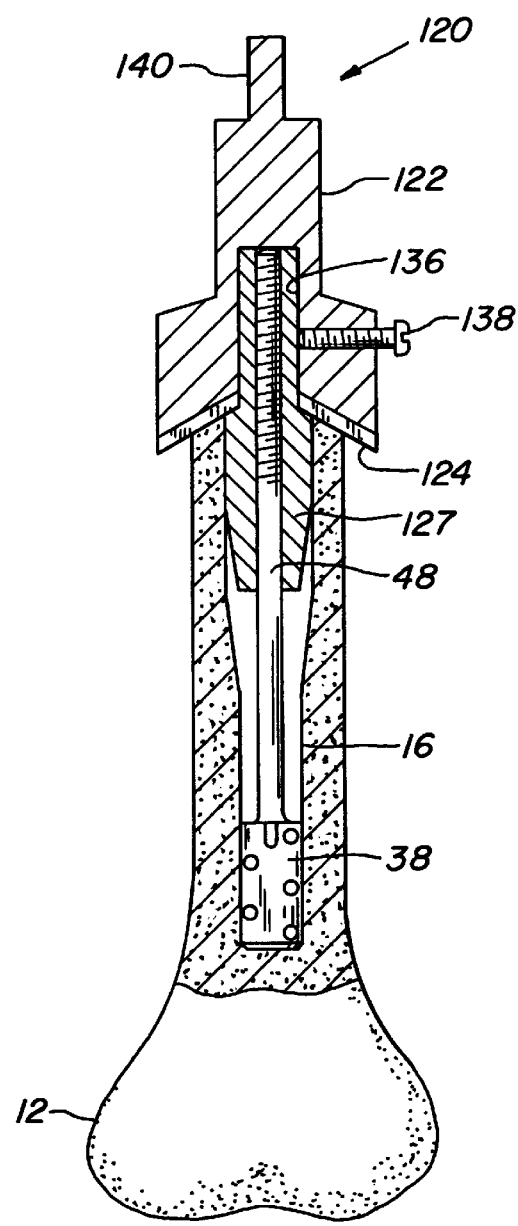

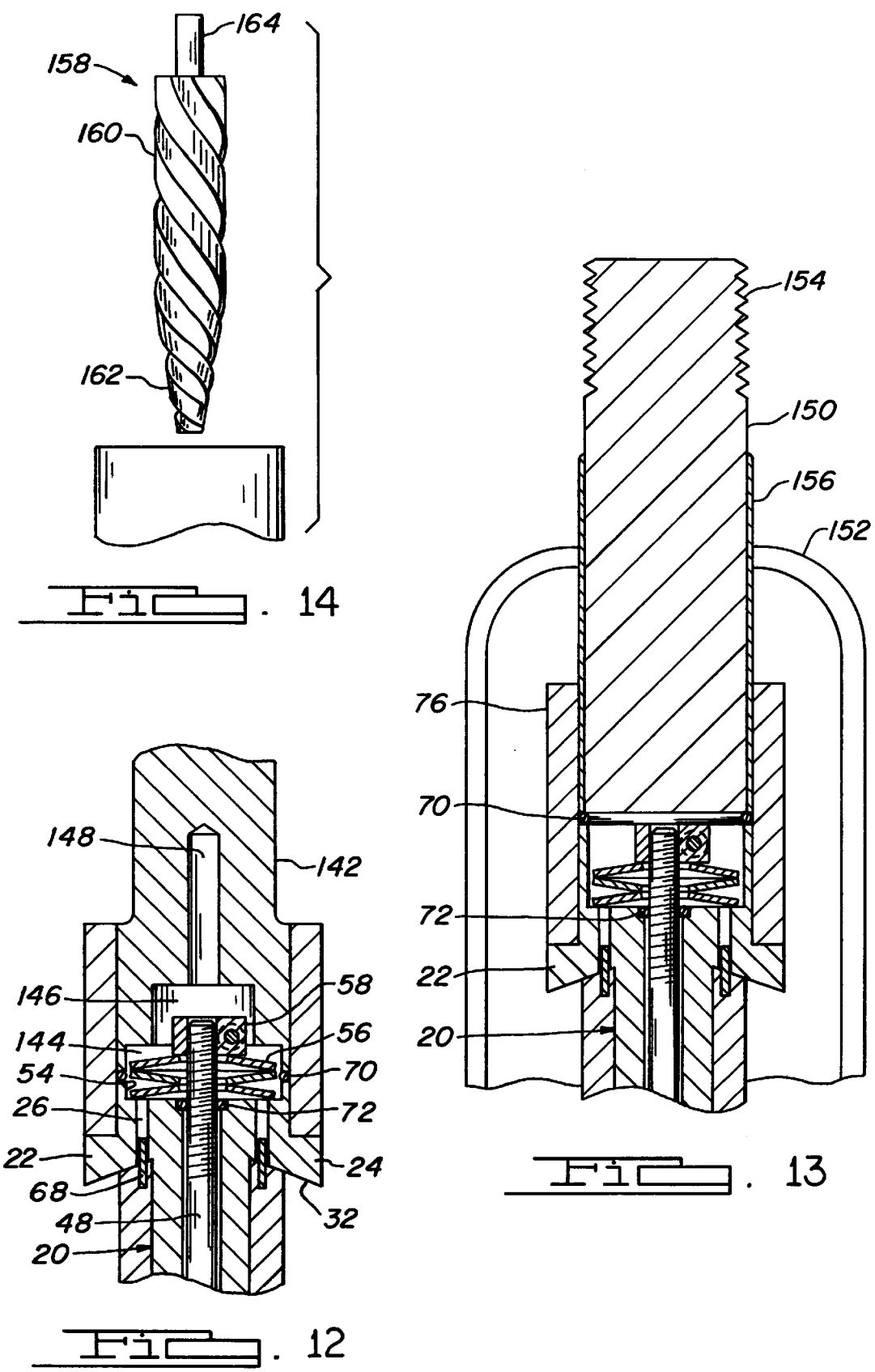

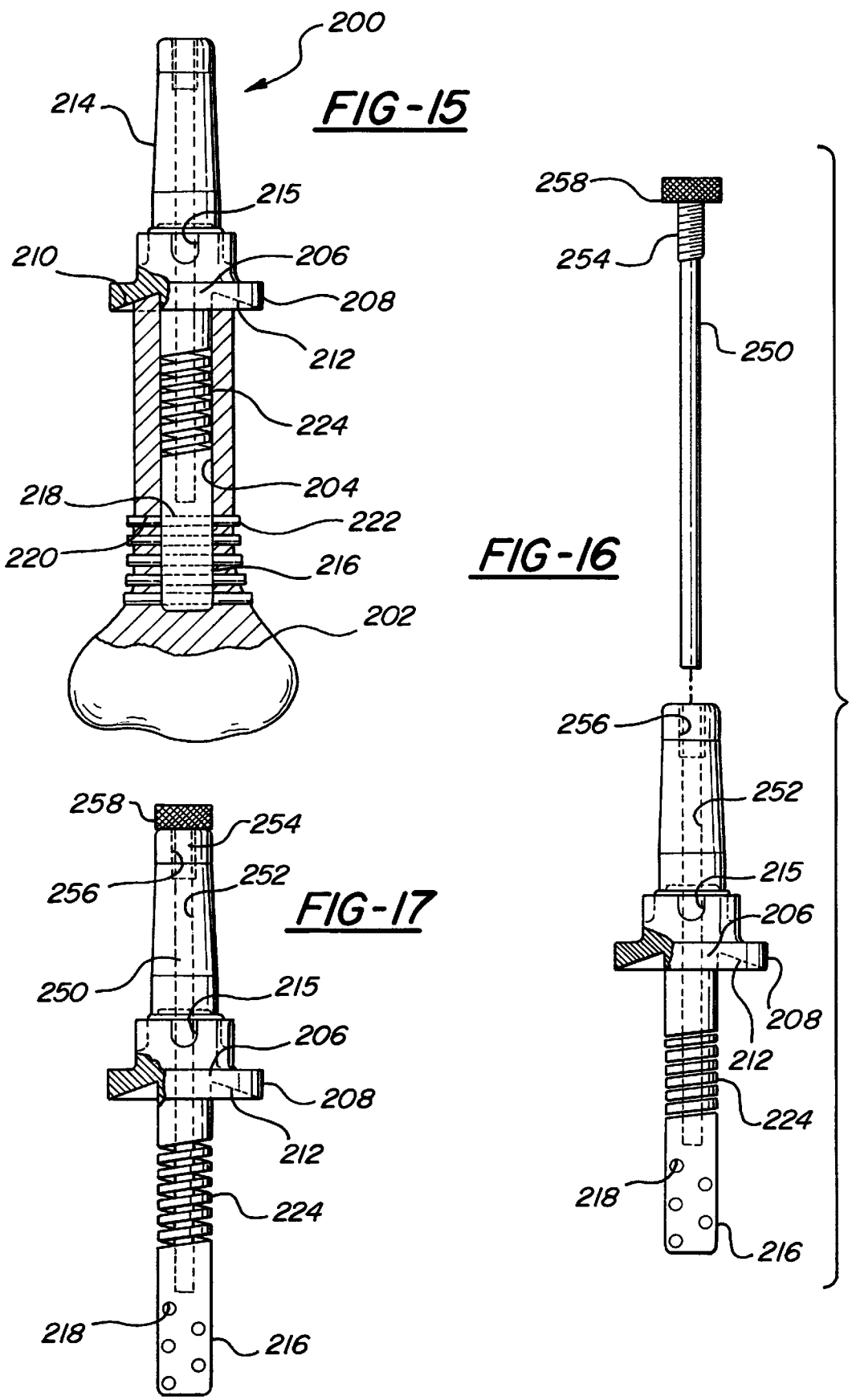

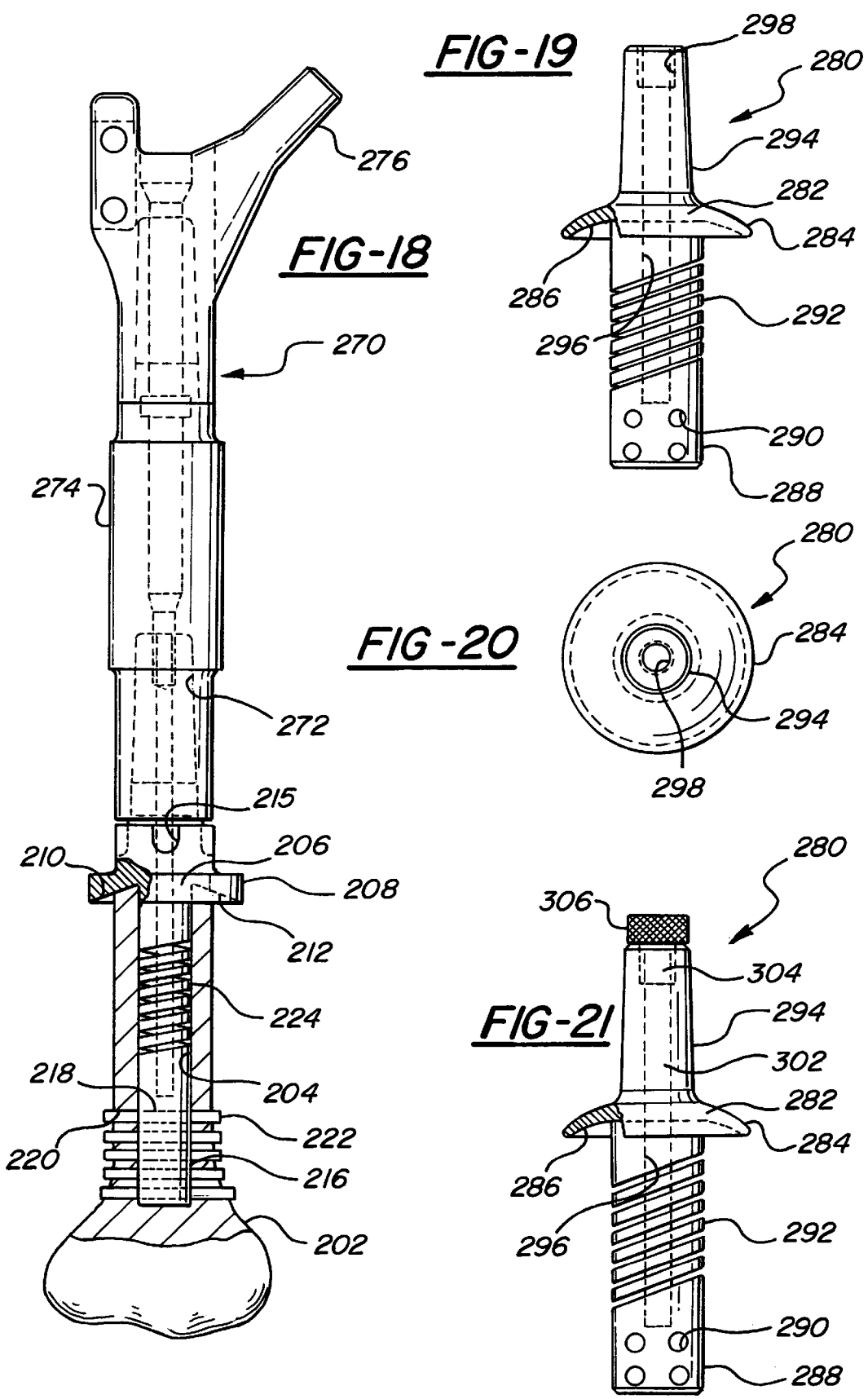

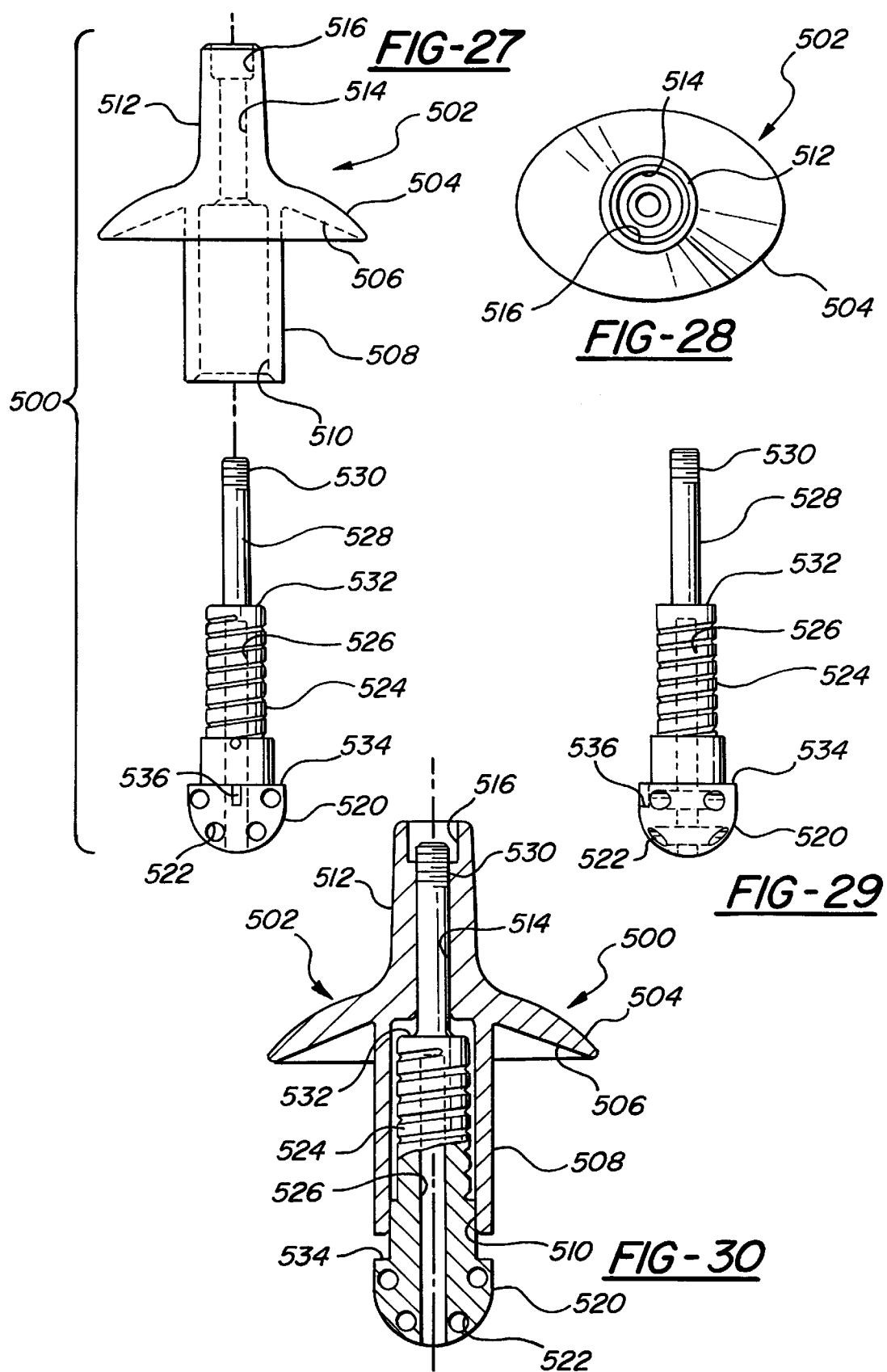

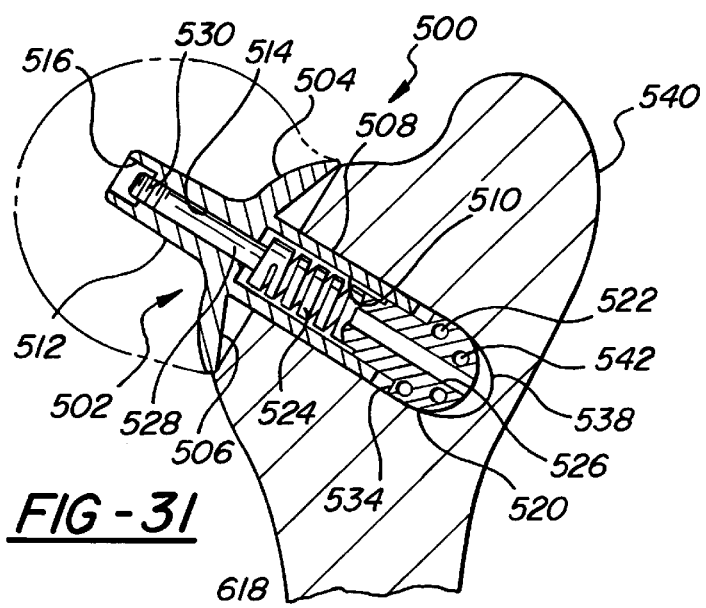
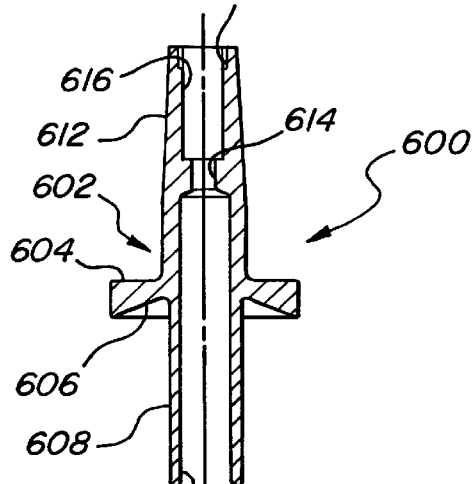
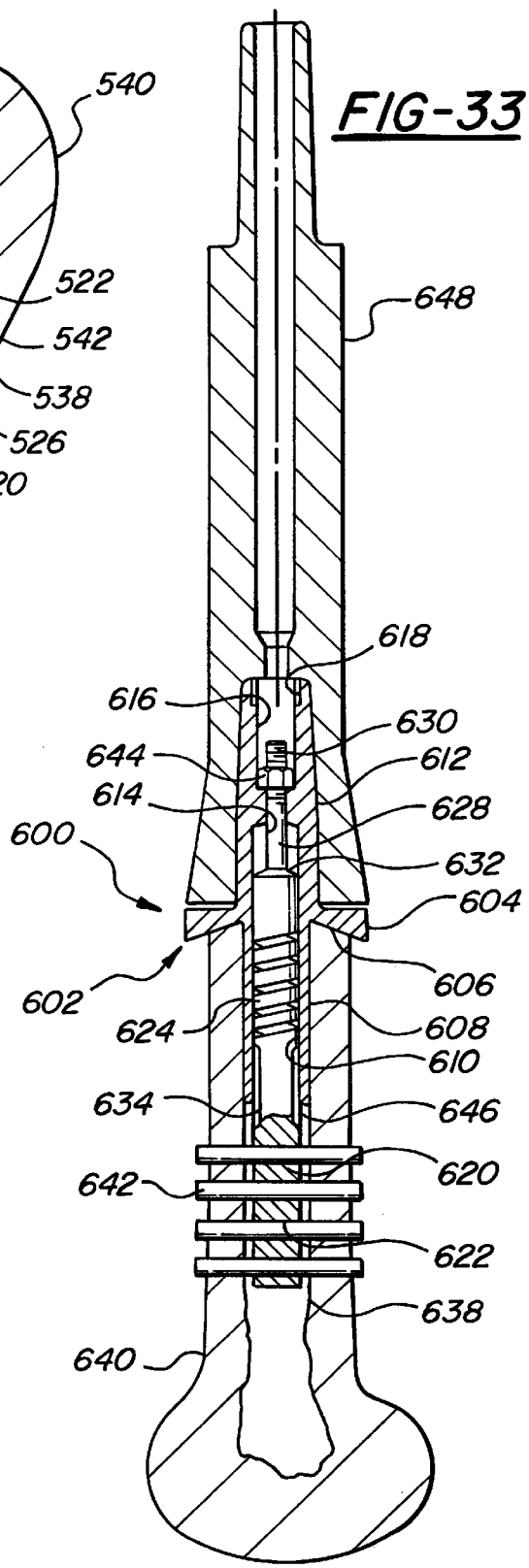

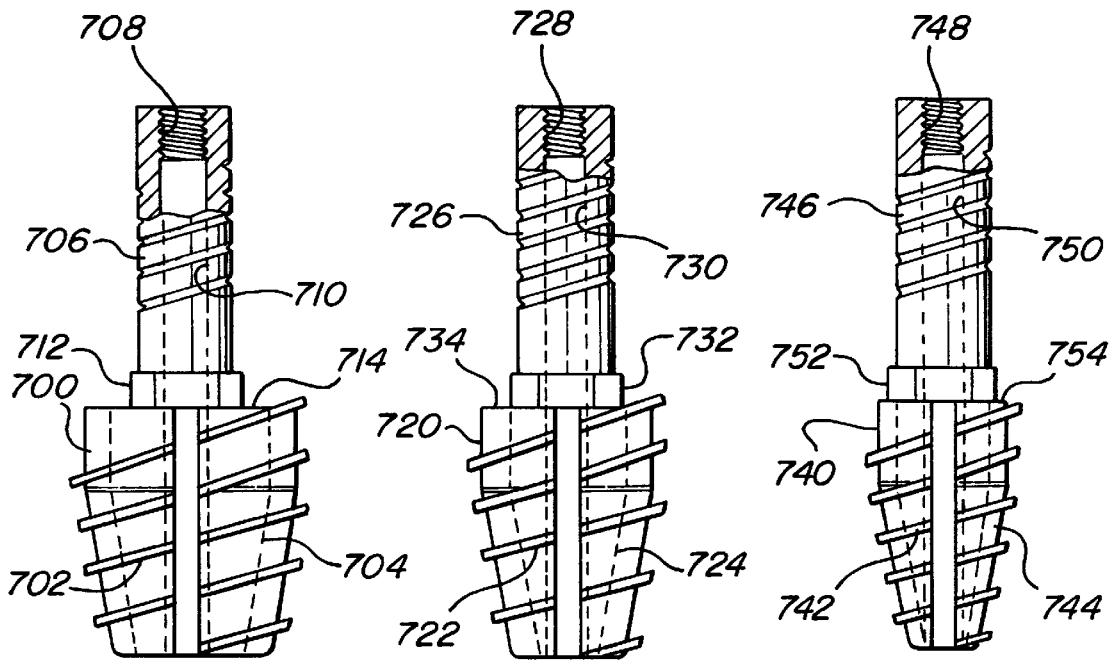
*FIG-34*   *FIG-35*   *FIG-36*
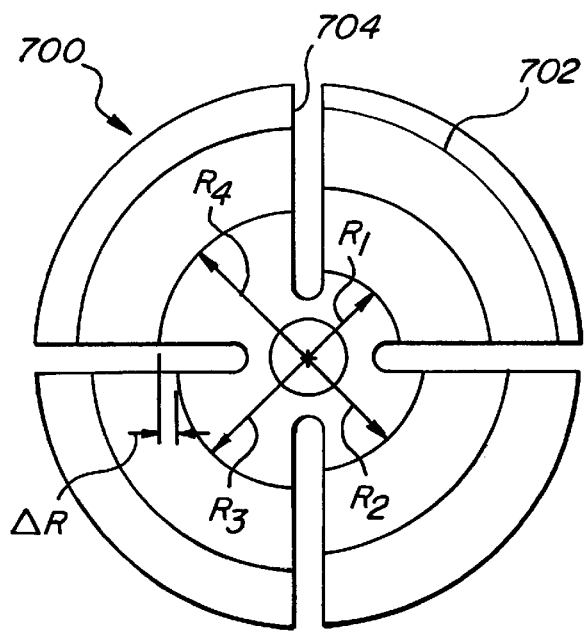
*FIG-37*
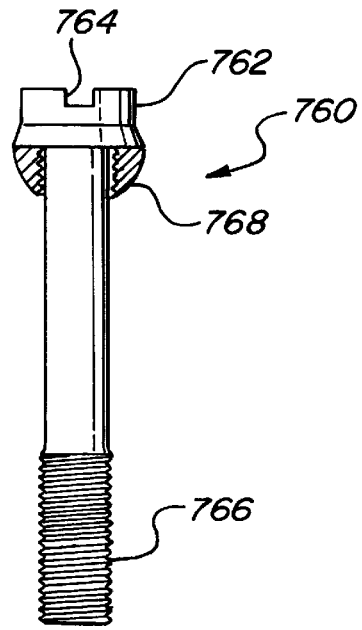
*FIG-38*

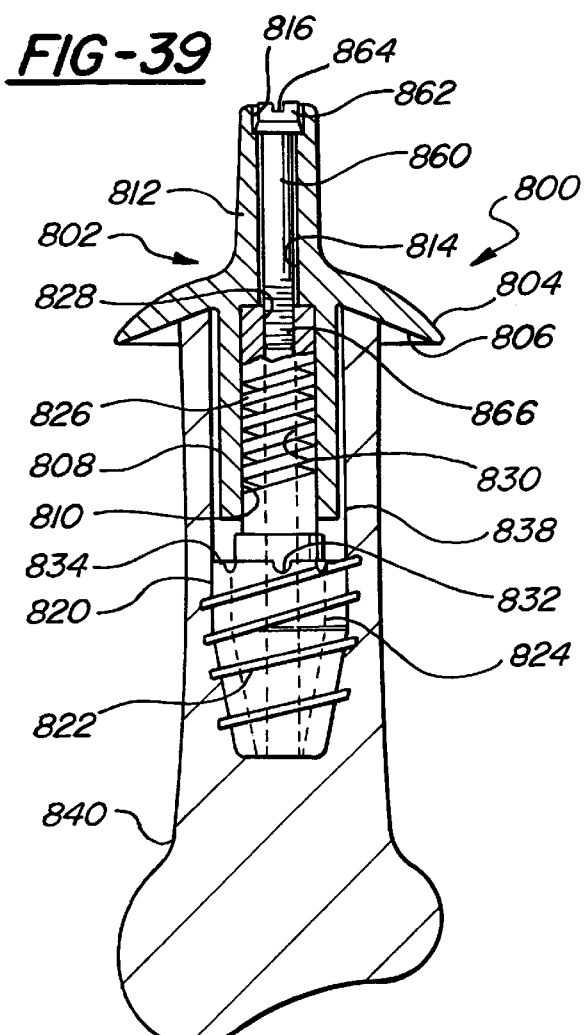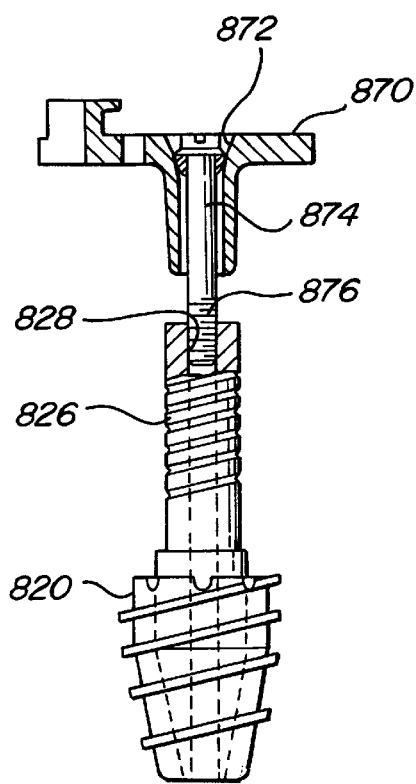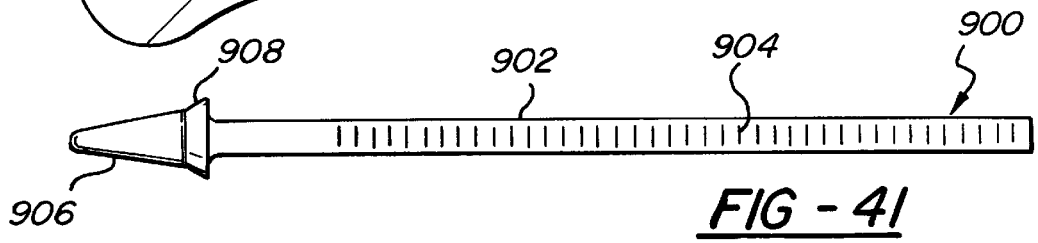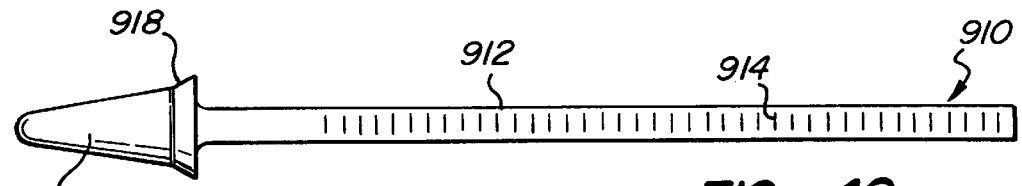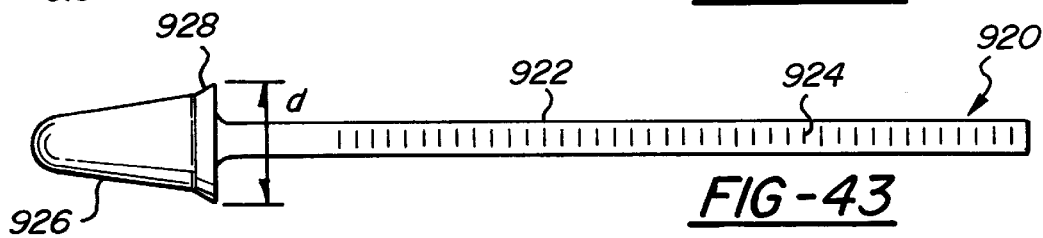

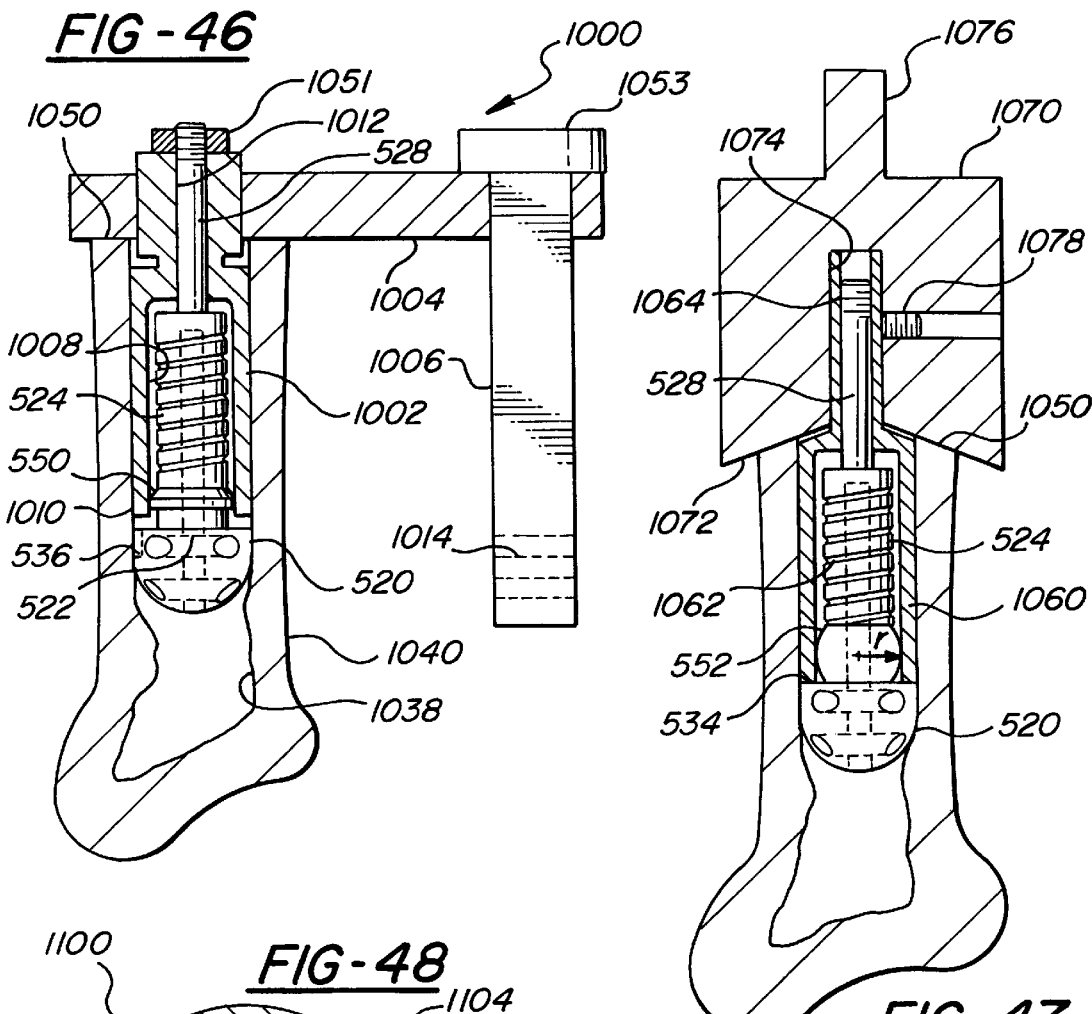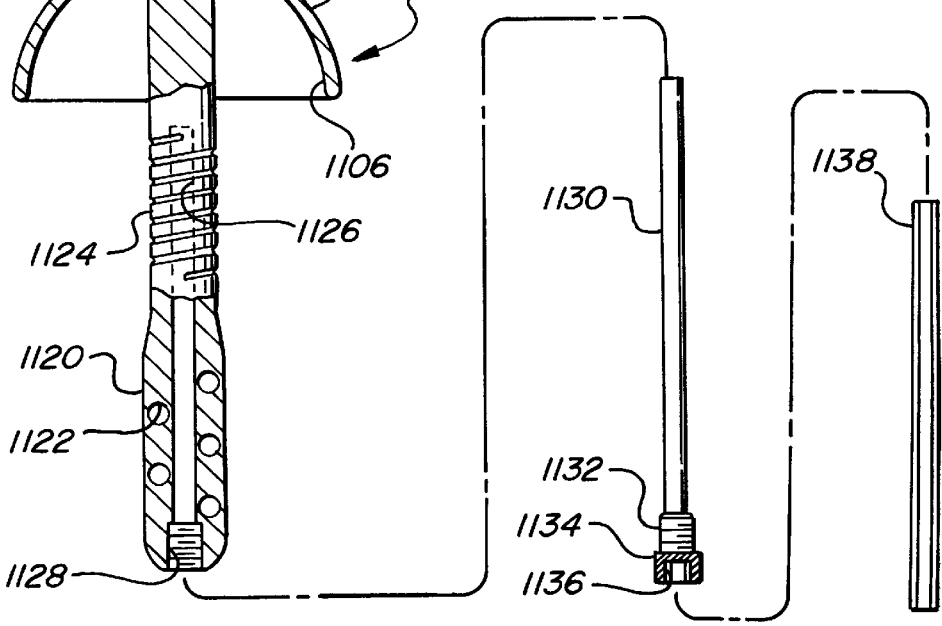

METHOD AND APPARATUS FOR SEGMENTAL BONE REPLACEMENT

CROSS REFERENCE TO RELATED APPLICATIONS

This application is a continuation-in-part of U.S. application Ser. No. 08/535,532, filed Sep. 28, 1995, now abandoned which is a continuation-in-part of U.S. application Ser. No. 08/146,510, filed Nov. 1, 1993, now abandoned.

BACKGROUND OF THE INVENTION

1. Field of the Invention

This invention relates to a bone-replacement prosthetic device, and in particular, to a method and apparatus for segmental bone replacement.

2. Description of the Related Art

In prosthetic segmental bone replacements, it is sometimes necessary to replace a portion of a long bone to correct various types of bone injury such as those caused by bone tumors, osteoarthritis, fracture dislocations, rheumatic arthritis, and aseptic or avascular bone necrosis. In these types of surgical procedures, it is necessary to resect a mid and/or end portion of a long bone and secure the remaining portion of bone through the use of some type of intramedullary device. This is accomplished by the use of one metal stem, or in certain cases, two opposing metal stems, secured in the medullary region by a "bone cement" or a grout material, such as methylmethacrylate.

Biologic fixation of intramedullary devices at the mid-diaphyseal level has not been entirely satisfactory, particularly in active younger patients, where it is important to form a stable, long-lasting prosthetic attachment. In time, the lack of adequate stress transfer from the metal stem to the surrounding bone causes a loss of bone density, resulting in increased possibility of bone failure or loosening of the bone-stem interface. Also, the bone reacts in the grout material or smooth metal stem by forming a soft-tissue lining around the cement, and this lining additionally mediates load transfer from the prosthetic device to the bone. The soft-tissue lining that forms about the device tends to loosen over time, particularly with continued shear loads, i.e., loads applied substantially in the direction of the axially extending bone/stem interface, and the loosening may become great enough in time to require surgical revision. Also, the relatively low tolerance of force transfer per unit area of interface requires a large bone/stem interface, which, in younger patients, may exceed the available interface area.

In replacement surgeries, which begin at the mid-diaphyseal level, the enlarged intramedullary cavities created within a remaining diaphyseal bone portion for the insertion and rigid fixation of a metal intramedullary device stem is also of small diameter. As a result, the device stems must be of a small diameter to fit within the diaphysis, with resulting poor rotational control. Also, high bending moments in thin stems at the mid-diaphysis risk fatigue failure, making a stable interface between the stem and the surrounding bone surface even more difficult to achieve.

Although the use of a tapered stem is one way to achieve increased security of the stem within the medullary canal, the canal dimensions tend to increase rather than decrease with increasing depth into the canal, thereby preventing secure wedging of a tapered stem. Consequently, "bone cement" or grout fixation is often used to secure the stem within the medullary canal. This technique, however, prevents stress transfer through the bone to the level of the osteotomy, therefore resulting in osteopenia adjacent to the stem. The same effect prevents bony ingrowth into porous pads on the shoulders of the implants. A limitation of prosthetic devices which rely on biological fixation, particularly fixation to an elongate stem within the intramedullary region of a bone, is the problem of stress protection of the bone region between the area of force application to the prosthesis and the area of load transfer to the bone. Stress protection is due to the rigid attachment between the prosthetic device and bone which occurs in biological fixation and to the relatively high elastic modulus of the implant material, which typically is five to fifteen times greater than that of the surrounding bone. These two factors combine to transfer a stress from the area of stress loading on the implant through the more rigid implant, rather than through the surrounding bone tissue. For example, in a hip-joint prosthesis biologically anchored to the bone by an entire elongate stem, axial stress on the upper joint is transferred largely through the stem to the bone connection farthest from the joint, rather than through the intermediate bone region surrounding the part of the stem closest to the joint. As a result, the intermediate bone region tends to be resorbed over time due to lack of deformation stressing. The gradual loss of bone support in the region of the stem increases the bending load that must be borne by the stem, and this can lead to implant fatigue and failure.

The problem of maintaining a motionless bone-prosthesis interface during the post-operative period when bony attachment is occurring may be partially solved by surgically fastening the prosthetic device to the bone structure by screws or the like. This method has been proposed for use in fastening a knee-joint prosthesis to a surgically formed, substantially planar surface of the bone. Typically, the prosthesis is attached by two or more screws, each tightened to hold the prosthesis against the bone surface with a selected compression. However, since the bone quickly accommodates to the applied force of the screws, by viscoelastic creep, the compression, and thus the resistance to the implant movement relative to the bone, is quickly lost. If interface movement does occur from a single episode of overloading, then any residual compression is permanently lost. More movements result in build-up of fibrous tissue, preempting biological bone fixation to the implant. Only with unphysiologic post-operative protection of the joint, resulting in joint stiffness and muscle wasting, and with demanding operative technique, can risk of loosening be reduced. The device also suffers from problems of stress protection and non-physiological load transfer, inasmuch as loading force applied to the prosthesis is transferred directly through the screws, rather than through the region of bone through which the screws extend. This can lead to loss of bone integrity in the stress protected area.

The problems associated with anchorage via soft tissue along a prosthesis stem have been overcome partially by using a prosthesis whose stem surface allows direct attachment without an interposed soft tissue layer. Such surfaces include micropore surfaces that allow attachment via ingrowth and/or attachment of bone, and ceramic surfaces that allow actual bonding of bone. Following surgical implantation of the stem, the surrounding bone tissue gradually forms a biological fixation matrix with the stem surface by tissue growth into or onto the surface. Because of the stronger interface between the bone and the stem, which allows a relatively large force per unit area without loosening, problems of late loosening and detachment are largely avoided and the force transfer area can be made smaller.

A limitation of the biological-fixation bonding approach, however, is the need to keep the prosthesis mechanically fixed with respect to the bone over a 2–3 month post-operative period, during which the biological fixation is occurring. If relative movement between the implant stem and bone is allowed to occur before biological fixation is complete, a fibrous tissue layer which acts to prevent good biological fixation develops at the interface and eventual progression to gross loosening is likely.

Another shortcoming resulting from bone replacement surgeries, particularly joint replacement procedures, is a phenomenon known as wear particle bone lysis. The replacement of a joint, including the installation of a polyethylene or similar high molecular weight synthetic wear surface, results over time in particles becoming dislodged from the wear surface due to friction between the joint sections during movement. These wear particles tend to move with fluid transfer along the interface between the prosthesis and the surrounding soft tissue, and also tend to enter the intramedullary space between the prosthesis stem and the surrounding remaining bone portion. The biological reaction to these small wear particles causes the surrounding bone tissue to be lysed, thereby weakening the bone and potentially causing subsequent bone failure. Thus, a means for sealing the intramedullary space from the exterior space could largely reduce this difficulty.

Prosthetic devices having spring-loaded mechanisms for holding a joint-replacement prosthesis against a planar surface of the bone, to immobilize the prosthesis on the bone, have been proposed, e.g., in the related field of joint replacements, such as in U.S. Pat. No. 4,129,903. Devices of this type solve some of the above-noted problems associated with prosthesis attachment to the bone, in that the prosthesis is held against the bone under relatively constant tension in the post-operative period, with or without provision for biological fixation. Nonetheless, limited movement may occur when the major loading stresses (in the principal direction of weight transfer on the joint) are not normal to the plane of the interface between the bone and prosthetic device and it is necessary to rely on a grouting compound to prevent shear motions. Further, such devices use a rigid stem or shaft for anchoring the implant to the bone traversed by the stem from physiologic shear, rocking, and/or axial rotation stresses.

Each of these potential problems may limit physical activity and long-term durability prognosis for long segmental replacement arthroplasty patients. Thus, current methods may potentially result in repeat surgeries which leave less bone stock and may eventually require amputation or other undesirable salvage procedures.

For the above reasons, it is desirable to provide a segmental bone replacement device which enhances a stable biologic fixation, yet allows for physiologic cyclic load transfer to the device-bone interface. It is also desirable to provide a device which promotes osteogenesis into those surfaces adjacent to the osteotomy.

SUMMARY OF THE INVENTION

The present invention provides a biocompatible bone attachment assembly which is a connector or segment replacing a section of a long bone diaphysis, such as the remaining portion of a resected femur. The assembly includes at least a biocompatible bone attachment device which is secured to a first remaining bone portion and may be connected to an opposing orthopedic appliance or a transcutaneous bar. The attachment device and the orthopedic appliance or transcutaneous bar may be secured in an adjacent relation by a suitable securing means.

Compliant fixation is a significant advance in this field because it provides compliance of fixation force which maintains compression of the implanted device at the device-bone interface while allowing axial compression or elongation of the remaining bone portion. In addition, compliant fixation provides excursion in that it allows compensation for loosening of the implant device following installation to accommodate settling of the implant device against the bone. In the use of compliant fixation devices, the implant is constructed to be more compliant than the surrounding bone, that is, the spring constant of the implant is by design less than the spring constant of the bone with regard to any or all of bending, torsion and axial compression.

A bone attachment device of the present invention includes a main body having an interface surface for abutting against an interface surface of a remaining bone portion. The device further includes means for anchoring the bone attachment device within an enlarged cylindrical intramedullary cavity of the remaining bone portion. This is preferably provided as an anchor body which is secured within the enlarged intramedullary cavity through one or more transverse pins or interlocking screws which engage both the anchor body and the surrounding bone.

The bone attachment device further includes compliant means for attaching the main body to the means for anchoring the bone attachment device. This preferably includes a compliant connecting rod which extends from the anchor body through the osteotomy surface.

The means for attaching the main body to the means for anchoring the bone attachment device may also include a supplemental means for biasing the connecting rod against the main body. This is preferably provided as a supplemental interposed compliant device disposed in communication with both the connecting rod and the main body, which is most preferably one or more washer springs secured upon the connecting rod against a surface or recess of the main body by a retaining means.

The device may further include one or more means for enhancing a fluid seal of the intramedullary cavity from the external environment, which may be provided as one or more o-rings or similar sealing members disposed at one or more suitable locations upon or within the main body.

The present invention may further include a reaming device for creating an enlarged cylindrical intramedullary cavity within the first remaining bone portion. The reaming device is operated by connection to a drilling device, such as a hand drill.

The present invention may further include a guide device for guiding an aperture-forming procedure upon the remaining bone portion. The guide device is operable to be assembled onto a protruding portion of an integrated connecting rod and anchor body above the osteotomy surface.

The present invention may further include a milling device for shaping the osteotomy surface in a preselected geometry. The milling device is also operated by connection to a hand drill.

In the method of the present invention, a bone is resected to yield at least a first remaining bone portion. A cylindrical intramedullary cavity is then created to a reselected depth, through the use of a reaming device as described herein, which cavity is suitable for receiving the bone attachment device of the present invention.

Means for anchoring the bone attachment device, such as an anchor body, or an integrated connecting rod and anchor body, followed by means for attaching the main body to the means for anchoring the bone attachment device, such as a connecting rod, is inserted into the cavity. A guide device, as described herein, is attached to the inserted connecting rod at its protrusion from the osteotomy surface, and is adjusted to guide an aperture-forming procedure upon the first remaining bone portion. Thereafter, the anchor body is engaged against the surrounding bone by the insertion of one or more engagement devices, such as transverse pins or interlocking screws, through the apertures previously created with the assistance of the guide device. The osteotomy surface of the first remaining bone portion is milled in a preselected geometry for promoting bone ingrowth, through the use of a milling device as described herein. The main body is then slipped into position on the end of the bone. Anti-rotation pins are drilled and inserted. One or more supplemental interposed compliant devices, which is preferably one or more washer springs, may then be positioned upon the connecting rod, and enhanced in a secured relation upon the connecting rod through the use of one or more devices, such as a nut and a lock nut. One or more fluid seal means may also be positioned upon the opening between the connecting rod and the main body, within a recess of the main body, or upon the exterior of the main body.

The above steps may be repeated with respect to an opposing remaining portion of the bone, for connection to the bone attachment device through an interposed orthopedic appliance. A means for enhancing a secured relation, such as a sleeve clamp, may then be positioned about the main body and an opposing member which is an opposing orthopedic appliance or a transcutaneous bar.

The present invention also provides a bone attachment assembly which may be a connector or segment replacing a section of bone, such as a long bone diaphysis or a proximal femur, or may also be a primary bone replacement or a knee or other joint replacement. The assembly includes a main body having an interface surface for abutting against an abutment surface of a first remaining bone portion. The assembly also includes means for anchoring the bone attachment assembly in a substantially stationary position within a cavity located within the first remaining bone portion. This cavity may be a natural intramedullary canal, an enlarged intramedullary canal or a cavity created through the bone at any suitable location. The assembly further includes a compliant section that is preferably integrally formed between the main body and the means for anchoring the bone attachment assembly. The compliant section is operable for being converted to a preselected condition of expansion. The present invention also includes a method for implanting the bone attachment assembly.

The present invention also provides a sleeve disposed upon a compliant section of bone attachment assembly. This sleeve is operable for inhibiting deflection of the compliant section in a non-axial direction during expansion or contraction of the compliant section associated with physiologic loading. The sleeve may preferably be integrally formed with the main body of the device. The present invention also discloses different configurations for the main body and an anchor body that is connected to the main body. Specifically, the anchor body may be secured across the surrounding bone cortex through pins or screws or may alternately include a cylindrical or tapered, self-tapping threaded section for being threaded directly into the bone. The present invention also discloses a compliant section that is integrally formed with the anchor body. Connection of the anchor body and compliant section to another component such as a tibial tray is also contemplated. The compliant section is expanded by force exerted by the anchor body in a direction away from the main body and force applied against the main body in an opposite direction by various traction-applying means, such as a rod integrally formed with the compliant section or threadably secured to the compliant section, and secured with respect to the main body. In addition, instruments are shown and described in accordance with the method of the present invention which involves reaming an intramedullary cavity of a remaining bone portion to an enlarged condition, parallel cross-pinning or threadably securing an anchor body and compliant section within the cavity, positioning the main body upon the anchor body and applying traction through various means to the compliant section.

Accordingly, it is a general object of the present invention to provide a method and apparatus for segmental bone replacement, for primary bone replacement or for a knee or other joint replacement. A related object of the present invention is to provide a method and apparatus for such bone replacement which enhances a biological and mechanical attachment of a bone attachment assembly to a remaining bone portion.

A further object of the present invention is to provide a method and apparatus for segmental bone replacement which allows for physiologic cyclic load transfer to the apparatus-bone interface.

An additional object of the present invention is to provide a method and apparatus for segmental bone replacement which promotes osteogenesis into those surfaces adjacent to the osteotomy.

A further object of the present invention is to provide a method and apparatus for reducing access of wear particles from joint replacements from entering the intramedullary space of a bone following resection.

An additional object of the present invention is to reduce resorption of bone adjacent to an installed bone attachment device.

An additional object of the present invention is to introduce a precision complex technique in such a way that it can be adapted to routine surgical practice.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent from the following specification and appended claims by reference to the following drawings in which:

FIG. 1 is a partial cut-away view illustrating the environment of the device of the present invention in connection with a remaining bone portion following resection;

FIG. 2 is an enlarged cross-sectional view illustrating a bone attachment device as it is secured within a remaining bone portion following resection;

FIG. 7 is a cross-sectional view illustrating a bone attachment assembly of the present invention which includes fluid sealing means for reducing access of wear particles;

FIG. 8 is a perspective view illustrating a guide device for creating one or more apertures within a remaining bone portion for accepting one or more engagement means;

FIG. 9 is a side view illustrating a self-centering drill bit of the present invention;

FIG. 10 is a partial cut-away view illustrating a milling device used for milling the osteotomy surface in a preselected geometry;

FIG. 11 is a partial cut-away view illustrating a milling device used for milling the osteotomy surface in a preselected geometry;

FIG. 12 is a cross-sectional view illustrating a bone attachment device in conjunction with an orthopedic appliance;

FIG. 13 is a cross-sectional view illustrating a transcutaneous bar connected to a device of the present invention;

FIG. 14 is a perspective view illustrating a reaming device of the present invention;

FIG. 15 is an elevational view with partial breakaway illustrating the environment of a second embodiment of the bone attachment assembly of the present invention in an implanted condition in connection with a remaining bone portion following resection;

FIG. 16 is an elevational view with partial breakaway illustrating a second embodiment of bone attachment assembly of the present invention, prior to preloading the assembly;

FIG. 17 is an elevational view with partial breakaway illustrating the bone attachment assembly shown in FIG. 16, during preloading of the assembly;

FIG. 18 is an elevational view with partial breakaway illustrating the environment of a second embodiment of the bone attachment assembly of the present invention from a perspective 90° removed from that shown in FIGS. 15 through 17, in a reloaded implanted condition in connection with a proximal femur prosthesis;

FIG. 19 is an elevational view with partial breakaway illustrating another version of a second embodiment of the bone attachment assembly of the present invention, prior to preloading;

FIG. 20 is an end view illustrating the bone attachment assembly shown in FIG. 19;

FIG. 21 is an elevational view with partial breakaway illustrating the bone attachment assembly shown in FIGS. 19 and 20 in a preloaded condition;

FIG. 27 is an elevational view illustrating a first version of a third embodiment of bone attachment assembly of the present invention, including a main body and an anchor body with integral compliant section, in exploded form;

FIG. 28 is a top view illustrating the main body component of the bone attachment assembly shown in FIG. 27;

FIG. 29 is a side view of an anchor body with integral compliant section, from an angle 90° removed from the angle shown in FIG. 27;

FIG. 30 is a partial cross-sectional view illustrating insertion of a compliant section of the bone attachment assembly within a sleeve formed as part of the main body shown in FIG. 27;

FIG. 31 is a partial cross-sectional view illustrating a main body with integral sleeve and anchor body with integral compliant section, disposed upon and within a remaining bone portion, with the anchor body secured to the surrounding bone cortex prior to the application of traction to the compliant section;

FIG. 32 is an elevational view in exploded form illustrating a second version of the third embodiment of the present invention, including a main body and anchor body with integral compliant section, in modular form;

FIG. 33 is a partial cross-sectional view illustrating the components shown in FIG. 32, in assembled form and disposed within a remaining bone portion, with secured anchor, with traction applied to the compliant section, and with an intercalary segment attached thereto;

FIGS. 34, 35 and 36 are perspective views illustrating three different sizes of an alternative configuration of anchor body and integral compliant section, each having a tapered, self-tapping threaded section;

FIG. 37 is a bottom perspective view illustrating the cutting thread configuration for any of the anchor bodies shown in FIGS. 34, 35 or 36;

FIG. 38 is a perspective view illustrating a configuration of screw used for securing a main body to a compliant section integrally formed with an anchor body;

FIG. 39 is a partial cross-sectional view illustrating a main body attached through the use of the screw shown in FIG. 38 to a tapered threaded anchor body and integral compliant section disposed within a remaining bone portion;

FIG. 40 is a partial cross-sectional view illustrating the attachment of a tibial tray to an compliant section and integral threaded anchor body;

FIGS. 41, 42 and 43 are perspective views illustrating three different sizes of specially-shaped tapered reamers for use in enlarging the intramedullary canal of a remaining bone portion for the insertion of any of the tapered threaded anchors shown in FIGS. 34, 35 or 36;

FIG. 46 is a partial cross-sectional view illustrating the use of a guide device for drilling apertures through the cortex of a remaining bone portion within which an anchor body of the cross-secured type is being installed;

FIG. 47 is a partial cross-sectional view illustrating the use of a face reamer for milling an interface surface of a remaining bone portion to a predetermined angle;

FIG. 48 is a cross-sectional view illustrating another version of bone attachment assembly of the present invention, having a convexly exteriorly shaped main body shoulder portion;

DETAILED DESCRIPTION OF THE PREFERRED EMBODIMENTS

Figure 3:
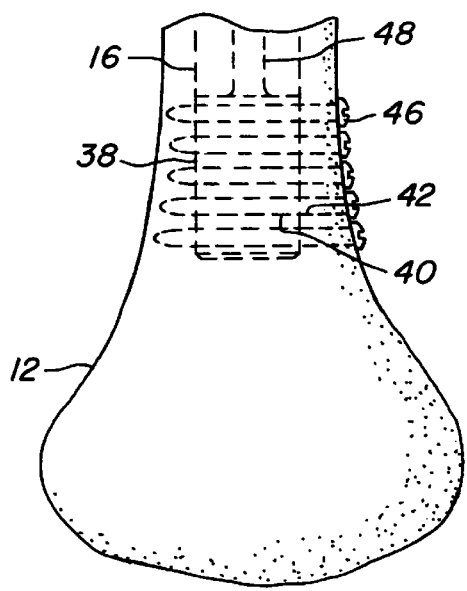
FIG. 3 is a cross-sectional view illustrating one embodiment of an anchor body secured within a cavity of remaining bone portion.

It should be understood that while this invention is described in connection with particular examples, the scope of the invention need not be so limited. Rather, those skilled in the art will appreciate that the following teachings can be used. in a much wider variety of applications than the examples specifically mentioned herein.

Referring now to FIG. 1, there is shown a bone assembly 10, which includes a first remaining bone portion 12 and a second portion 14, as is the case involving a mid-diaphyseal segment replacement. The second portion 14 may be an orthopedic appliance, an orthopedic appliance connected to a second remaining bone portion, or may be replaced by a transcutaneous bar suitable for the attachment of an external appliance, as will be discussed below. The second remaining bone portion may be a portion of the same bone as the first remaining bone portion, or may be a portion of another bone.

The first remaining bone portion 12 is shown to include a first intramedullary cavity 16, which is preferably an enlarged longitudinal cylindrically-shaped bore created to a preselected depth from the osteotomy surface. The first intramedullary cavity 16 may substantially coincide in its longitudinal axis with the natural intramedullary canal of the bone. In those situations where the second portion 14 is in the form of an orthopedic appliance connected to a second remaining bone portion, the second remaining bone portion may similarly include a second intramedullary cavity (not shown), which may preferably be substantially similar in size and shape to the first intramedullary cavity 16. Also, the means of connecting the second remaining bone portion may be entirely different from this arrangement, including the use of bone cement or other suitable materials.

Disposed as a part of the bone assembly 10 is a biocompatible bone attachment assembly, shown generally at 18. The bone attachment assembly 18, in a preferred embodiment, includes a first bone attachment device 20, which is located about the first remaining bone portion 12. The first bone attachment device 20 may be secured to the second portion 14 through the use of a clamp 76, which is preferably of a type discussed below in connection with FIGS. 5 and 6. The bone attachment assembly 18 may also further include a second bone attachment device (not shown) located about the second portion 14, in the situation where the second portion 14 is a second remaining bone portion.

Referring now to FIG. 2, the first bone attachment device 20 is described in greater detail. FIG. 2 is an enlarged cross-sectional view illustrating a bone attachment device 20 as it is secured within the first remaining bone portion 12. The first bone attachment device 20 is shown to include a main body 22 which is constructed of a suitable biocompatible material. Examples of suitable materials are titanium alloys such as Ti-6Al-4V, CoCr (cobalt chromium) alloys and commercially pure titanium. Other suitable materials may be used. It is preferred that the components of the bone attachment assembly 18 be constructed of the same material. Preferably, the main body 22 is substantially cylindrically-shaped, and may include a shoulder portion 24, at least one pin channel 26 and a longitudinal bore 28. The main body 22 is preferably operable to be positioned upon a milled end portion 30 of the first remaining bone portion 12. It will be appreciated that the main body 22 will replace a portion of the length of bone being removed during the surgical procedure, by virtue of its position upon the milled end portion 30.

The milled end portion 30 is created in a preselected geometry relative to the cylindrically-shaped first intramedullary cavity 16. Preferably, as shown in FIG. 2, the milled end portion 30 is formed to an axisymmetric geometry, and most preferably to a convex conical geometry, whose cross-section has a preselected included angle of inclination relative to the longitudinal axis in the direction of the first remaining bone portion 12. Other preselected geometries and angles may also be used. The main body 22 includes an interface surface 32 which is most preferably constructed to substantially match the geometry of the milled end portion 30, thereby providing a substantially flush interface between the milled end portion 30 and the interface surface 32. As such, the interface surface 32 may also be created in an axisymmetric or concave conical geometry, or in another suitable geometry. The interface surface 32 is preferably operable for accepting biological bone attachment by bone ingrowth and/or ongrowth.

The main body 22 is shown to preferably include a cannulated stem portion 34, which is preferably in the form of a single unitary structure. The cannulated stem portion 34 may be of a substantially cylindrical shape, as shown in FIG. 1, or may be tapered along its length at one of several selected major and minor diameter configurations, depending upon the diameter of the original natural intramedullary canal of the bone and also upon the extent of reaming required in forming the first intramedullary cavity 16. Preferably, the major diameter of the cannulated stem portion 34 is represented by a cylindrical portion of the stem, which may fit with reduced lateral movement against the walls defining the first intramedullary cavity 16. As shown in FIG. 2, the cannulated stem portion 34 may occupy a substantial length of the first intramedullary cavity 16. The cannulated stem 34 may be made from the same selection of materials as the main body 22. The cannulated stem portion 34 also includes a longitudinal bore 36 that is coaxial with the longitudinal bore 28 disposed through the main body 22. Preferably, the longitudinal bore 28 and the longitudinal bore 36 are substantially identical in diameter and are relatively positioned so as to form a single continuous bore.

The first bone attachment device 20 further includes means for anchoring the device in an enhanced stationary position within the first intramedullary cavity 16. The means for anchoring the first bone attachment device is shown to be in the form of an anchor body 38 which is located within the first intramedullary cavity 16 at its distal end. The anchor body 38 may be made from the same material as the main body 22. The anchor body 38 includes one or more apertures 40 that are operable for accepting the insertion of one or more fixation devices. The apertures 40 may preferably be a plurality of staggered apertures of substantially the same preselected diameter. One possible staggered arrangement for the apertures 40 is the arrangement shown in FIG. 1. It will be appreciated, however, that any suitable arrangement for the apertures 40 may be used, including those wherein the apertures 40 are in perpendicular or other non-parallel arrangements.

To provide a passageway for the insertion of suitable fixation devices to engage the anchor body 38, one or more fixation bores 42 are provided through the first remaining bone portion 12. The fixation bores 42 are preferably sized and located to substantially match the size and location of the apertures 40 upon the anchor body 38. As such, the fixation bores 42 may also preferably be disposed as a plurality of staggered bores created through the first remaining bone portion 12.

The first bone attachment device 20 also includes one or more engagement devices that are operable to provide an engagement between the anchor body 38 and the first remaining bone portion 12, so as to enhance a substantially secured relation of the anchor body 38 within the first intramedullary cavity 16. In one embodiment, the selection of engagement device is one or more transverse pins 44 which traverse one or more fixation bores 42 on at least one side of the anchor body 38, and also traverse one or more apertures 40 disposed across the anchor body 38. Most preferably, a plurality of transverse pins are used in the same preselected staggered arrangement as the apertures 40 and the fixation bores 42. The transverse pins 44 may be disposed in a substantially parallel relation, as shown. It will be appreciated, however, that the transverse pins 44 may be disposed perpendicularly, or at other preselected relative angles.

The selection of engagement device may also be one or more of interlocking screws 46, as is shown in FIG. 3. FIG. 3 is a cross-sectional view illustrating one embodiment of an anchor body 38 secured within the intramedullary cavity of a remaining bone portion. The interlocking screws 46, like the transverse pins 44, preferably traverse one or more apertures 40 and one or more fixation bores 42. The interlocking screws 46 may be threaded from one side of the first remaining bone portion 12, or may alternatively be threaded from opposite sides. The interlocking screws 46 may also be disposed perpendicularly, or at other preselected relative angles. As before, the interlocking screws 46 may be disposed in a staggered arrangement so as to enhance the stability of the anchor body 38 within the first intramedullary cavity 16. The transverse pins 44 and interlocking screws 46 may both be made from the same materials as the main body 22.

Referring again to FIG. 2, the first bone attachment device 20 is further shown to include means for attaching the main body 22 to the means for anchoring the bone attachment device 20. The means for attaching the main body 22 is provided in the form of a cylindrically-shaped connecting rod 48 that is sized to traverse the longitudinal bore 36 of the cannulated stem 34 and the longitudinal bore 28 of the main body 22, while moving freely longitudinally without substantial restriction from engagement with the cannulated stem portion 34 and the main body 22. The connecting rod 48 may be made from the same material as the main body 22. The connecting rod 48 is operable to be inserted through the main body 22 and the cannulated stem portion 34 to an engagement with the anchor body 38, such that the connecting rod 48 extends from the anchor body 38 through the milled end portion 30. The connecting rod 48 also includes a lower threaded portion 50 that is operable to engage a correspondingly threaded bore 52 located in the upper portion of the anchor body 38. The connecting rod 48 may also be conveniently threaded over its entire length. The connecting rod 48 has a degree of compliancy relative to bone in its construction, such that its disposition alone between the main body 22 and the anchor body 38 provides a compliant fixation between the main body 22 and the anchor body 38.

As shown in FIG. 3, the means for attaching the main body 22 to the means for anchoring the biocompatible bone attachment device 22 may be provided as a connecting rod 48 that is an integral extension of the anchor body 38. As such, the connecting rod 48 also extends from the anchor body 38 through the milled end portion 30.

Figure 4:
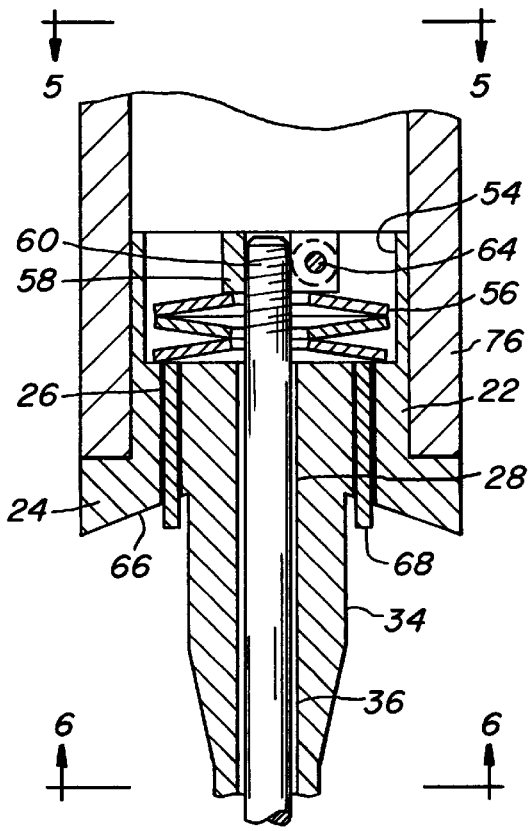
FIG. 4 is a cross-sectional view illustrating the upper compliant portion of the bone attachment device of the present invention.

Referring now to FIG. 4, the means for attaching the main body 22 to the means for anchoring the first bone attachment device 20 may also further include a supplemental interposed compliant device for enhancing the compliance of the bone attachment assembly 18. The supplemental interposed compliant device operates by biasing the connecting rod 48 against the main body 22. FIG. 4 is an enlarged cross-sectional view illustrating a portion of the first bone attachment device 20 of the present invention. The supplemental interposed compliant device may be contained within a cylindrically-shaped recess 54 located atop the main body 22, or may also be operable to abut against another suitable surface of the main body 22. In some arrangements, the supplemental interposed compliant device may project partially from within the recess 54. The supplemental interposed compliant device preferably includes one or more washer springs 56 positioned about the upper portion of the connecting rod 48. As shown in FIG. 4, a plurality of washer springs 56 may be oriented in adjacently opposite directions upon the connecting rod 48. It will be appreciated that other suitable biasing arrangements may be used.

The washer springs 56 may be made from the same materials as the main body 22 set forth above, or may also be made from a nickel-titanium alloy, such as nitinol. The use of nitinol as a material selection for the washer springs 56 tends to reduce the number of individual spring members required. The washer springs 56 may be replaced, however, by at least one compressible elastic cylinder made from a material selected from the group consisting of plastics and polymers. A suitable selection for an elastic cylinder material is polyurethane.

In order to secure the washer springs 56 in a biasing relationship between the main body 22 and the connecting rod 48, a spring biasing means is provided. The spring biasing means may serve the double function of locking means, which may be a lock nut 58 which may be advanced upon an upper threaded portion 60 of the connecting rod 48 at least until it contacts the supplemental interposed compliant device. The lock nut 58 may be made from the same material as the main body 22. The lock nut 58 may be further advanced upon the connecting rod 48 to compress the spring means to a desired degree. Preferably, the lock nut 58 is advanced upon the connecting rod 48 so as to compress the washer springs 56 until increased resistance is noted. This may occur at above about 75% compression, and may preferably occur at about 90% compression. A gap 62 located across the lock nut 58 may be suitably closed to enhance a substantially secured position of the lock nut 58 upon the upper threaded portion 60 of the connecting rod 48, thereby securing the washer springs 56 within the recess 54, and thereby providing a supplemental biasing arrangement between the connecting rod 48 and the main body 22. As such, the first bone attachment device 20 is in an enhanced compliantly attached arrangement.

Figure 5:
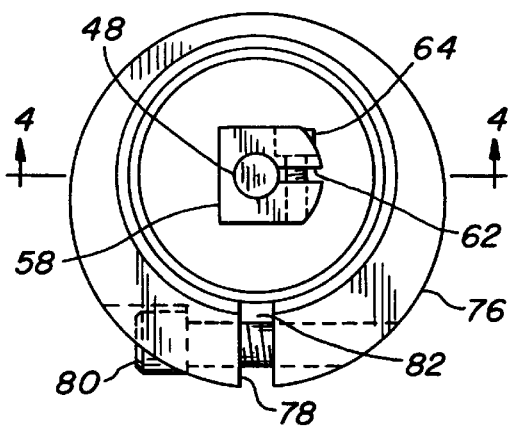
FIG. 5 is a top view illustrating a portion of the device shown in FIG. 4, taken from the perspective 5—5 in FIG. 4.

The lock nut 58 is provided with retention means for enhancing the substantially secured relation of the lock nut 58. The retention means is shown in the form of a retention screw 64 which is operable to traverse a correspondingly threaded receiving hole disposed across the lock nut 58 on either side of the gap 62. The retention screw 64 is operable to be threadably tightened to close the gap 62 to the point where the lock nut 58 is enhanced in a substantially secured relation against the upper threaded portion 60 of the connecting rod 48. The relative positions of the lock nut 58, the washer springs 56 and the recess 54 are illustrated in FIG. 5, which is a top view illustrating a portion of the bone attachment device shown in FIG. 4, taken from the perspective 5—5 in FIG. 4. It will be appreciated that other suitable spring biasing means and retention means may be used. For example, a nut without a gap followed by a lock nut may be used. A lock wire disposed through a hole in a nut is also suitable as a locking means for the spring biasing means.

The spring biasing means may also be provided as a combination of a nut without a gap, followed by means for enhancing a secured relation of the nut upon the connecting rod. This may be provided as a lock nut, as previously described, or may be provided in another suitable form, such as a lock wire disposed through an aperture of the nut.

Referring again to FIG. 4, the first bone attachment device 20 may also be provided with a porous interface coating 66 located upon the interface surface 32. The porous interface coating 66 may be applied by any suitable technique and is for enhancing bone ingrowth into the first bone attachment device 20 from an adjacently positioned milled end portion of a bone, such as that shown at 30 in FIG. 2. The porous interface coating 66 may be made from varieties of the same material as the main body 22, or may also be CoCr (cobalt chromium) beads of diameter approximately $^{20}/_{100}$ths of an inch, sintered together, or a pressed and sintered multiple layer wire grid of titanium alloy wires, or a pressed and sintered coarse wire of one of the above materials, or a plasma sprayed titanium. The porous interface coating 66 may also include a hydroxyapatite layer in conjunction with any of the above material layers.

Figure 6:
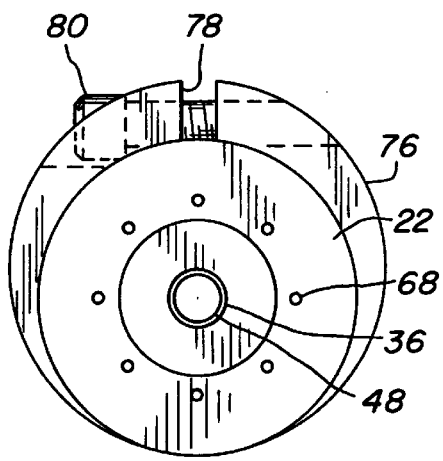
FIG. 6 is a bottom view illustrating the compliant section of the bone attachment device of the present invention, taken from a perspective 6—6 in FIG. 4.

With reference again to FIG. 4, the first bone attachment device 20 may be provided with one or more antirotation pins 68 which are disposed within the pin channel 26 and protrude from the interface surface 32 in the region where the main body 22 contacts an adjacently positioned milled end portion of a bone, such as that shown at 30 in FIG. 2. Referring now to FIG. 6, which is a bottom view illustrating the compliant section of the bone fixation device, taken from a perspective 6—6 in FIG. 4, it can be seen that a plurality of antirotation pins 68 are disposed in a substantially equally spaced circular arrangement about the central axis of the longitudinal bore 28. It will be appreciated that any suitable number of antirotation pins 68 may be employed. Usually, at least one, up to about twelve antirotation pins 68 will be most practical. The preferred length of projection, above the interface surface 32, of each antirotation pin 68 is less than four times the diameter of each pin. The antirotation pins 68 may be made from the same material as the main body 22.

In the situation where only a mid-diaphyseal segment replacement is performed, the second portion 14 discussed in connection with FIG. 1 may in part take on a substantially similar construction as the first remaining bone portion 12. Thus, a bone attachment assembly 18 may be formed from two substantially identically constructed bone attachment devices. Alternatively, the second portion 14 may be provided entirely as an orthopedic appliance. Alternatively, the resection could include adjacent portions of two end-on-end disposed long bones, such that the two attachment assemblies and an interposed orthopedic appliance would serve to restore physiologic linkage between the two long bones. In this way, the two long bones could also be functionally fused, according to the selected interposed orthopedic appliance.

In this situation, a second bone attachment device (not shown) may be provided to be substantially similar to the first bone attachment device 20. It may also be substantially different, for example, attached to its receiving surface with bone cement. With reference now to FIG. 7, FIG. 7 illustrates a bone attachment assembly, indicated generally at 18. The bone attachment assembly 18 is shown to include a first bone attachment device 20 which is fixedly secured to a first remaining bone portion 12, in the manner previously described. The first bone attachment device 20 may then be connected through the use of a clamp 76 to a second portion 14 which is in the form of an orthopedic appliance. The orthopedic appliance may then be similarly connected to a second bone attachment device in a similar manner. In this arrangement, the first bone attachment device 20 acts as a connector, in addition to the orthopedic appliance, which may replace a portion of the length of bone removed during the surgical procedure. In this arrangement, the first bone attachment device 20 and the second bone attachment device are each provided with a compliant capability.

The biocompatible bone attachment assembly 18 is also shown to include means for enhancing a fluid seal between the intramedullary cavity 16 and the external environment. Preferably, this is provided as one or more sealing devices, such as o-rings 70 and 72, which are disposed in a contacting relation with the main body 22 or the connecting rod 48. As such, the o-rings 70 and 72 may be disposed about the edge of the main body 22, within a recess 74 created at the lower surface of the main body 22 adjacent to the connecting rod 48, as shown in FIG. 7, or may be disposed upon other suitable regions of the main body 22. The o-rings 70 and 72 may thus also be disposed about the lock nut 58 or the washer springs 56.

When one or more o-rings 70 and 72 are used, they may enhance a sealed condition of the first bone attachment device 20 as connected to an orthopedic appliance, such as that shown at 14 in FIG. 1. Multiple sealing devices may sequentially reinforce a seal of the first bone attachment device 20 at the entrance to the recess 54 and the entrance to the longitudinal bore 28.

The bone attachment assembly 18 further includes means for securing the first bone attachment device 20 in an enhanced secured relation to the second portion 14 which may be an orthopedic appliance, as shown in FIGS. 1, 4 and 7. This is preferably provided as a clamp which is operable to substantially surround a portion of the main body 22 of the first bone attachment device 20 and a portion of the opposing orthopedic appliance, or second portion 14. One particularly preferred type of clamp is a cylindrically-shaped sleeve clamp 76 which is operable for being enhanced in a secured relation. As shown in FIGS. 5 and 6, the sleeve clamp 76 includes an aperture 78 that is operable to be closed through the threaded rotation of one or more retention screws 80. The sleeve clamp 76 may be made from the same material as the main body 22. It will be appreciated that other suitable means for coupling the first bone attachment device 20 and the second portion 14 may also be used.

The first bone attachment device 20 may also include means for preventing rotation of the sleeve clamp 76 with respect to the main body 22 and the orthopedic appliance 14. This is preferably provided as a key 82 disposed in an engaging relation between the sleeve clamp 76 and the main body 22, as shown in FIG. 5. It will be appreciated that this may be provided by any suitable device disposed between the sleeve clamp 76, the main body 22 and the orthopedic appliance 14.

Referring now to FIG. 8, FIG. 8 is a perspective view illustrating a guide device which can be temporarily applied for creating one or more apertures in the first remaining bone portion for accepting one or more engagement means, such as the transverse pins 44 or interlocking screws 46 shown in FIGS. 2 and 3. The guide device, shown generally at 84, is operable to be attached to a means for anchoring a bone attachment assembly, such as the anchor body 38. The guide device 84 is made from aluminum, a titanium alloy, or preferably, stainless steel. It will be appreciated that other suitable materials may be used. The guide device 84 includes a guide body 86 that is preferably of length at least equal to the total, combined length of the connecting rod 48 and the anchor body 38.

The guide device 84 is shown to include a guide body 86 operable for being disposed adjacent to the first remaining bone portion 12. The guide body 86 includes an upper connecting aperture 88 and a locking screw 90 that is operable for closing the connecting aperture 88. The guide body 86 also includes one or more guide holes 92 for guiding an aperture-forming procedure by accepting the insertion of both alignment devices and drilling implements, as will be discussed below.

The guide device 84 also includes a cannulated holder bar 94 that is operable for being positioned upon the anchor body 38 and connecting rod 48 within the first intramedullary cavity 16 in a coaxial relationship. The holder bar 94 is preferably positioned so as to abut against the top of the anchor body 38. The holder bar 94 is of preselected length and configuration to match the dimensions of the reamed first intramedullary cavity 16. As such, the length of the holder bar 94 is preferably sufficient to protrude from the osteotomy surface, yet is short enough to allow the holder bar 94 to be substantially secured to the connecting rod 48 by a nut 96 threaded onto the connecting rod 48 substantially against the upper surface of the holder bar 94. The holder bar 94 may be of cylindrical shape, and may include a tapered section 98 disposed between a large section 100 having a major diameter and a small section 102 having a minor diameter. The large section 100 is preferably operable to fit with reduced lateral movement against the walls defining the first intramedullary cavity 16, so as to serve as a means for establishing a precise coaxial position of the anchoring means within the first intramedullary cavity 16. One or more other suitable surface irregularities on the holder bar 94 may serve as a means for establishing a precise depth of insertion.

The guide device 84 is also shown to include a positioning bar 104 operable for being mounted between the holder bar 94 and the guide body 86. The positioning bar 104 includes a connecting aperture 106 that is operable for engaging a portion of the holder bar 94. The positioning bar 104 also includes a locking screw 108 for closing the connecting aperture 106 so as to enhance a secured relation between the holder bar 94 and the positioning bar 104. The positioning bar 104 is preferably sized so as to engage the upper connecting aperture 88 of the guide body 86, such that the tightening of the locking screw 90 enhances a secured relation between the positioning bar 104 and the guide body 86. It will be appreciated that the various components of the guide device 84 described above are relatively manipulable and may thus be independently adjusted and set for each particular aperture-forming procedure upon each particular first remaining bone portion 12. The guide device 84 is preferably set to provide one or more guide holes 92 in substantial alignment with one or more apertures 40 disposed within the anchor body 38, so that a drilling procedure directed through one or more guide holes 92 may result in the proper formation of the fixation bores 42 shown in FIGS. 2 and 3.

As shown in FIGS. 8 and 9, the present invention also contemplates the use of one or more self-centering drill bits 112 as especially suitable for creating at least one fixation bore 42 by being inserted through each of the guide holes 92 and directed toward the outer surface of the first remaining bone portion 12. The self-centering drill bit 112 is known in the machine tool industry, and is shown to include a main bit portion 114 and a centering bit portion 116 protruding beyond the main bit portion 114 for drilling a centering hole which guides the drilling operation of the main bit portion 114. The drill bit 112 also includes a drill attachment portion 118 operable for attaching directly to a drilling device (not shown), such as a conventional hand drill. This procedure may also be performed with a standard drill bit (not shown).

Referring now to FIG. 10, FIG. 10 is a partial cut away view illustrating a milling device, shown generally at 120, for milling the osteotomy surface of a first remaining bone portion 12 in a preselected geometry to be coaxial with a first bone attachment device 20. The milling device 120 is shown to include a milling body 122 having a cutting edge 124 of preselected geometry. The preselected geometry of the cutting edge 124 may preferably be such that it creates a conical shape, and more preferably creates a convex conical shape. The milling device 120 further includes means for positioning the milling body 120 upon an osteotomy surface of a first remaining bone portion 12 in a coaxial relationship with the first intramedullary cavity 16. This may be provided as a cannulated pilot member 126 that is operable for being inserted into the first intramedullary cavity 16 up to an abutting relationship with the anchor body 38. Preferably, the cannulated pilot member 126 is of a generally tapered configuration, and includes a cylindrical portion 128 having a major diameter substantially equal to the diameter of the first intramedullary cavity 16. As such, this major diameter defines the nominal size of the cannulated stem portion 34 which is subsequently inserted into the first intramedullary cavity 16. The cannulated pilot member 126 further includes a tip portion 130 which is operable to abut against the anchor body 38. The cannulated pilot member 126 includes a longitudinal aperture 132 that is sized to accept the traverse of the connecting rod 48.

The milling device 120 further includes means for positioning the milling body 122 in a coaxial relationship with the first intramedullary cavity 16. This is provided by the cylindrical portion 128 as previously described and the connecting rod 48 in the longitudinal aperture 132. The milling device 120 also includes means for establishing a preselected depth for a milling procedure upon the osteotomy surface. This is provided in the form of a preselected length of the cannulated pilot member 126 from the cutting edge 124 to the tip portion 130. This distance is preselected to be substantially equal to a desired distance from the anchor body 38 to the subsequently milled osteotomy surface. The cannulated pilot member 126 further includes a shaft portion 134 of preselected length to engage a recess 136 of preselected length within the milling body 122. The milling body 122 may further include a means for enhancing a substantially secured relation between the milling body 122 and the cannulated pilot member 126, such as a set screw 138. The milling body 122 also includes a drill attachment portion 140 for attaching the milling body 122 to a drilling device, such as a conventional hand drill.

As shown in FIG. 11, the means for positioning the milling body 122 in a coaxial relationship with the first intramedullary cavity 16, as well as the means for establishing a preselected depth for a milling procedure can both be provided with a different cannulated pilot member 126, and through a special configuration of the milling body 122 with respect to the connecting rod 48. FIG. 11 is a cross-sectional view illustrating a milling device used for milling an osteotomy surface in a preselected geometry. The milling body 122 may be disposed upon the connecting rod 48 such that the connecting rod 48 extends into the recess 136, and wherein the recess 136 is disposed in a coaxial relation to the first intramedullary cavity 16, by way of the longitudinal aperture 132 in a truncated cannulated pilot member 127. In this arrangement, the means for establishing a preselected depth for a milling procedure is provided by the cylindrical walls defining the recess 136 being of a preselected length substantially equal to the length of the portion of the connecting rod 48 which is greater than the desired distance from the anchor body 38 to the subsequently milled osteotomy surface.

Referring now to FIG. 12, FIG. 12 is a cross-sectional view illustrating a first bone attachment device 20 secured in conjunction with an interposed orthopedic appliance 142. The orthopedic appliance 142 is shown to include a plurality of recesses 144, 146 and 148 for accommodating the insertion of one or more of the washer springs 56, the lock nut 58 and the connecting rod 48. In this example, it should be noted that the main body 22 is shaped somewhat differently than previously described in that the recess 54 may be substantially smaller, thereby allowing the protrusion of one or more of the above components.

Referring now to FIG. 13, FIG. 13 is a cross-sectional view illustrating a transcutaneous bar 150 connected to a device of the present invention. The transcutaneous bar 150 is secured substantially as before by a cylindrically-shaped sleeve clamp 76. The transcutaneous bar 150 is used in the case of amputees, wherein the skin 152 may be repaired around the transcutaneous bar 150 during the surgical procedure. The transcutaneous bar 150 is shown to include as an example a threaded portion 154 which is operable to be threadably engaged with one of several types of external appliances (not shown). The length of the transcutaneous bar 150 preferably allows sufficient length of the threaded portion 154 for a satisfactory threaded engagement with the external appliance used. The transcutaneous bar may be constructed from a material selected from the group consisting of metals and carbon fiber-reinforced resins, although it will be appreciated that other suitable materials may be used. The transcutaneous bar 150 may further be coated with a material that allows the biological attachment of soft tissue, such as skin, and inhibits bacterial access from the external environment. This is preferably provided as a coating 156 disposed upon at least a portion of the external surface of the transcutaneous bar 150. Preferably, the coating material is hydroxyapatite, although it will be appreciated that other suitable coating materials may be used.

Referring now to FIG. 14, FIG. 14 is a perspective view illustrating a reaming device 158 of the present invention. The reaming device 158 is operable for creating an enlarged cylindrical intramedullary cavity, such as the first intramedullary cavity 16, within a first remaining bone portion 12. The reaming device 158 is shown to include a cylindrical portion 160 preferably having a plurality of cutting surfaces, and a tapered tip portion 162 disposed in communication with the cylindrical portion 160. The tapered tip portion 162 also preferably has a plurality of cutting surfaces. The reaming device 158 also includes a drill attachment portion, which is provided as a drill attachment post 164. The reaming device 158 is preferably a left spiral, right cutting device, made for use with standard clockwise hand drills. As such, the reaming device 158 is operable for establishing a first intramedullary cavity 16 within the first remaining bone portion 12, is self-centering, creates a cylindrical cavity, and will not seize in the bone.

In the method of the present invention, a bone segment is replaced with a biocompatible bone attachment assembly, such as that shown at 20. The surgical procedure, as applied to a mid-shaft osteotomy of a femur, generally involves preparing the lateral aspect of the femur for surgery with povidone iodine, and draping the limb for aseptic surgery. The lateral aspect of the femur is then approached between the muscle bellies of the biceps femoris and the vastus lateralis. Wound closure is of a routine nature to those skilled in the art.

The method includes the step of resecting the femur at a preselected location by suitable means of sawing, thereby performing a transverse osteotomy of the femur. This procedure yields a first remaining bone portion 12. The preparation of the first remaining bone portion 12 may then be accomplished as follows. An enlarged cylindrically-shaped first intramedullary cavity 16 is formed within the first remaining bone portion 12 up to a diameter dictated by intramedullary cavity dimensions and to a preselected depth. The preselected depth is preferably sufficient to allow for the insertion of a means for anchoring the first bone attachment device 20 within the first intramedullary cavity 16 to such a depth that subsequent connection of a means for compliantly attaching the main body 22 to the first remaining bone portion 12 may protrude from the osteotomy surface.

The enlarged first intramedullary cavity is formed by attaching the reaming device 158 to a drilling device, such as a conventional hand-held power drill, henceforth denoted as a hand drill, at the drill attachment post 164. The reaming device 158 is then inserted into the intramedullary canal. The hand drill is then activated, and the reaming device 158 is advanced in a longitudinal direction into the first remaining bone portion 12, while the reaming device 158 is being rotated by the drilling device. This is repeated with progressively larger reamers until the reaming device 158 has clearly engaged the inner walls. A larger reamer may be used at the outlet than at the depth of the intramedullary cavity. A cylindrically-shaped enlarged first intramedullary cavity 16 as an enlargement of the natural intramedullary canal of the first remaining bone portion 12 is thus created.

The holder bar 94 of appropriate nominal diameter is first positioned upon the connecting rod 48 in an abutting relation with the anchor body 38. A nut 96 is then advanced onto the upper threaded portion 60 of the connecting rod 48 until substantially tightened against the top surface of the holder bar 94. The positioning bar 104 is then engaged with the holder bar 94 in a substantially perpendicular relation such that the holder bar 94 passes through the connecting aperture 106. The guide body 86 is engaged with the positioning bar 104 in a substantially perpendicular relation by sliding the upper connecting aperture 88 over the positioning bar 104. The apertures 40 in the anchor body 38 are then aligned with the guide body holes 92 in the guide body 86, by way of temporary rods (not shown) traversing both the guide body holes and the anchor body holes. The locking screws 90 and 108 may then be substantially tightened, thereby enhancing a secured relation between the guide body 86 and the anchor body 38.

Once the above components of the guide device 84 are positioned and secured, the holder bar 94 is inserted into the intramedullary cavity 16 to the depth indicated by a gauge on the side of the holder bar (not shown).

The self-centering drill bit 112 is connected to a drilling device, such as a hand drill at the drill attachment portion 118. The self-centering drill bit 112 is then inserted through a guide hole 92 in a substantially perpendicular direction to the guide body 86 to meet the outer surface of the first remaining bone portion 12. The centering bit portion 116 is first advanced into the first remaining bone portion 12 as the self-centering drill bit 112 is rotated by the drilling device. The fixation bores 42 are thus created by advancing the centering bit portion 116, followed by the main bit portion 112, through the first remaining bone portion 12 and into the anchor body 38. The self-centering drill bit 112 may be further advanced through the entire width of the first remaining bone portion 12.

Once the first fixation bore 42 is created, the self-centering drill bit 112 is left in the fixation bore 42 while additional fixation bores 42 are created using additional self-centering drill bits 112, to additionally stabilize the guide device 84 for the remaining drilling procedures. The above steps may be repeated as many times as desired to create several fixation bores 42.

The fixation bores 42 may be created to form contiguous straight channels through the entire width of the first remaining bone portion 12 from one external surface to the other. It will be appreciated that the fixation bores 42 may be created to a limited depth within the first remaining bone portion 12 as well. A similar procedure may be employed to create one or more fixation bores 42 through the first remaining bone portion 12 from opposite sides of the first intramedullary cavity 16 or from preselected relative angles. The fixation bores 42 may thus be created all parallel in the same direction, or may be a series of oppositely or angularly disposed fixation bores 42 created from opposite or adjacent external surfaces of the first remaining bone portion 12 on opposite or adjacent sides of the first intramedullary cavity 16.

Once the desired fixation bores 42 have been created, one or more fixation elements, such as transverse pins 44 or interlocking screws 46 are then forcibly inserted or threadably inserted into each fixation bore 42 and into each aperture 40, so as to engage the anchor body 38 and the first remaining bone portion 12. The first self-centering drill bit 112 is removed only after the first fixation element has been inserted. The guide device 84 is then disengaged and removed.

The milling device 120 is then used to create a milled end portion 30 upon the first remaining bone portion 12. Where the milling device 120 includes a cannulated pilot member 126, as set forth in FIG. 10, the cannulated pilot member 126 is inserted into the recess 136 of the milling body 122, until the upper edge of the cylindrical portion 128 contacts the cutting edge 124. A set screw 138 is suitably tightened to enhance a secured relation between the milling body 122 and the cannulated pilot member 126. The milling body 122 is then attached at the drill attachment portion 140 to a drilling device, such as a hand drill. The cannulated pilot member 126 is then inserted into the first intramedullary cavity 16 such that the milling device 122 is positioned atop the first remaining bone portion 12 with its longitudinal axis in a substantially collinear relation with that of the first remaining bone portion 12. Pressure is then exerted in a downward axial direction as the milling device 120 is rotated by the drilling device, thereby rotating the cutting edge 124 upon the osteotomy surface, and thereby removing portions of the bone from this surface. The rotation is continued until the tip portion 130 of the cannulated pilot member 126 abuts against the anchor body 38. At this point, the preselected dimensions of the above components will have caused the rotation of the cutting edge 124 to form a milled end section 30 of a preselected geometry corresponding to that of the cutting edge 124, which is located at a preselected distance from the anchor body 38.

In the situation where a truncated cannulated pilot member 127 is employed, as shown in FIG. 11, the milling body 122 may be connected to a drilling device, such as a hand drill, at the drill attachment portion 140, as before. The milling body 122 and truncated cannulated pilot member 127 may then be disposed upon the connecting rod 48, such that the connecting rod 48 extends into the recess 136 of the milling body 122. Then, the milling body 122 may be rotated by the hand drill as before, with the milling body forced in a downward axial direction until the upper surface of the connecting rod 48 contacts the upper surface of the recess 136. At this point, the preselected dimensions of the connecting rod 48 and the recess 136 will result in the formation of a milled end portion 30 of preselected geometry and location, as before.

In accordance with the method of the present invention, the main body 22 is then positioned in an abutting relation between the interface surface 32 and the milled end portion 30, such that the connecting rod 48 traverses the longitudinal bore 28 of the main body 22 and protrudes into the recess 54 of the main body 22. It will be appreciated that the connecting rod 48 may protrude above any suitable contact surface upon the main body 22. As shown in FIG. 2, where the main body 22 includes an cannulated stem portion 34, the cannulated stem portion 34 is inserted into the first intramedullary cavity 16 as the main body 22 is positioned upon the milled end portion 30. The connecting rod 48 then traverses both the longitudinal bore 28 of the main body 22 as well as the longitudinal bore 36 of the cannulated stem portion 34. Once the main body 22 is positioned upon the milled end portion 30, the pin channels 26 may be used to guide a suitable drilling device for the creation of one or more recesses in the milled end portion 30 for accepting the antirotation pins 68. Once this drilling operation is completed, one or more antirotation pins 68 are disposed within one or more pin channels 26 into the milled end portion 30, thereby preventing rotation of the main body 22 with respect to the milled end portion 30.

One or more fluid seal devices, such as o-rings 70 and 72, may then be positioned at such locations as the recess 74 shown in FIG. 7, and also along the top rim of the main body 22.

In the next step of the method of the present invention, one or more supplemental interposed compliant devices, which are preferably one or more washer springs 56, or one or more compressible elastic cylinders, may optionally be positioned upon the connecting rod 48 such that they are retained within the recess 54 of the main body 22. When a plurality of washer springs 56 are used, it is preferred that they be used in an adjacent oppositely disposed relation. A retaining means, such as a lock nut 58, is advanced upon the upper threaded portion 60 of the connecting rod 48 until the lock nut 58 compresses the washer springs 56 or elastic cylinders until increased resistance is noted. This may occur at above about 75% compression, and may preferably occur at about 90% compression. The lock nut 58 is then enhanced in a secured relation against the connecting rod 48 by tightening the retention screw 64, which closes the gap 62. Where the supplemental interposed compliant devices are not employed, the lock nut 58 is advanced directly to the bottom of the recess 54.

In the situation where the second portion 14 is an orthopedic appliance, as shown in FIGS. 1 and 7, the sleeve clamp 76 shown in FIGS. 5 and 6 is first positioned upon a portion of either of the main body 22 of the first bone attachment device 20 or the orthopedic appliance. Thereafter, the main body 22 of the first bone attachment device 20 is brought in an end to end abutting relation with a suitable portion of the orthopedic appliance, and the sleeve clamp 76 is positioned so as to substantially surround the main body 22 and a section of the artificial bone portion, and the key 82 is engaged, if it is to be used. The sleeve clamp 76 is then enhanced in a substantially secured relation by tightening the retention screws 80.

In the situation where two compliant bone fixation devices are used in connection with a first remaining bone portion 12 and a second portion 14, which is in the form of a second remaining bone portion of the same or a different bone, the above steps for creating and positioning the first bone attachment device 20 upon the first remaining bone portion 12 are repeated in substantially identical form for creating and positioning a second bone attachment device (not shown) upon the second portion 14. Alternatively, the second bone portion may be attached by a means not in accordance with this invention. In this arrangement, the second bone attachment device may be attached to an interposed orthopedic appliance, which is shown at 142 in FIG. 12. A sleeve clamp 76 as shown in FIGS. 5 and 6 or other connecting means is positioned upon either of the main body 22 of the first bone attachment device 20 or the interposed orthopedic appliance 142. The main body 22 of the first bone attachment device 20 is then brought in an end to end abutting relation with the interposed orthopedic appliance 142. The sleeve clamp 76 is then positioned so as to substantially surround a portion of both the main body 22 and the interposed orthopedic appliance 142, and is tightened as before.

In the situation where it is necessary to provide for the attachment of external appliances following amputation, the steps of this method are provided with reference to FIG. 13. The components of the first bone attachment device 20 are substantially assembled, as before. A transcutaneous bar 150 is positioned in an abutting relation to the main body 22 and the sleeve clamp 76 is secured as before. In this procedure, the skin 152 is repaired to substantially surround the transcutaneous bar 150 at the end of the surgery, so that the transcutaneous bar 150 is operable to extend through the repaired skin section for subsequent connection to an external appliance.

A second embodiment of the present invention will now be described with reference to FIGS. 15–25. Referring now to FIG. 15, there is shown an elevational view with partial breakaway illustrating the environment of a second embodiment of the apparatus of the present invention. FIG. 15 shows a bone attachment assembly 200 in an implanted condition within a remaining bone portion 202 following resection. The first remaining bone portion 202 is shown to be in the form of a resected femur, although it will be appreciated that the present invention may be used with other bones as well. The bone attachment assembly 200 is suitable for being connected to a second remaining bone portion, an orthopedic appliance connected to a second remaining bone portion, an orthopedic appliance serving as a complete bone replacement, a transcutaneous bar suitable for the attachment of an external appliance or any other suitable device. Therefore, it will be appreciated that the apparatus of the present invention may be used as part of a replacement for a long bone diaphysis or may be used in another portion of any suitable bone. As before, any second remaining bone portion to which the bone attachment assembly 200 may be connected may be a portion of the same bone as the first remaining bone portion 202, or may be a portion of another bone.

The first remaining bone portion 202 is shown to include a first intramedullary cavity 204. The first intramedullary cavity 204 may preferably be a longitudinal bore that includes of at least a portion of the natural intramedullary cavity of the bone. Alternatively, the first intramedullary cavity 204 may be a bore created in any suitable section of bone, such as within or across a proximal section of a femur. In any arrangement, the first intramedullary cavity 204 is created within the bone to a preselected depth from a cut bone surface or the natural external bone surface. This preselected depth preferably corresponds to the expected depth of insertion of a portion of the bone attachment assembly 200 within the bone.

In the version of the second embodiment of the present invention shown in FIG. 15, the first intramedullary cavity 204 is an enlarged natural intramedullary cavity of the bone. The first intramedullary cavity 204 thus substantially coincides in its longitudinal axis with that of the natural intramedullary cavity of the bone. The bone attachment assembly 200 may also be inserted within the natural intramedullary cavity of the bone, without further enlargement, where suitable.

The bone attachment assembly 200 is constructed of a suitable biocompatible material, such as those previously described. It will be appreciated that all of the materials set forth in the second embodiment herein may be made from the same materials as previously described or any other suitable materials. The bone attachment assembly 200 includes a main body 206 that is substantially cylindrically-shaped, and is preferably operable to be positioned upon a surface of the first remaining bone portion 202. To provide means for contacting a bone surface in a special relation, the main body 206 may include a special configuration or extension, such as a shoulder portion 208. The surface of the first remaining bone portion 202 which contacts the bone attachment assembly 200 may be a cut bone surface, a natural external bone surface, or a specially configured bone surface, such as milled end portion 210. Although the milled end portion 210 is shown in a convex conical geometry, it will be appreciated that any suitable geometry may be used. The main body 206 preferably includes an interface surface 212 for abutting against a surface of the first remaining bone portion 202. The interface surface 212 may be formed in any desired configuration upon the main body 206, the shoulder portion 208 where present, or both. Suitable configurations for the interface surface 212 include geometries corresponding to geometries naturally occurring or formed upon the bone surface, including planar, concave, convex, concave conical and convex conical. Preferred geometries for the interface surface 212 are those that maximize the advantages of maintaining desired contact, pressure and centering with relation to the bone surface. The concave conical arrangement shown in FIG. 15 is a preferred geometry. It will be appreciated, however, that other suitable geometries may be used, which may include grooves, pins or any other features as may be desirable.

As shown in FIG. 15, the bone attachment assembly 200 further includes an extension 214 connected to the main body 206. The extension 214 is configured in a male tapered arrangement for connection with any of the devices or remaining bone portions mentioned above. The extension 214 may be connected to or may be integrally formed with the main body 206. It will be appreciated that the extension 214 may also include any suitable configuration for facilitating attachment to any device or bone portion mentioned above. It will further be appreciated that the main body 206 and the extension 214 may replace a portion of the length of bone being removed during the surgical procedure, by virtue of their position upon the milled end portion 210 of the first remaining bone portion 202. The extension 214 may include one or more configured surfaces for engagement of one or more devices or appliances. As shown in FIGS. 15–17, this may include one or more engagement recesses 215.

When the bone surface contacting the bone attachment assembly 200 is a cut surface of a long bone diaphysis, a milled end portion 210 is preferably created in a preselected geometry relative to the first intramedullary cavity 204, as described previously. A specially configured bone contact surface, of any type, which may be similar to the milled end portion 210 shown in FIG. 15, may also be prepared upon any suitable section of bone. In one preferred arrangement, shown in FIG. 15, the milled end portion 210 is formed to an axisymmetric geometry, and most preferably to a convex conical geometry, whose cross-section has a preselected included angle of inclination relative to the longitudinal axis in the direction of the first remaining bone portion 202. This same principle can be translated to the formation of any bone contact surface on any section of bone, especially where it is desirable to obtain certain advantages of contact described above. It will therefore be appreciated that other preselected geometries and angles may also be used. The geometry of the interface surface 212 is most preferably constructed to substantially match the geometry of the milled end portion 210, thereby providing a substantially flush interface between the milled end portion 210 and the interface surface 212. The interface surface 212 is preferably operable for accepting biological bone attachment by bone ingrowth and/or ongrowth. The interface surface 212 may also enhance stability of the main body 206 with respect to the bone. Thus, the interface surface 212 may include a suitable coating or other surface treatment, as well as ridges or undulations for this purpose.

To provide means for anchoring the bone attachment assembly 200 in a substantially stationary position within a cavity of the first remaining bone portion 202, an anchor body 216 is provided. The anchor body 216 is disposed at the distal end of the bone attachment assembly 200 relative to the main body 206. The anchor body 216 is preferably sized and located relative to the main body 206 to be disposed within the first intramedullary cavity 204 at its distal end when the bone attachment assembly 200 is placed within and upon a bone. The anchor body 216 includes one or more apertures 218 that are operable for accepting the insertion of one or more fixation devices. The apertures 218 may preferably be a plurality of staggered apertures of substantially the same preselected diameter. One possible staggered arrangement for the apertures 218 is the arrangement shown in FIG. 15. It will be appreciated, however, that any suitable arrangement for the apertures 218 may be used, including those wherein the apertures 218 are in perpendicular or other non-parallel arrangement. The apertures 218 may also be of any suitable number and size.

To provide a passageway for the insertion of suitable engagement devices to engage the anchor body 216, one or more fixation bores 220 are created through the first remaining bone portion 202. The fixation bores 220 are preferably sized and located to substantially correspond to the size and location of the apertures 218 located within the anchor body 216. As such, the fixation bores 220 may also preferably be a plurality of staggered bores created through the first remaining bone portion 202.

The bone attachment assembly 200 also includes one or more engagement devices that are operable to provide an engagement between the anchor body 216 and the first remaining bone portion 202. The engagement devices enhance a substantially secured relation of the anchor body 216 within the first intramedullary cavity 204. In the embodiment shown in FIG. 15, the selection of engagement device is one or more transverse pins 222 operable for being inserted through one or more fixation bores 220 on at least one side of the anchor body 216, and also through one or more apertures 218 disposed across the anchor body 216. Most preferably, a plurality of transverse pins 222 are inserted through the apertures 218 and the fixation bores 220 on both sides of the anchor body 216. Although the transverse pins 222 may be disposed in a substantially parallel relation as shown, it will be appreciated that the transverse pins 222 may be disposed in other preselected directions and at other angles as the apertures 218 and the fixation bores 220 may be disposed. As before, it will be appreciated that the selection of engagement device may also be one or more interlocking screws or other suitable devices. In addition, the engagement devices may be inserted from opposite sides of the anchor body 216, as before.

The bone attachment assembly 200 of the present invention exhibits a preselected state of compliance that is retained in the implanted condition of the assembly. Furthermore, the bone attachment assembly 200 in an implanted condition applies a force across the milled end portion 210 which maintains interface stability. The force applied by the compliant section 224 in an expanded condition is generally in the range of from about 100 lbs. to about 1000 lbs. A typical amount of force applied is 400 lbs. Upon implantation, this force is distributed across the area of the bone surface, represented by the milled end portion 210. It will be appreciated the desired amount of force exerted will vary from application to application, and will depend upon the size of bone involved and the cortical wall thickness and may depend upon other features of the bone or the patient. Preferably, this involves loading the bone attachment assembly 200 to a condition of expansion prior to implantation. To provide means for allowing the bone attachment assembly 200 to exhibit a condition of compliance, the bone attachment assembly 200 includes a compliant section 224. The compliant section 224 is disposed between the main body 206 and the means for anchoring the bone attachment assembly 200. The compliant section 224 is preferably an elongated bar or rod that is an integrally formed extension between the main body 206 and the anchor body 216. Alternatively, the compliant section 224 may take on any suitable construction where the compliant section 224 is manufactured separately from the main body 206 and the anchor body 216, and assembled or attached after the individual components are manufactured, or during the surgical procedure. This may include a modular system of like or differing materials, and can include a traction rod attached to the compliant section 224, where the traction rod itself is compliant relative to the bone, such that it contributes to the compliance of the system. The compliant section 224 may preferably be of a cylindrical shape having a diameter equal to or greater than the anchor body 216. In this arrangement, the compliant section 224 and the anchor body 216 fit snugly within the first intramedullary cavity 204. The bone attachment assembly 200 is preferably preloaded prior to implantation by expanding the compliant section 224 alone to a preselected condition of expansion, according to the forces desired as allowed by the elastic properties of the compliant section 224. It will be appreciated, however, that the means for allowing the bone attachment assembly 200 to exhibit to a condition of compliance may take on any other suitable form. For example, the bone attachment assembly 200 may include more than one compliant section or may include a compliant section disposed in a different configuration or at a different location upon the bone attachment assembly 200 as may be desirable for accomplishing particulars of compliance or attachment. Also, it will be appreciated that the loading of the bone attachment assembly 200 can be accomplished in any suitable manner prior to, during or after implantation. The compliant section 224 is maintained in a condition of expansion following implantation by securing the anchor body 216 at a preselected location within the first intramedullary cavity 204 during a maintained expansion of the compliant section 224 while the milled end portion 210 abuts the interface surface 212.

In a state of expansion during an inserted condition within a bone, the compliant section 224 is operable for experiencing expansion and contraction in response to physiological expansion and contraction in the adjacent bone. Thus, one function of the bone attachment assembly 200 involves the expansion and contraction of the compliant section 224 as necessary to allow the substantial transfer of physiologic loads through the surrounding bone, rather than through the implanted device. The compliant section 224 is preferably formed as an elongated extension that is made compliant to the desired degree and with the desired characteristics. Preferred configurations for accomplishing the compliance of any compliant section 224 discussed herein include perforation into the shape of a single or double helical spring, or springs in the shape of an accordion, although it will be appreciated that any suitable perforated configuration for any compliant section discussed herein may be used. The configuration shown in FIGS. 15–17 is a single helical spring configuration. Such configurations allow the compliant section 224 to expand and contract as a coil spring. The number of turns, the inner diameter of the spring, the outer diameter of the spring, the size of each turn and the angle of each turn of the spring configuration in the compliant section 224 can be manipulated as desired to achieve a specific load, a specific spring rate and a specific deflection capacity. It will be realized that in other arrangements, other suitable non-helical configurations or perforations or other features may be used for the compliant section 224. The present and other embodiments of the present invention are advantageous because they provide compliant fixation through an integrally formed apparatus.

An advantage of the bone attachment assembly 200 of the present invention involves the method by which the compliant section 224 is made. The stock from which the bone attachment assembly 200 is made is first machined to a desirable shape by methods well known to those skilled in the art. The portion of the assembly that is in the form of an elongated bar or rod is then perforated or cut into a configuration that will result in a compliance in this section of the assembly. The perforation or cutting may be accomplished by electrical discharge machining (EDM), which involves the use of a material that conducts electricity to remove material to form desired shapes in another material by using electric spark to remove pieces of the material. This process is applied to the elongated bar or rod portion of the bone attachment assembly 200 to form perforations of a desired shape, such as a helical spring arrangement, directly therein. Typically, a brass wire of a thickness ranging from about three thousandths of an inch to about sixteen thousandths of an inch is used to form the desired perforations. A brass wire of about twelve thousandths of an inch is one common wire used. It will be appreciated that this process may be accomplished using other material selections, configurations and sizes for the material used to create the perforations.

In the method of the present invention, the perforations in the elongated bar or rod are made by contacting a cutting wire with a surface of the elongated bar or rod, or by drilling an aperture into the bar or rod into which the cutting wire may be inserted. Where the cutting wire contacts the external surface of the elongated bar or rod, a single helix is formed. Where the cutting wire is inserted into an aperture formed within the elongated bar or rod, a double helix is formed. An aperture may also be created longitudinally through the elongated bar or rod as well. Where the cutting wire contacts the external surface of the elongated bar or rod, the cutting is accomplished by turning the bar or rod and feeding the wire at an angle suitable for the desired shape of cut. Where the cutting wire is inserted into an aperture formed within the elongated bar or rod, the cutting is accomplished by turning the bar or rod and feeding the wire into the material. The speed at which the wire is fed along the bar or rod relative to its speed of rotation determines the configuration of the resulting perforation, such as the pitch of a helical spring being created. It will be appreciated that the selection of base material and cutting material, the angle of cutting, the inside and/or outside diameter of the bar or rod, the length of cutting and other particulars of the cutting process may be varied to adjust the characteristics of the spring being created. Alternatively, other methods may be utilized to form a spring within the elongated bar or rod portion of the bore attachment assembly 200. These include water jet cutting, blade cutting and laser cutting, as well as other methods that those skilled in the art will appreciate.

As mentioned previously, the bone attachment assembly 200 is preferably loaded to a condition of expansion prior to completion of the surgical procedure. The condition of expansion is an amount of expansion sufficient to assure adequate interface compression force between the milled end portion 210 and the interface surface 212 upon completion of the surgical procedure. This is accomplished by converting the compliant section 224 to a preselected condition of expansion, before, during or after the anchor body 216 is inserted into the first intramedullary cavity 204. To provide means for converting the compliant section 224 to a condition of expansion, the present invention provides multiple methods. In one method, a preloading rod 250 is operable to expand the compliant section 224 by engaging the bone attachment assembly 200 on both sides of the compliant section 224, and forcing the two sides of the assembly in opposite directions. As shown in FIGS. 16 and 17, the preloading rod 250 is sized for insertion within an elongated bore 252 disposed through the extension 214, the main body 206, the compliant section 224 and into the anchor body 216 to a depth proximal of the apertures 218. To provide means for engaging the preloading rod 250 with the bone attachment assembly 200, the preloading rod 250 includes a threaded portion 254 that may be threaded into a threaded bore 256 located at the proximal end of the bore 252. The preloading rod 250 is of a greater length than that of the bore 252 so that the portion of the preloading rod 250 distal to the threaded portion 254 may be inserted to or almost to the complete length of the bore 252. Once this distal portion of the preloading rod 250 is inserted into the bore 252, the distal end of the preloading rod 250 engages the distal end of the bore 252. Once the preloading rod 250 contacts the distal end of the bore 252, any further advancement of the preloading rod 250 will cause an expansion of the compliant section 224. Thus, subsequent threading of the threaded portion 254 into the threaded bore 256 causes the distal end of the preloading rod 250 to push against the distal end of the bore 252, progressively forcing the distal end of the bore 252 in a distal direction, and causing the compliant section 224 to expand progressively as the threaded portion 254 is advanced into the threaded bore 256. The preloading rod 250 further includes means for engaging a tool, such as a knob 258 at its proximal end for facilitating advancement of the preloading rod 250.

An additional method is where the anchor body 216 and the main body 206 are in place, and a traction member extends from the compliant section 224 through the main body 206 and the extension 214. A removable traction device applies a traction force to this traction member, thereby elongating the compliant section 224 and simultaneously applying an equal interface force across the interface surface 212. When the desired force is achieved, a position-holding device is attached to the traction bar, preventing it from reassuming the non-expanded condition as traction is removed. A third method is to have an extension of a compliant section extending to or through an aperture of the main body 206, the extension including a threaded portion at its proximal end. A threaded member can be advanced upon the threaded portion of the extension against the main body 206, thereby causing the expansion of the compliant section 224 in a proximal direction.

FIG. 16 shows the bone attachment assembly 200 in a condition prior to insertion of the preloading rod 250, with the compliant section 224 in a non-expanded condition. FIG. 17 shows the bone attachment assembly 200 with the preloading rod 250 threaded fully into the bone attachment assembly 200, with the compliant section 224 at an intermediate state of expansion. It will be appreciated that the preloading rod 250 may be threaded into the bone attachment assembly 200 to any desired degree. Preferably, the preloading rod 250 is used in the above manner to preload the bone attachment assembly 200 by expanding the compliant section 224 prior to implantation. The compliant section 224 will typically be expanded prior to implantation by an amount sufficient to assure adequate interface compression force upon removal of the preloading rod 250. Once the bone attachment assembly 200 is inserted within the first intramedullary cavity 204 and the anchor body 216 is secured as described above, the subsequent dethreading of the preloading rod 250 and its withdrawal from the assembly will leave the compliant section 224 in a substantially maintained state of expansion. The expanded condition of the compliant section 224 is maintained in the implanted state by the abutment of the interface surface 212 against the milled end portion 210 in combination with the maintained stationary condition of the anchor body 216 by the fixation devices such as the transverse pins 222.

Referring now to FIG. 18, there is shown a bone attachment assembly 200 according to the present invention in conjunction with a femoral prosthesis 270. The femoral prosthesis 270 is shown to include an aperture 272 having a female taper substantially corresponding to the male taper of the extension 214. Thus, the femoral prosthesis 270 can be press fitted upon the bone attachment assembly 200. The femoral prosthesis 270 is typically used in reconstructive and limb salvage surgeries. It will be appreciated that the femoral prosthesis 270 is one of several types of devices which can be attached to the bone attachment assembly 200. The femoral prosthesis 270 is shown to include an intercalary extension segment 274 and a femoral component 276. It will be appreciated that any of the devices used for connecting the bone attachment assembly 200 can be made of one or more pieces or segments. The femoral prosthesis 270 is constructed of titanium alloy, although it will be appreciated that other suitable materials may be used. In addition, one or more surfaces of the femoral prosthesis 270 or any other attached device may include a coating or other surface treatment such as ridges or undulations, for promoting bone ingrowth and/or ongrowth, for enhancing stability, or for enhancing any other characteristic of the device.

Referring now to FIGS. 19 and 20, there is shown another version of the second embodiment of the present invention. In this version, a bone attachment assembly is shown generally at 280. The bone attachment assembly 280 includes a main body 282 which includes a shoulder portion 284. The main body 282 is further shown to include an interface surface 286, which is of a concave conical geometry in similar fashion as before. In this version of the bone attachment assembly 280, the main body 282 is shaped in a tapered configuration.

The bone attachment assembly 280 is further shown to include an anchor body 288 located at its distal end. The anchor body 288 is shown in this arrangement to include four apertures 290 for containing suitable fixation devices for fixation of the anchor body 288 to a surrounding remaining bone portion. As can be seen in FIG. 19, the apertures 290 are located in a square arrangement which is different from the staggered arrangement of five apertures discussed previously. It will therefore be appreciated that in any version of assembly discussed herein, any suitable aperture configuration may be used.

The bone attachment assembly 280 further includes a compliant section 292 which is an elongated section disposed integrally between the main body 282 and the anchor body 288, in similar fashion as before. The bone attachment assembly 280 further includes an extension 294 which is generally of a male tapered configuration, and is suitable for direct attachment of a suitable orthopedic device, as before. The bone attachment assembly 280 also includes an elongated bore 296 that traverses the extension 294, the main body 282 and the compliant section 292. As before, the bore 296 is suitable for accepting the insertion of a rod (not shown) for expanding the compliant section 292 to a condition of expansion. The bone attachment assembly 280 also includes a threaded bore 298 disposed at the proximal end of the bore 296. The bore 296 and the threaded bore 298 function in substantially the same way as the bore 252 and threaded bore 256 previously described. In the arrangement shown in FIG. 19, the compliant section 292 is in a non-expanded condition.

Referring now to FIG. 21, the bone attachment assembly 280 shown in FIGS. 19 and 20 is shown in a preloaded condition. To provide means for loading the compliant section 292 to a condition of expansion, the present invention provides a preloading rod 302, having a threaded portion 304 and a knob 306 in similar fashion as before. In this arrangement shown in FIG. 21, the compliant section 292 is shown to be in an expanded double helical configuration. This expanded configuration is the result of inserting the preloading rod 302 within the bore 296 and threading the threaded portion 304 within the threaded bore 298, in similar fashion as before.

Figure 22:
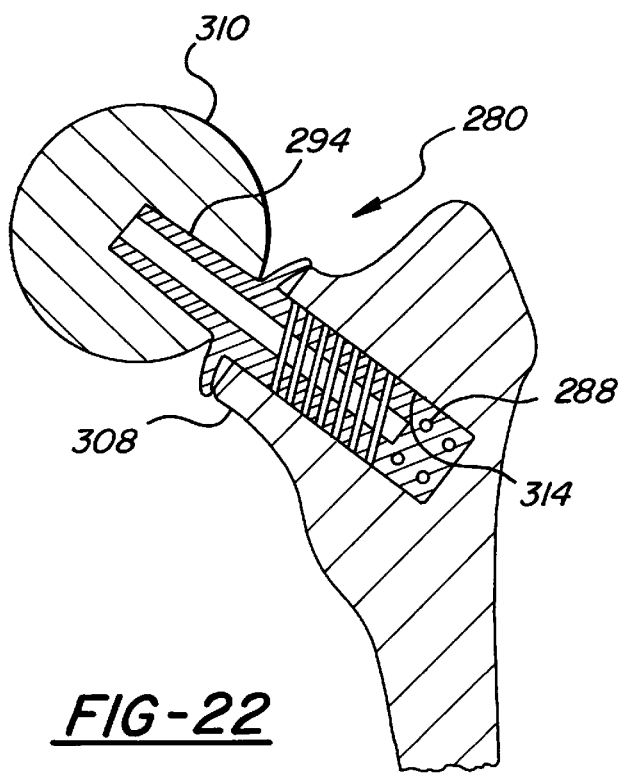
FIG. 22 is a side cross-sectional view illustrating the version of the second embodiment of the bone attachment assembly of the present invention shown in FIGS. 19 through 21 in an implanted condition in connection with a primary hip prosthesis.
Figure 23:
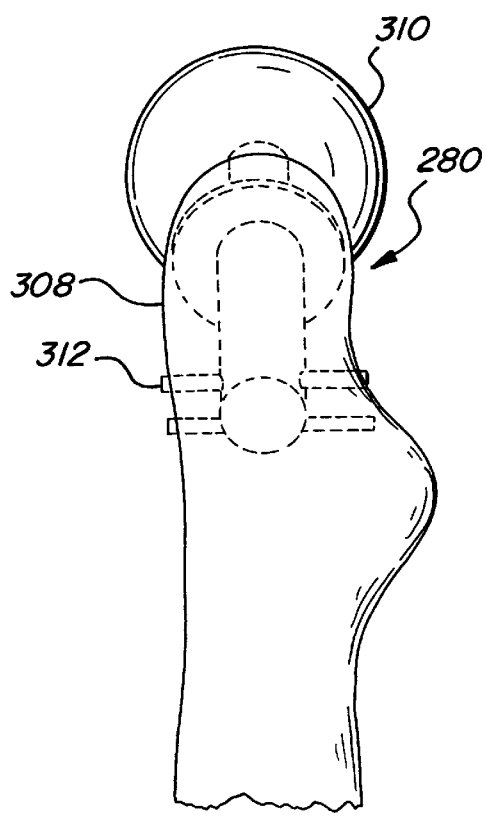
FIG. 23 is a side elevational view illustrating the bone attachment assembly of the present invention shown in FIG. 22 from a perspective 900 removed from that shown in FIG. 22.

Referring now to FIGS. 22 and 23, there is shown the bone attachment assembly 280 described in connection with FIGS. 19–21, in an implanted condition within a proximal femur 308. In this arrangement, a femoral head prosthesis 310 is shown to be press fitted upon the extension 294. Referring now to FIG. 23, it can be seen that a plurality of transverse pins 312 are used to maintain the anchor body 288 in a substantially stationary position within a cavity 314 disposed within the proximal femur 308. It will be therefore be appreciated that the bone attachment assembly of the present invention can be used within other portions of bone besides an intramedullary cavity.

Figure 24:
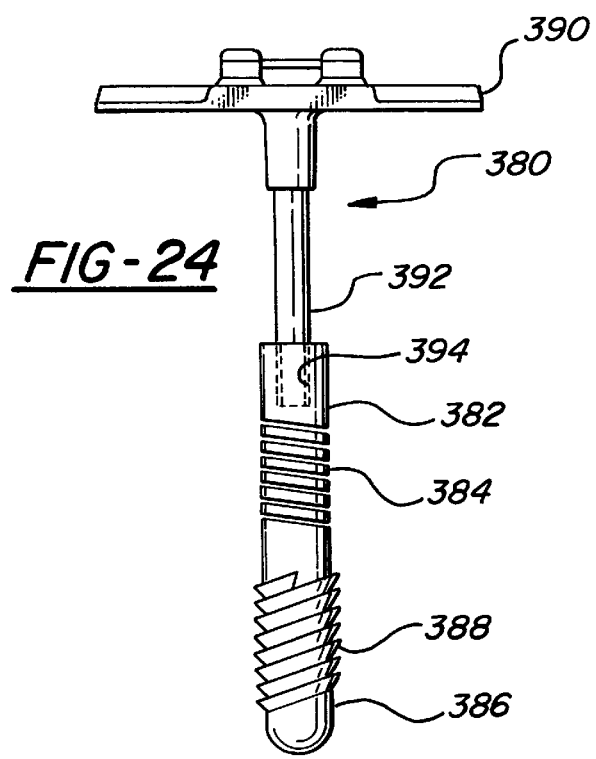
FIG. 24 is an elevational view illustrating another version of the second embodiment of the present invention.
Figure 25:
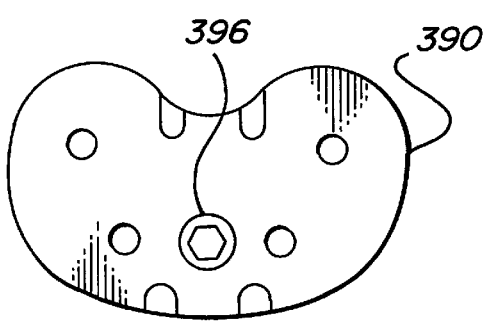
FIG. 25 is a top view of the version of apparatus shown in FIG. 24.

Referring now to FIGS. 24 and 25 there is shown another version of bone assembly according to the present invention at 380. The bone assembly 380 includes a main body 382, a compliant section 384 and an anchor body 386, formed in a cylindrical arrangement. The anchor body 386 includes threads 388 for engaging the walls of a cavity within a bone, such as the first intramedullary cavity 204 or a cavity created within a bone. In the version shown in FIGS. 24 and 25, the bone assembly 380 is fitted with a tibial tray 390 that is attached to the main body 382 via a post 392 threaded into the threaded bore 394 located within the main body 382. The tibial tray 390 is operable to engage a prepared tibial surface, another tibial surface or a device attached to a tibia. The bone assembly 380 is thus operable to be engaged within a bone cavity via threads 388 so that any attachment, such as the tibial tray 390 may engage the bone at another surface. It will be appreciated that a tibial tray attachment is only one of several arrangements for this version of the present invention.

The compliant extension 384 can be expanded to a desired condition of expansion after the bone assembly 380 is threaded into a bone cavity by any suitable device. One possible device utilizes the threaded bore 394 to pull the main body 382 in a proximal direction using a tibial surface, another bone surface or a device mounted upon a tibial surface or other bone surface as a reference. In another arrangement, shown in FIG. 25, a hexagonal headed screw 396 is recessed within the tibial tray 390 and can be dethreaded with a suitable tool within a stem of the tibial tray 390. Alternatively, the compliant section 384 can be expanded to a desired condition of expansion prior to implantation, using a preloading rod or other preloading device, as previously described. Alternatively, a traction rod can extend from the compliant section 384 and the traction applied to the traction rod with counterforce applied against the tibial tray 390 expands the compliant section 384 to the desired amount. A locking member is then advanced on the traction rod down against the tibial tray 390, preventing re-contraction of the compliant section 384. The traction is then removed from the traction rod, leaving residual expansion of the compliant section 384 and a state of compression at the interface between the tibial tray 390 and the bone.

Figure 26:
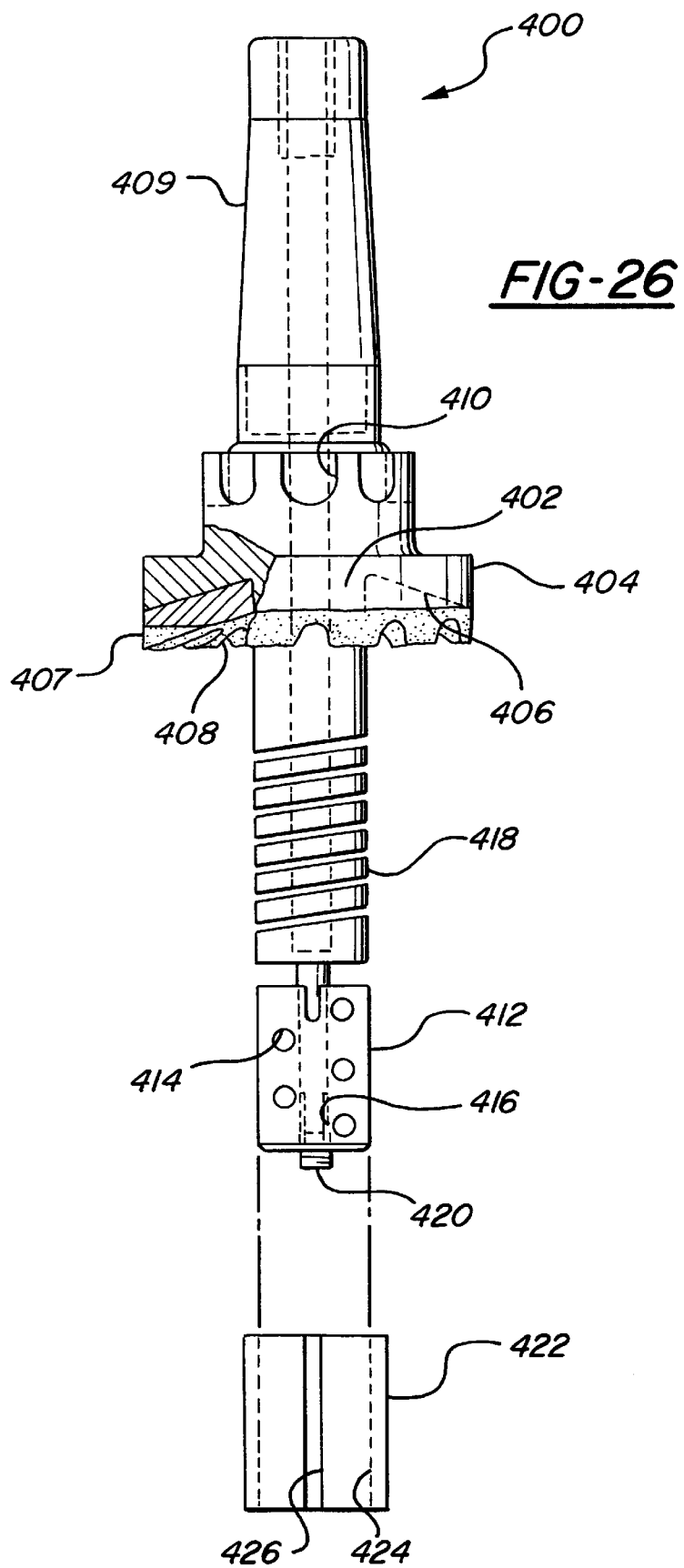
FIG. 26 is an elevational view in partial breakaway illustrating another version of the second embodiment of bone attachment assembly of the present invention, in modular form.

Referring now to FIG. 26, there is shown another version of the second embodiment of the present invention. In this version, the bone attachment assembly, designated as 400, is in a modular form. The bone attachment assembly 400 includes a main body 402 having a shoulder portion 404 and an interface surface 406. A porous coating 407 is disposed upon the interface surface 406 in this version of the invention. The porous coating 407 is preferably a titanium particle plasma spray. Alternatively, other suitable porous coating materials may be used, including sintered cobalt beads and titanium fibermesh pads. The porous coating 407 is operable to promote bone ingrowth and/or ongrowth and is operable to enhance the engagement of the main body 402 with the bone interface. The porous coating 407 is shown to be formed with a plurality of ridges 408. These ridges 408 further enhance the engagement of the main body 402 with the bone interface, and increase the surface area for bone ingrowth and/or ongrowth. It will be appreciated that any of the versions of the device discussed herein may include a porous coating of this type. An extension 409 is attached to the main body 402, which is generally of the same configuration as previously described. In this version, the main body 402 includes a plurality of recesses 410 in similar fashion to the recesses 215 described in connection with FIGS. 15–17. Here, however, there are eight recesses 410 disposed about the main body 402 approximately 45° apart.

The bone attachment assembly 400 includes an anchor body 412 having a plurality of apertures 414 for securing the anchor body 412 within a bone cavity. The anchor body 412 is shown here to be a separate component that includes a threaded recess 416 for connection to the remainder of the assembly. The bone attachment assembly 400 includes a compliant section 418 in the form of a helical spring, in similar fashion as before. The compliant section 418 includes a threaded post 420 that is operable for connection to the anchor body 412 by being threaded into the threaded recess 416.

In this version, the bone attachment assembly is implanted by first inserting the anchor body 412 into the bone cavity, such as the first intramedullary bone cavity 204 described in connection with FIG. 15. The anchor body 412 is substantially secured in place by any of the methods described herein. The milling of the end of the bone is then performed, using the anchor body 412 to help establish an axis. The compliant section 418 is expanded with an expansion bolt. The assembly is then inserted into the bone cavity. The main body 402 is then rotated so as to thread the threaded post 420 into the threaded recess 416. As this is done, the engagement of the interface surface 406 with the bone interface surface eventually occurs, and further advancement of the threaded post 420 into the threaded recess 416 is not possible. This occurs before the shoulder of the threaded post abuts against the anchor body 412. The expansion bolt is then removed.

As shown in FIG. 26, a sizing ring 422 is operable to be disposed upon the bone attachment assembly 400. The sizing ring 422 is operable to effectively enlarge the diameter of at least a portion of the bone attachment assembly 400 that is inserted within a bone cavity. The sizing ring 422 also assists in centering the bone attachment assembly 400 with respect to the bone. The sizing ring 422 is therefore disposed upon the bone attachment assembly 400 in situations where at least a portion of the bone assembly 400 is smaller than at least a portion of the bone cavity in which it is to be disposed. The sizing ring 422 is preferably a cylindrical tube of internal diameter that is approximately equal to the external diameter of the anchor body 412 and the compliant section 418. The sizing ring 422 is operable to be slid upon the anchor body 412 and the compliant section 418 up to the point where it contacts the interface surface 406. Alternatively, the sizing ring 422 may be disposed upon any suitable section of the bone attachment assembly 400.

The sizing ring 422 includes an inner surface 424 that preferably engages snugly against the external surface of the elongated bar making up the anchor body 412 and the compliant section 418. The sizing ring 422 may preferably include a split 426 at which the sizing ring 422 may be slightly enlarged to facilitate its positioning upon the bone attachment assembly 400. The sizing ring 422 is preferably made of a titanium alloy, such as Ti-6Al-4V, although it will be appreciated that any suitable material may be used. It will also be appreciated that the sizing ring 422 may take on other suitable shapes and sizes as may be desirable for assisting in centering the bone attachment assembly 400 with respect to the bone, and in enlarging the effective size of the bone attachment assembly 400.

It will be appreciated that in this procedure, the order of steps may be altered without departing from the invention. For example, in the procedure described above in connection with FIG. 26, the proximal bone surface may not be milled until after the insertion of the anchor body 412 within the bone cavity. In addition, the anchor body 412 may be secured within the cavity by threading it directly into the cavity, in similar manner as that described in connection with FIG. 24.

In the method of this embodiment of the present invention, a bone is prepared by cutting or other removal or shaping of bone surfaces through methods well known to those skilled in the art. A suitable bone cavity is prepared along the natural intramedullary canal of the bone or through any other region of bone through methods well known to those skilled in the art. One or more suitable engagement surfaces are prepared for the engagement of the components of the device discussed herein, including any special geometries, by methods well known to those skilled in the art. Where desired, suitable fixation bores are created through the bone, also by methods well known to those skilled in the art.

The compliant section of any version of the bone attachment assembly described above is converted to a preselected condition of expansion. Where it is desirable that this be done prior to implantation, means for loading the compliant section to a condition of expansion, such as the preloading rods and other devices discussed herein, are used to expand the compliant section. This may include expanding the compliant section to the degree where the apertures through an anchor body will be aligned with fixation bores disposed within the bone or with another suitable reference. This preferably includes inserting the rod described above into the bore of the bone attachment assembly and engaging the rod with a portion of the bone attachment assembly, such as threading a threaded portion of the rod into a threaded portion of the bore, thereby expanding the compliant section to a preloaded condition. The bone attachment assembly is then implanted within a cavity within the bone. Once the preloaded bone attachment assembly has been inserted within the bone, the means for anchoring the bone attachment assembly is secured in a substantially secured relation and the rod is disengaged from the bone attachment assembly and removed Where expansion of the compliant section is performed following insertion within a bone cavity, the insertion process is performed by threading or otherwise, and the expansion of the compliant section is then performed by utilizing a suitable expansion device. The bone attachment assembly is then secured in place, with the compliant section in expansion.

It will be appreciated that several of the components described herein can be made in an integral fashion, or may be formed as separate components that can be threaded or otherwise attached. Additionally, the compliant section in each version can be formed in different configurations and having different perforations of predefined configurations to achieve certain desired results in terms of load, spring rate and deflection. It will be appreciated that the principle of compliant fixation set forth herein can be used in conjunction with any type of bone by varying the sizes and configurations of the components without deviating from the invention. Thus, it will be appreciated that the present invention may be used with any large bone of the body, including a femur, tibia, bones about the elbow and ankle, a finger, a toe or at other suitable anatomical locations where an anchoring device with compliant fixation is desired. In addition, it should be recognized that this principle of compliant fixation may also be useful in other applications, such as in a cabling technique.

Referring now to FIGS. 27–31, there is shown a first version of a third embodiment of the present invention. In this embodiment, the bone attachment assembly is provided with a sleeve for inhibiting tilting of the compliant section of the assembly in a non-axial direction. This sleeve is preferably an integral extension connected to the main body of the assembly. The bone attachment assembly also includes several additional variations of anchor bodies, which may be secured within a remaining bone portion in different ways. In addition, in this embodiment, the compliant section is provided as an integral extension upon the anchor body.

FIG. 27 is an exploded elevational view of a bone attachment assembly, generally at 500, in a modular form. The bone attachment assembly 500 includes a main body 502 having a shoulder portion 504 and an interface surface 506, in similar manner as before. The interface surface 506 is shown to be disposed at an angle relative to the longitudinal axis of the main body 502. When the interface surface 506 is so angled relative to the longitudinal axis of the assembly, the main body has the ability to become radially constrained against a remaining bone portion upon installation. It will be appreciated, however, that the interface surface 506 may be disposed at any other suitable angle, including a right angle, relative to the longitudinal axis of the main body 502. The main body 502 includes a cylindrically shaped sleeve 508 disposed as an integral extension upon the lower surface of the main body 502. The sleeve 508 includes a recess 510 of a generally cylindrical shape that is preferably operable for containing a substantial portion, or the entire portion, of the compliant section discussed below. The inside diameter of the recess 510 is preferably slightly greater than the outer diameter of the compliant section and anchor which it is designed to contain, so that the main body 502 and compliant section are free to move in an axial direction relative to one another, but are substantially constrained in their abilities to move or angulate in non-axial directions relative to one another. The recess 510 is preferably only slightly greater in inside diameter than the outer diameter of the compliant section. It is believed that reducing non-axial deformation of the compliant section of the assembly enhances performance by reducing movements and tilting of the main body relative to the remaining bone portion after implantation.

The main body 502 and the sleeve 508 are shown in FIG. 27 to be coaxial, although this need not be the case. It will therefore be appreciated that any bone attachment assembly set forth herein may utilize a non-coaxial configuration between the main body and sleeve. In such arrangements, it will be appreciated that the interface surface, such as 506, may be disposed at any suitable angle relative to the sleeve, such as 508.

The main body 502 also includes an extension 512 for attachment to any suitable device, including an artificial limb, an intercalary segment or an opposing main body of an opposing bone attachment assembly or an articular component. The extension 512 is shown to be of a truncated conical configuration, although it will be appreciated that any suitable connection shape may also be used. An aperture 514 is disposed through the main body 502 and extension 512, opening into the recess 510 at its far end. A recess 516 is also provided at the near end of the extension 512, opening into the aperture 514. Together, the recess 510, the aperture 514 and the recess 516 provide a specially-configured continuously hollow interior designed to accept the insertion of, and interact with, those additional portions of the assembly that allow the assembly to apply interface pre-stress and exhibit compliance in the implanted condition. It will be appreciated that the various configurations and versions of this embodiment of the present invention will allow this general principle to be adjusted to any configuration necessary to accomplish this desired result. Accordingly, it will also be appreciated that various combinations of assembly components may be used to accomplish the compliant result in this embodiment, and that different components may be substituted throughout to achieve this end. For example, in one version discussed below, the recess 510, aperture 514 and recess 516 cooperate to allow the insertion of a traction rod integrally formed with a compliant section of the assembly. A nut or other engagement device inserted within the recess 516 operates to secure the traction rod relative to the main body of the assembly. It will be appreciated that the axis of the sleeve 508 may be the same as or may differ from the axis of the extension 512.

The bone attachment assembly 500 also includes an anchor body 520. The anchor body 520 is shown to be formed at its far end in the shape of a hemisphere for ease of insertion. It will be appreciated that other suitable shapes which forward any advantage, including ease of insertion and other advantages, may also be used. It is believed that hemispherical and tapered configurations generally tend to be more easily inserted into an enlarged intramedullary cavity of a remaining bone portion. The version of anchor body shown at 520 in FIG. 27 is the type secured within an enlarged intramedullary cavity of a remaining bone portion by cross-pinning the anchor body 520 through the cortex of the remaining bone portion. Apertures 522 are provided for the passage of appropriate pins or other fixation devices through the anchor body 520. Although four such apertures 522 are shown in FIG. 27, disposed about the perimeter of the hemisphere, it will be appreciated that any suitable number and configuration of apertures 522 may also be used. In addition, the apertures 522 may be angled, tapered, threaded or otherwise configured as appropriate to utilize any advantage of any chosen method of fixation through the bone cortex, including screws and expanding mechanisms.

The bone attachment assembly 500 also includes a compliant section 524. In this embodiment, the compliant section 524 is provided as an integral extension connected to the anchor body 520. This arrangement is believed to have advantages both in facilitating installation and in performance. In keeping with the modular nature of this assembly, however, it will be appreciated that the anchor body 520 may be releasably attachable to and from the compliant section 524, such as through the use of a cooperating threaded portion and recess. The compliant section 524 is preferably of a cylindrical shape and sized for insertion within the recess 510. The compliant section 524 may preferably be formed as a double helical structure, although it will be appreciated that other configurations, including a single helical structure and other spring-type structures, perforations, indentations and other configurations may also be acceptable. Also, the compliant section 524 may consist of a solid bar, if the material and dimensions of that bar render it sufficiently elastic such that it is more compliant than the section of bone between the interface and the anchor. Determination of the most preferred configuration for the compliant section 524 may depend on such factors as spring constant, degree of unwinding upon application of force (during installation loading or during subsequent operation), deflection of helices away from the axis with axial loading, and the relative radial positions of start and finish of the helices, or left-hand versus right-hand direction of helices, and choice of material. The compliant section 524 may preferably be formed by electron discharge machining or water jet cutting a cylindrical piece of material integrally formed with the anchor body 520. Other suitable means may also be used. An aperture 526 is shown to run through the compliant section 524 and the anchor body 520, which is believed to facilitate manufacture and function of the compliant section 524, as well as reduce the overall weight of the assembly.

The bone attachment assembly 500 also includes means for applying traction to the compliant section 524, which may also be described as means for converting the compliant section 524 to a condition of expansion. A traction rod 528 is disposed integrally as an extension from the near portion of the compliant section 524. Engagement of the traction rod 528 in a suitable manner relative to the main body 502 converts the compliant section 524 to a desired condition of expansion during installation. In this version of this embodiment, the traction rod 528 is of a generally cylindrical configuration, and of a size suitable for insertion within the aperture 514, and extending into the recess 516. The traction rod 528 includes a threaded portion 530 at its near end for engagement with a suitable engagement device, such as a nut, described below. Since the traction rod communicates force to and from the compliant section 524, engagement of the traction rod 528 relative to the main body (which engages the remaining bone portion) acts to apply traction to the compliant section 524, and converts the compliant section 524 to a preselected condition of expansion. The amount of traction or expansion which may be applied to the compliant section 524 is intended to be limited to a preselected range or guided to a specific amount by certain configurations of the assembly and instrumentation design. As such, the compliant section 524 may be expanded to and beyond the elastic limit but not exceeding static ultimate stress. In a condition of expansion, the compliant section 524 has the ability to react elasticly to deflections in opposing axial directions, which is believed to be the desired reaction for a compliant implant device. It will be appreciated that the compliant section 524 may be adjusted in its degree of expansion as may be desirable to achieve the desired applied interface pre-stress forces in the implanted condition. This may be accomplished through several portions of the assembly, including the sizing of certain components and the selected degree of engagement between such components such as the traction rod 528 and the nut described below, and through the planned milling of bone which defines the distance between the step (described below) located upon the anchor body 520 and the interface surface of the remaining bone portion.

The anchor body 520 and compliant section 524 include several design features intended to facilitate working with the bone attachment assembly 500 in installation, adjustment and alignment. A step 532 is provided along the near surface of the compliant section 524. This step 532 acts as a limit for expansion of the compliant section 524 against the interior end of the recess 510. A step 534 is also provided about the near perimeter of the anchor body 520. The step 534 provides an engagement surface for insertion tools and the like during installation of the anchor body 520. The anchor body 520 also includes a notch 536 or other geometric irregularity that is specifically designed for engagement by an insertion and alignment tool to assure proper rotational alignment of the anchor body 520 during the creation of bony apertures used in the cross-pinning of the anchor body 520 within a remaining bone portion into which the anchor body 520 is inserted. It will be appreciated that other appropriate design features may be incorporated for facilitating installation, adjustment and alignment.

FIG. 28 is a top view illustrating the main body 502, including the shoulder portion 504, extension 512, aperture 514 and recess 516. In this figure, the shoulder portion 504 is shown to be of a generally elliptical configuration. It will be appreciated that any other suitable configuration for the shoulder portion 504 may also be used, including a circular configuration. It will also be appreciated that any of the components shown herein may suitably be manufactured in a non-coaxial configuration between the main body 502 and the sleeve 508. The sleeve 508 may also be off-center relative to the shoulder portion 504, regardless of the circular, elliptical or other configuration of the shoulder portion 504. FIG. 29 is an elevational side view of the anchor body 520, compliant section 524, and traction rod 528, shown in FIG. 27. In this side view, 90° removed from the side view shown in FIG. 27, the configuration of the apertures 522 through the anchor body 520 can be seen.

FIG. 30 is a partial cross-sectional view of the bone attachment assembly 500 in partially assembled form. In this illustration, the traction rod 528 is shown to be inserted within the aperture 514. The compliant section 524 is also shown to be inserted within the recess 510. Once the anchor body 520 is secured within a remaining bone portion such as by cross-pinning, and the end of the remaining bone portion is optionally milled as desired, the bone attachment assembly 500 is assembled to the form shown in FIG. 30. In this form, traction can be applied to the traction rod 528 at the threaded portion 530 in order to apply traction to the compliant section 524 and convert the compliant section 524 to a desired condition of expansion.

FIG. 31 illustrates this version of bone attachment assembly 500 in assembled form and installed within a proximal femur, prior to converting the compliant section 524 to a degree of expansion. Specifically, the bone attachment assembly 500 is shown to be inserted within a prepared cavity 538 of a remaining bone portion 540. The prepared cavity 538 is preferably formed by reaming with a standard cylindrical reamer or any of the reamers set forth herein, although it will be realized that any suitable method may be used. The remaining bone portion 540 may be any human or animal bone, such as a human femur. Pins 542 are inserted through the cortex of the remaining bone portion 540 and through the apertures 522 in the anchor body 520. It will be appreciated, however, that screws or any other suitable engagement devices may also be used. A nut or other engagement device (not shown) may be subsequently threaded upon or may otherwise engage the threaded portion 530 of the traction rod 528 within the recess 516, against the interior end surface of the recess 516, as means for engaging the traction rod 528. In this arrangement, it can be seen that the forces applied to the compliant section 524 in opposing directions by virtue of the pins 542 securing the anchor body 520 to the cortex of the remaining bone portion 540, combined with the subsequent engagement of a nut upon the threaded portion 530 and against the interior end surface of the recess 516, will cause the compliant section 524 to be expanded and maintained in this condition. Thus, it can be seen that the design of the overall recess structure of the assembly allows for this communication of force to take place. The degree to which the compliant section 524 is expanded is based on how far the nut is threaded upon the threaded portion 530, limited by the engagement of the step 532 with the interior end surface of the recess 510.

The bone attachment assembly 500 may preferably be made of Ti-6Al-4V alloy, 17–4 PH stainless steel, Co—Cr—Mo alloy, 316 LVM stainless steel or any other suitable material. Certain components described herein may purposefully be made of a different material from other components where advantageous. Further, it will be appreciated that in any version of this embodiment, one or more of the various components may be altered in its size, shape and/or connectivity. Certain components of the bone attachment assembly of the present invention may be formed in a separate connecting fashion, rather than in an integrally formed fashion. For example, the threaded rod 528 may be a separately-formed component, attachable by threading or otherwise to the compliant section 524. Also, the nut and threaded portion 530 may be replaced by any suitable engagement features that maintain the principle of maintaining the compliant section 524 in a desired degree of expansion through the application of opposing forces from opposing ends of the assembly (such as by securing the anchor body 522 with respect to the bone cortex and by securing the threaded rod 528 with respect to the main body 502). Additional examples of the variations possible for the bone attachment assembly of the present invention are discussed below. It will be appreciated that as a general matter, many characteristics of the components described with respect to any of the embodiments herein may be combined, adjusted, substituted and modified to create many different combinations of assemblies suitable for achieving the desired compliant fixation.

FIGS. 32 and 33 disclose a second version of the third embodiment of the present invention. Specifically, FIG. 32 shows a bone attachment assembly generally at 600, which includes a main body 602, as before. In this version, however, the main body 602 is of a somewhat different configuration than the main body 502 described in FIGS. 27, 28, 30 and 31. The main body 602 includes a shoulder portion 604 with an inclined interface surface 602 that is angled relative to the longitudinal axis of the assembly. The shoulder portion 604 is configured in this version to have a near surface at approximately a right angle to the longitudinal axis of the assembly. As before, the shoulder portion 604 may take on any suitable shape, such as a circular shape or an elliptical shape, when viewed from above. The main body 602 also includes a cylindrically shaped sleeve 608 for reducing non-axial deformation of the compliant section discussed below when the bone attachment assembly 600 is in an assembled condition. A cylindrically shaped recess 610 extends through the sleeve 608 as before. In this version, however, the recess 610 also extends through the main body 602 and through a portion of the conically shaped extension 612 connected to the upper portion of the main body 602. Thus, in this configuration, the recess 610 is able to accommodate insertion of a much longer portion of compliant section, if desired. As before, the extension 612 is operable for connection to any suitable appliance.

The bone attachment assembly 600 also includes an aperture 614 that is operable for allowing the passage of a traction rod in similar manner as before. A recess 616 is located within the near portion of the extension 612, which opens into the aperture 614 in similar manner as before. The recess 616 again allows the insertion of means for engaging the traction rod in similar manner as before. In this arrangement, the recess 616 also includes a threaded portion 618 for facilitating a connection to any suitable external appliance.

FIG. 32 also shows an anchor body 620 that is formed in an elongated cylindrical configuration. The anchor body 620 includes apertures 622 in a staggered configuration for cross-pinning of the anchor body 620 within a remaining bone portion. A compliant section 624 is integrally formed with the anchor body 620 and may be formed in a single helix, double helix, or any other suitable compliant configuration, as discussed previously. In this arrangement, the anchor body 620 and the compliant section 624 can be configured to have substantially similar outer diameters. Alternatively, the outer diameter of the anchor body 620 may also be greater than the outer diameter of the compliant section 624. A traction rod 628 is integrally formed upon the near end of the compliant section 624, and contains a threaded portion 630 in a similar manner as before.

This configuration of bone attachment assembly also includes certain configurations intended to enhance the insertion and operability of the device. A step 632 is provided at the near end of the compliant section 624 as a stop against the near surface of the recess 610 when the bone attachment assembly 600 is in an assembled condition. Thus, the step 632 acts as a means for limiting the expansion of the compliant section 624. A recess 634 is also provided to allow for the insertion of a sleeve, discussed below, surrounding the upper portion of the anchor body 620, as a buffer between the anchor body 620 and the sleeve wall defined by the recess 610.

FIG. 33 shows the bone attachment assembly 600 in an assembled condition and disposed within an enlarged intramedullary cavity 638 of a remaining bone portion 640. In the installed configuration shown in FIG. 33, the anchor body 620 is substantially secured within the intramedullary cavity 638 through the use of pins 642 extending through the cortices of the remaining bone portion 640 and through the apertures 622 in the anchor body 620. The compliant section 624 is in an expanded condition through the engagement of a nut 644 upon the threaded portion 630 of the traction rod 628 and engagement of the nut 644 against the interior base surface of the recess 616. A sleeve 646 is disposed within the recess 634 for reducing contact between the compliant section 624 and the cylindrically shaped wall defining the recess 610. The sleeve 646 may be made of any suitable material, such as a polymer material or bioresorbable material. It may also extend over the length of the compliant section 624. An intercalary segment 648 is also shown to be disposed upon the extension 612. It will be appreciated that the intercalary segment may be any suitable appliance.

FIGS. 34–36 are three elevational views illustrating three sizes of a threaded anchor body which is an alternate to the cross-pinned versions of anchor body shown at 520 and 620. The threaded anchor bodies 700, 720 and 740 are each shown to be of a generally tapered configuration and include tapered helical cutting threads 702, 722 and 742. The threaded anchor bodies 700, 720 and 740 may also be of a generally cylindrical configuration. The tapered helical cutting threads 702, 722 and 742 each include a plurality of notches 704, 724 and 744 which are disposed longitudinally across the helical threads, thereby giving them a cutting character. Accordingly, the threaded anchor bodies 700, 720 and 740 are self-tapping anchor bodies that can be directly threaded into an enlarged intramedullary cavity or otherwise prepared cavity of a remaining bone portion and secured in place without the cross-pinning used in previous versions of this embodiment. Each threaded anchor body is shown to be integrally formed with a compliant section 706, 726 and 746. In similar manner as before, however, in keeping with the modular nature of the assembly, it will be appreciated that any of the threaded anchor bodies may be releasably attached to a compliant section, such as through the use of a cooperating threaded insertion portion and recess. Any of the compliant sections may be formed as a single helix, a double helix, or other suitable configuration. Also as before, the compliant sections 706, 726 and 746 are preferably formed by electron discharge machining or water jet cutting.

In this arrangement of threaded anchor bodies, the compliant sections 706, 726 and 746 each include a threaded recess 708, 728 and 748 for accepting a threaded screw of the type described in connection with FIG. 38. Apertures 710, 730 and 750 extend through the threaded anchor bodies 700, 720 and 740 as well as through the compliant sections 706, 726 and 746, in similar manner as before.

This configuration of anchor body also includes certain configured surfaces to facilitate insertion, adjustment and securing of the threaded anchor bodies 700, 720 and 740. A hexagonal engagement surface is provided on each threaded anchor body at 712, 732 and 752 to provide transmission of insertion torque. Alternatively, slots or tabs of any suitable configuration or other means may also be used as engagement surfaces. This surface is suitable for engagement by a correspondingly shaped hexagonal insertion tool that can be used to rotatably thread any of the anchor bodies into a secure position within an enlarged intramedullary cavity. Each threaded anchor body may also be provided with a step, at 714, 734 and 754 to provide an abutment surface for engagement of a suitable insertion tool.

FIG. 37 is a bottom perspective view illustrating the geometry of the tapered helical cutting threads 702 disposed upon the threaded anchor body 700. It will be appreciated that this configuration is applicable to any sized threaded anchor body 700, 720 or 740, and that the tapered helical cutting threads 702 are representative of any of the tapered helical cutting threads 702, 722 or 742. The tapered helical cutting threads 702 are shown to be separated by specifically shaped notches or cutting flutes 704 that are designed to provide a cutting action for the arrangement. Between any two cutting flutes, the major radius R of the thread preferably remains constant. This is shown by the radii indicia at $R_1, R_2, R_3$ and $R_4$. A jump in radius $\Delta R$ occurs for the cutting threads 702 at each cutting flute 704. As such, as one follows a thread from the trailing margin of a cutting flute to the leading margin of the next cutting flute, the major radius of the thread does not change. As one crosses the cutting flute, there is a discrete increase in the thread radius. This change in thread radius need not be constant, however, among the various levels of the cutting threads 702. For a conical shaped anchor body, however, the change in thread radius $\Delta R$ among cutting flutes 704 would generally be constant. It will be appreciated that this principle applies to a single, double or other multiple cutting flute arrangement and that any suitable shape for the notches or flutes 704 may be used.

FIG. 38 is an elevational view illustrating a threaded screw 760 that is suitable for being threadably inserted into the threaded recess 708, 728 or 748 in any of the threaded anchor bodies 700, 720 or 740. The threaded screw 760 includes a head 762 having a recess 764 that is shown in a configuration suitable for engagement of a flat-bladed screw driver. It will be appreciated, however, that any suitable engagement means may also be used, including a hexagonal internal recess (such as for engagement of a hex key wrench) or a hexagonal external surface for engagement of a conventional-type socket wrench or similar tool. The threaded screw 760 also includes a threaded portion 766 at its opposing end. The threaded portion 766 is suitable for direct engagement within the threaded recesses 708, 728 or 748 of any of the threaded anchor bodies shown in FIGS. 34–36. An optional, preferably hemispherical, washer 768 is also provided below the head 762 for engagement within a suitable recess that is formed as part of a main body, extension portion or other suitable attachment forming part of the bone attachment assembly of the present invention. The washer 768 may be threaded upon the threaded screw 760.

FIG. 39 is a partial cross-sectional view illustrating a third version of the third embodiment of the present invention. In this version, a threaded anchor body of the type shown in FIG. 35 is used in combination with a main body of the type shown in FIG. 27, with a threaded screw of the type shown in FIG. 38 included as a means for applying traction to the compliant section or means for expanding the compliant section to a preselected degree of expansion.

A bone attachment assembly is provided generally at 800 and includes a main body 802. The main body 802 includes a shoulder portion 804 having an interface surface 806, in similar manner as before. A sleeve 808 is disposed upon the main body 802, and includes a recess 810. An extension 812, of a generally conical configuration, is disposed upon the near end of the main body 802. An aperture 814 is disposed within the main body 802, which opens into the recess 810. A recess 816 is provided at the near end of the extension 812, which opens into the aperture 814, such that the recess 816, the aperture 814, and the recess 810 provide a passageway for insertion of a threaded screw 860.

A threaded anchor body 820 is shown to be inserted within an enlarged intramedullary cavity 838 of a remaining bone portion 840. The threaded anchor body includes tapered helical cutting threads 822 having notches 824, in similar manner as before. The bone attachment assembly 800 also includes a compliant section 826, integrally formed with the near end of the threaded anchor body 820. A threaded recess 828 is provided at the near end of the compliant section 826 so that means for engaging the compliant section with respect to the main body, in the form of a threaded screw 860, may be threadably inserted. An aperture 830 is disposed through the compliant section 826 and the threaded anchor body 820, also as before. Engagement surfaces 832, of different geometry than the hexagonal engagement surface previously described, and step 834 are also provided for engagement of this section of the bone attachment assembly 800 by a suitable tool.

Means for engaging the compliant section 826 with the main body 802 is provided in the form of a threaded screw 860 that is inserted through the aperture 814 and is threaded by its threaded portion 866 into the threaded recess 828. The threaded screw 860 may preferably be of the type shown at 760 in connection with FIG. 39. As the threaded screw 860 is advanced into the threaded recess 828, engagement of the head 862 against the interior end surface of the recess 816 causes expansion of the compliant section 826, since the threaded anchor body 820 is retained in place within the remaining bone portion by the tapered helical cutting threads 822. A recess 864 is provided upon the head 862 to facilitate tightening of the threaded screw 860, as previously described. It will be appreciated that the threaded screw 760 shown in FIG. 39 may also be used in conjunction with a recess, such as that shown at 828 in FIG. 40, as a means for expansion of the compliant section in any other embodiment described herein, such as in FIGS. 27 and 29–31.

FIG. 40 illustrates a fourth version of the third embodiment of the present invention, wherein a standard tibial tray is used as an alternative attachment for any of the main bodies previously described. The tibial tray 870 includes a recess 872 that is operable for accepting the insertion of a threaded screw 874, which may be a modified version of the screw 760 shown in FIG. 38. Of course, it will be appreciated that the length of the screw 862 may be adjusted to suit the particular need. The screw 862 may even be of excessive length so as to project into the compliant section and even into the anchor body 820. The tibial tray 870 is shown to be attached to an integral anchor body 820 and compliant section 826 from the discussion accompanying FIG. 39, although it will be appreciated that any form of anchor body and compliant section, integrally formed or not, may also be used. In addition, the compliant section 826 may also be attached directly to the tibial tray 870.

The method of using this embodiment of the present invention is discussed with reference to FIGS. 41–47. It will be appreciated, however, that in similar manner as before, different combinations of method steps are intended to be capable of substitution for use with any of the assembly embodiments described herein. In this embodiment of the method of the present invention, an intramedullary cavity or other cavity of a remaining bone portion is suitably prepared for containing any of the anchor bodies described herein. In the case of the cross-secured version of anchor body 520 or 620 described in connection with FIGS. 27–33, a standard cylindrical reamer (not shown) well known to those skilled in the art may be used. In those arrangements, however, where one of the threaded anchor bodies 700, 720 or 740 illustrated in FIGS. 34–36 are used, specially-shaped reamers shown in FIGS. 41–43 are preferably used. These reamers may also be used as an alternative with the cross-secured version of anchor body 520 or 620. Three reamers of different sizes are shown in FIGS. 41–43 at 900, 910 and 920. Each reamer includes a shaft 902, 912 and 922 having graduated scale markings 904, 914 and 924 for identifying depth of insertion of the reamer. The shaft 902, 912 or 922 may be attached to any power drill or other suitable powered instrument, or may alternatively be powered by hand. A cutting end 906, 916 and 926 located at the far end of each reamer includes specially-shaped cutting surfaces 908, 918 and 928 that are designed to form a portion of an intramedullary cavity of a remaining bone portion to compliment the shapes of the threaded anchor bodies shown in FIGS. 34–36. The cutting surface 928 is shown to have a maximum diameter d representing the maximum diameter to which a cavity will be reamed using the instrument. Preferably, the diameter d is greater than or equal to the maximum thread diameter of the anchor body to be inserted within the aperture being reamed. This principle applies for all reamer sizes.

Figures 44, 45:
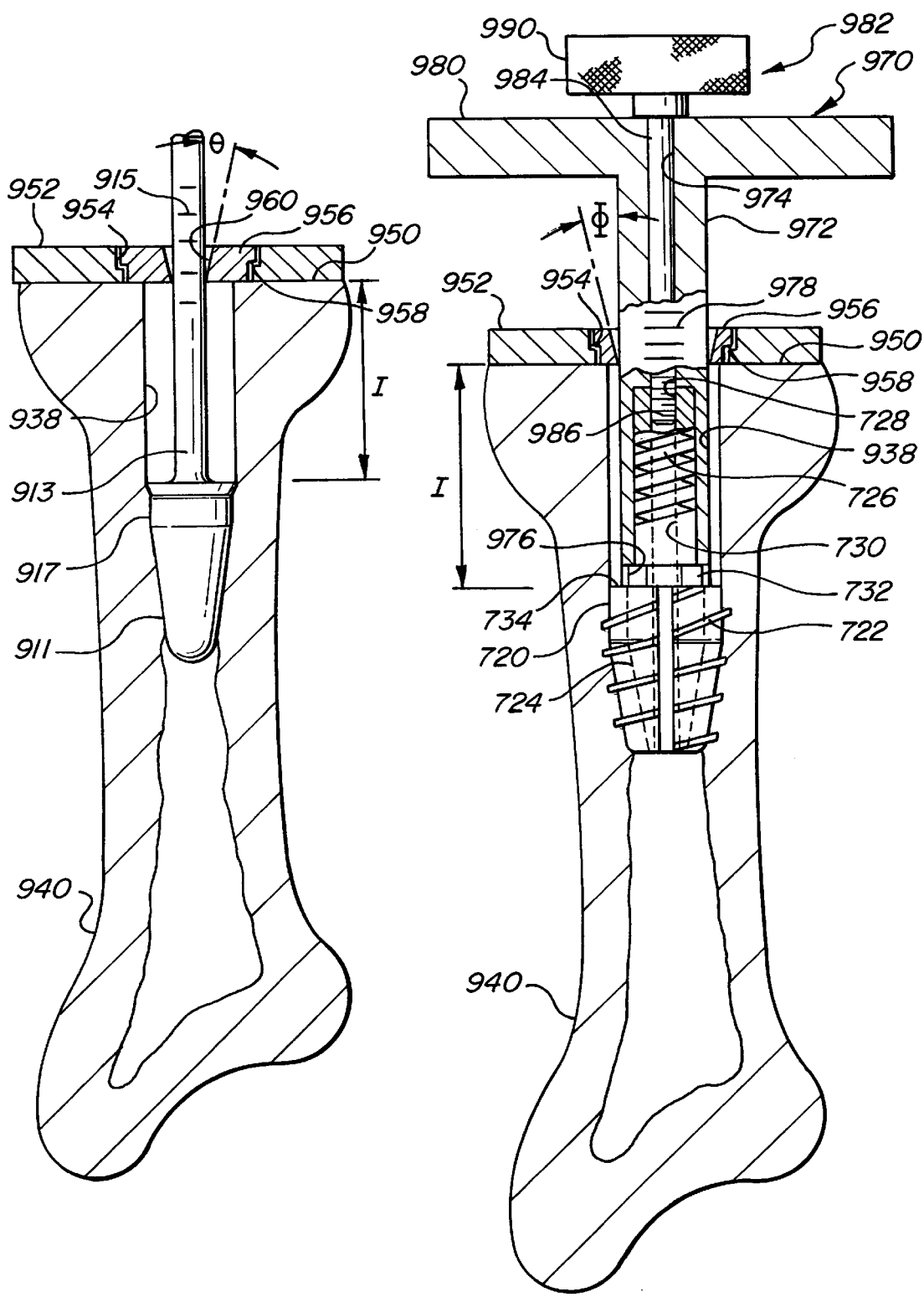
FIG. 44 is a partial cross-sectional view illustrating the use of a tapered reamer for enlarging the intramedullary canal of a remaining bone portion.
FIG. 45 is a partial cross-sectional view illustrating use of an anchor inserter and threaded rod assembly for accomplishing the insertion of a threaded anchor within a prepared intramedullary cavity of a remaining bone portion.

FIG. 44 shows a suitable method for preparing an intramedullary cavity 938 of a remaining bone portion 940, for insertion of a threaded anchor body of the type shown in FIGS. 34–36. In the steps of this method of the present invention, the bone within which the bone attachment assembly of the present invention is to be inserted is first cut as desired. Cutting of the bone may involve the removal of diseased or defective bone portions, as appropriate. The bone is cut through methods well known to those skilled in the art, preferably at a 90° angle relative to the longitudinal axis of the bone. It will be appreciated, however, that this angle of cutting may also be adjusted for several factors, including but not limited to the configuration of the natural intramedullary cavity of the bone, certain adjustments in the configuration of the main body, anchor body or compliant section of the bone attachment assembly (including non-coaxial configurations), or for other considerations. The remaining bone portion 940 may be a tibia or any other suitable bone portion. The resulting bone abutment surface 950 may optionally be subsequently milled through any suitable method discussed herein or other methods known to those skilled in the art.

The surgeon determines the desired width and depth for enlargement of the natural intramedullary cavity of the remaining bone portion 940 by first determining the size and configuration of the components of the bone attachment assembly to be used. This is accomplished through selecting, from those different trial sizes available, the appropriately sized and configured main body, tibial tray or other assembly component. Once the surgeon determines the amount of space to be taken by the chosen assembly component, a trial base plate 952 is selected for performing a reaming operation upon the natural intramedullary cavity of the remaining bone portion 940. The trial base plate 952 is chosen to be of a size and configuration that will correspond to the selected attachment to be placed upon the bone abutment surface 950 when the bone attachment assembly as a whole is installed. The trial base plate 952 is temporarily pinned into a substantially stationary position for the reaming and plug insertion process, preferably with several 1/8" pins that pass through the trial base plate 952 and into the bone, through methods well known to those skilled in the art. The trial base plate 952 includes a notched aperture 954. A centering disc 956, of a substantially circular configuration, includes a notched perimeter surface 958 that is intended to substantially correspond to the notched aperture 954 of the trial base plate 952. In this arrangement, insertion of the centering disc 956 within the notched aperture 954 of the trial base plate 952 provides a removable and replaceable means for guiding a reaming operation. The centering disc 956 includes an angled aperture 960 that is of a generally conical configuration and is offset from a vertical configuration by an angle θ relative to the longitudinal axis of the natural intramedullary cavity of the remaining bone portion 940. A possible selection for the value of the angle θ is 5°, although it will be appreciated that other suitable angle values may be used. The minimum internal diameter for the centering disc 956 is located at its far end, as the angled aperture 960 is angled away from the longitudinal axis in the near direction. The angled aperture 960 is configured in this way to allow for some freedom of angular movement during a reaming operation, while keeping the location of intersection between the reamer longitudinal axis and the trial base plate substantially unchanged. As such, the minimum internal diameter for the angled aperture 960 is located upon the far surface of the centering disc 956, or at the preferred level of said intersection. It will be appreciated that different diameters for the angled aperture 960 may be substituted by merely substituting differently sized centering discs 956. Thus, in this arrangement, a variety of freedom of movement ranges may be achieved through the use of differently sized centering discs 956.

In the reaming operation shown in FIG. 44, multiple graduated sized reamers, such as the ones shown in FIGS. 41–43, are used in a progressive manner to enlarge the natural intramedullary cavity of the remaining bone portion 940, until the cortical bone is reached that is suitable for securing an anchor body of the types used in the present invention. The reamers are used, preferably from smallest to largest desired size, by placing the desired centering disc 956 upon the shaft of the particular reamer selected, and then reaming either using a powered device or by hand. In the illustration shown in FIG. 44, an intermediate-sized reamer 911 is used as a variation of the configuration shown for the intermediate reamer 910. This reamer 911 has a cylindrical portion 917 corresponding to the design of the anchor body being used. The reamer 911 is shown to have a centering disc 956 placed upon its shaft 912 and positioned upon the notched aperture 954 of the trial base plate 952. Powering of the reamer 911 either by hand or with power assisted equipment results in the formation of an enlarged intramedullary cavity, designated by the numeral 938 in FIG. 44. This operation is repeated through a progressively larger series of reamers until the desired size for the enlarged intramedullary cavity 938 is achieved. The graduated scale markings 915 are used to identify the desired insertion depth I for the reamer 911.

FIG. 45 illustrates the installation of a threaded anchor body of the type shown in connection with FIGS. 34–36. For purposes of illustration, the anchor body 720 from FIG. 35 is shown in the FIG. 45 illustration. In this step of the method of the present invention, once the natural intramedullary cavity of the remaining bone portion 940 has been sufficiently enlarged, a threaded anchor body, such as that shown at 720, is inserted into the enlarged intramedullary cavity 938. With a trial base plate 952 in place upon the bone abutment surface 950, a suitably sized centering disc 956 is placed upon the cannulated shaft 972 of an anchor inserter 970.

The anchor inserter 970 is a device used for securing the threaded anchor body 720 in place within the enlarged intramedullary cavity 938 by rotatably threading it into place so that the tapered helical cutting threads 722 become secured within the cortex of the bone at the desired distance from the bone abutment surface 950. The cannulated shaft 972 of the anchor inserter 970 includes an aperture 974 that is specially sized to a small diameter over the near portion of the cannulated shaft 972, while being sized to a larger diameter over the far portion of the cannulated shaft 972. The purpose for this configuration of the aperture 974 is to allow the cannulated shaft 972 to be inserted over the compliant section 726 of the threaded anchor body 720. A hexagonal recess 976 located at the far end of the aperture 974 is sized and configured to engage the hexagonal engagement surface 732 of the threaded anchor body 720. Rotation of the cannulated shaft 972 then accomplishes a rotating insertion of the threaded anchor body 720 within the enlarged intramedullary cavity 938. Graduated scale markings 978 may preferably be disposed upon the cannulated shaft 972 for determining the desired insertion depth I of the threaded anchor body 720 by this device. A handle 980 is provided as part of the anchor inserter 970 to assist in rotation of the cannulated shaft 972 by hand. Alternatively, it will be appreciated that other configurations may also be used to assist in this insertion.

A positioning rod 982 is also provided for helping to maintain the desired positioning and attitude of the threaded anchor body 720 during the insertion procedure. The positioning rod 982 can also be used for extraction. The positioning rod 982 includes a shaft 984 having a threaded portion 986 at its far end. In the operation of this device, the positioning rod 982 is engaged with the threaded recess 728 of the threaded anchor body 720 through the threaded portion 986. A knob 990 or other torque applying means is provided at the near end of the shaft 984 to facilitate gripping by hand. Preferably, the positioning rod 982 is threadably engaged to the threaded recess 728 so that the threaded anchor body 720 may be held in place during the rotation of the anchor inserter 970 that causes fixation of the threaded anchor body 720.

In the use of the centering disc 956 in this step of the method of the present invention, the centering disc 956 may or may not be the same size of centering disc 956 used in connection with FIG. 44. As can be seen in FIG. 45, the centering disc 956 has an angled aperture 960 displaced in similar manner as before at an angle φ relative to the longitudinal axis of the remaining bone portion. The angle of offset represented by φ may or may not be the same as the angle φ described in connection with FIG. 44 in the use of the reamer 911.

The depth of insertion I for the threaded anchor body 720 is determined from a reading of the graduated scale markings 915 along the shaft 913 of the reamer 911 during the reaming operation. The threaded anchor body 720 is then advanced in an amount corresponding to the depth I read originally from the reamer 911 during the reaming exercise and matching the depth markings 978 along the shaft 972 of the anchor inserter 970. Alternatively, it may be advanced a preselected number of turns after cortical engagement is noted. The threads 722 cut into the bone surface adjacent the enlarged intramedullary cavity 938 to a certain distance beyond the reamed distance, typically about 1 or 2 mm. The surgeon also notes the depth of the threaded anchor body 720 to determine the length of screw to apply to the compliant section 726 for expanding the compliant section 726 to the desired degree. The trial base plate 952 and centering disc 956 are then removed.

Referring again to FIG. 39, in the next step of the method of the present invention, the desired assembly component, such as the main body 802, a tibial tray such as that shown at 870 in FIG. 40, or other suitable assembly component is then placed upon the remaining bone portion 840. In the case where a tibial tray such as that shown at 870 in FIG. 40 is used, the tibial tray 870 is merely placed onto the end of the remaining bone portion above the compliant section 826. In the situation where a main body is used such as in FIG. 39, the main body 802 is positioned upon the remaining bone portion 840 such that the sleeve 808 is inserted within the enlarged intramedullary cavity 838 over the compliant section 826. A screw, such as that shown at 864 in FIG. 39, is then inserted through the aperture 814 so that the threaded portion 866 may be threadably inserted into the threaded recess 828. The threaded screw 860 is then advanced by a sufficient number of turns to expand the compliant section 826 to the desired amount.

FIG. 46 demonstrates the method of the present invention used for cross-securing, such as by cross-pinning, an anchor body of the types shown in connection with FIGS. 27–33, within an intramedullary cavity or other prepared cavity. In FIG. 46, however, this is illustrated as one possible variation in the configuration of the anchor body 520. Specifically, the anchor body 520 is provided with a chamfered flange 550 that both facilitates component assembly and provides limited contact area between the anchor body 520 and the anchor holder 1002, and allows small variations in the angle between the anchor body 520 and sleeve. Accordingly, the chamfered flange 550 will also provide limited contact area between the anchor body 520 and any sleeve disposed as an extension of any main body. It is believed that such freedom of angle is advantageous toward function of the assembly as a whole.

Discussion of the present method of the invention describes the steps used for creating apertures within the surrounding bone cortex, in an aligned relationship with the apertures 522 of the anchor body 520. It will be appreciated that similar steps may be undertaken to install the anchor body 620. The apertures created through the bone cortex are used to secure the anchor body 520 in a substantially secured relation by cross-securing, such as through cross-pinning, cross-screwing or the like. FIG. 46 shows an anchor body 520 with integral compliant section and integral traction rod 528 in relation to an enlarged intramedullary cavity 1038 of a remaining bone portion 1040. Once the components of the assembly have been inserted within the enlarged intramedullary cavity 1038, a preferably adjustable drill guide, designated generally at 1000, is used to prepare apertures within the bone cortex as described above. The drill guide 1000 includes an anchor holder 1002, a cross-bar 1004 and an adjustable drill jig 1006. The anchor holder 1002 includes a recess 1008 that is of a generally similar configuration to the sleeve 508 of the main body 502 previously described. As such, the anchor holder 1002 does serve the function of setting the depth and establishing the axis of the the anchor holder 1002 for accomplishing the cross-drilling function. A tab 1010 is provided at the far end of the anchor holder 1002, for engaging the notch 536 in the anchor body 520. The cross-bar 1004 and the drill jig 1006 can be aligned by the surgeon such that the apertures 1014 in the drill jig 1006 are in the proper location for guiding a drilling procedure within the bone cortex. A nut 1051 or other suitable engagement device is tightened upon the traction rod 528 to secure the anchor holder 1002 relative to the anchor body 520. A knob 1053 is used to tighten the drill jig 1006 in an aligned position relative to the anchor body 520. Rods (not shown) may be inserted through the apertures 1014 to facilitate and test the alignment of the jig 1006 both prior to drilling and following the drilling of any aperture in the bone cortex. Once the drill guide 1000 is aligned and tightened by the surgeon and inserted into the bone, a power drilling device of the type well-known to those skilled in the art is then inserted through the apertures 1014 and drilling is undertaken through the bone cortex of the remaining bone portion 1040, through the apertures 522 of the anchor body 520 and through the opposing side of the bone cortex. This operation is performed for all apertures 522 of the anchor body 520. when drilling is complete, pins are inserted through the apertures 1014 of the drill jig 1006. The pin length is selected by a measurement process. After the pins are placed, the nut 1051 or other engagement device is removed and the drill guide 1000, including the anchor holder 1002, is removed.

Once the anchor body 520 has been secured within the remaining bone portion 1040, a main body, tibial tray or other suitable attachment is placed upon the anchor body 520 and the compliant section 524, in similar manner as before. Once the above components are in place, a suitable engagement device such as a nut similar to that at 1051 used for securing the anchor holder 1002 during the drilling procedure, is applied to the threaded portion 530 of the traction rod 528. The nut is tightened a sufficient number of turns as determined by the surgeon for expanding the compliant section 524 to the desired degree.

FIG. 47 shows a tool for use in the optional milling of a bone abutment surface. More specifically, FIG. 47 shows a pilot member 1060 that fits over the compliant section 524 of the bone attachment assembly, in similar manner as before. The pilot member includes a recess 1062 so that the pilot member 1060 can be inserted over the compliant section 524 until it meets the step 534 forming a portion of the near surface of the anchor body 520. The anchor body 520 is also shown to include a different configuration, in the form of a spherically-shaped contact region 552 of radius r, that facilitates component assembly and provides a small angular freedom between it and any sleeve attached to any main body, in a different way than the chamfered flange 550 shown in FIG. 46. The pilot member 1060 includes a shaft 1064 designed to be fitted over the traction rod 528 integrally formed with the compliant section 524.

A milling device 1070 is shown to include a cutting end 1072 at a predetermined angle relative to the longitudinal axis of the remaining bone portion 1040 to be milled. This angle can be perpendicular to the longitudinal axis or at any suitable angle. The milling device 1070 also includes a recess 1074 shaped to fit over the shaft 1064 of the pilot member 1060. A shaft 1076 is also provided for attachment to a power drill or any other powered attachment suitable for rotating the milling device 1070 at a high speed. A set screw 1078 is also provided for tightening the milling device 1070 against the shaft 1064.

In operation, rotation of the milling device 1070 against an abutment surface 1050 of a remaining bone portion 1040 causes the cutting end 1072 to mill the abutment surface 1050 into a shape represented by the cutting end 1072. As shown in FIG. 47, operation of the milling device 1070 shapes the abutment surface 1050 to an angle in a direction corresponding to the angle represented by the cutting end 1072. Following this procedure, the milling device 1070 and pilot member 1060 are removed, and the remaining steps of the procedure for securing the bone attachment assembly components and for expanding the compliant section are followed in similar manner as previously described.

Yet another embodiment of the bone attachment assembly of the present invention is described in connection with FIGS. 48–51. Specifically, FIG. 48 shows one version of this embodiment of bone attachment assembly generally at 1100. The bone attachment assembly 1100 includes a main body 1102 having an articular portion 1104. In this configuration, the articular portion 1104 is of a generally convex cross-section so as to have a complimentary shaped interface surface 1106. As such, the interface surface 1106 is suitable for being applied directly upon a surface of a remaining bone portion, such as a proximal femur, that has been shaped through milling or other available methods to a generally convex configuration.

The bone attachment assembly 1100 also includes an anchor body 1120 having apertures 1122 for securing the anchor body 1120 by cross-pinning or cross-screwing in a similar manner as before. The anchor body 1120 also includes a compliant section 1124. An aperture 1126 is also shown to pass through the anchor body 1120 and compliant section 1124, in a similar manner as before. In this arrangement, the anchor body 1120, the compliant section 1124 and the main body 1102 are shown to be integrally formed. A threaded recess 1128 is provided at the far end of the aperture 1126 for threaded engagement of an expansion rod 1130, which is inserted from the far end into the aperture 1126, threaded with its threaded portion 1132 into an engagement with the threaded recess 1128, and removed from the far end of the assembly once the anchor body 1120 is secured in place. A knob 1134 may preferably be provided for facilitating insertion of the expansion rod 1130 and engagement with the threaded recess 1128. It will be appreciated that the knob 1134 may take on any suitable shape, such as a hexagonal shape, and may include a suitable means, such as a slot or recess, for engagement by a suitable tool, such as a screwdriver or a hex key wrench. FIG. 48 shows the knob 1134 to be provided with a hexagonal recess 1136, that is engaged by a torsion applying instrument such as hexagonal shaft 1138.

Alternatively, it will be appreciated that the expansion rod 1130 may also take the form of a long shaft having a threaded portion at mid-section, effectively combining the knob 1134 and hexagonal shaft 1138. In a similar manner as before, insertion of the expansion rod 1130 within the aperture 1126 and subsequent threading of the threaded portion 1132 with the threaded recess 1128 operates to expand the compliant section 1124 to a preselected condition of expansion. Since the expansion rod 1130, as well as the expansion rods shown in connection with FIGS. 49–51, expand each of the respective compliant sections from beneath, they must each be removed from beneath following the cross-pinning or other securing of the respective anchor bodies. This can be accomplished by a removal of the expansion rod through a continuation of the aperture into which the assembly is inserted, through a smaller diameter extension of this aperture or through a complimentary aperture formed from the end of the remaining bone portion opposite the main body.

Figure 51:
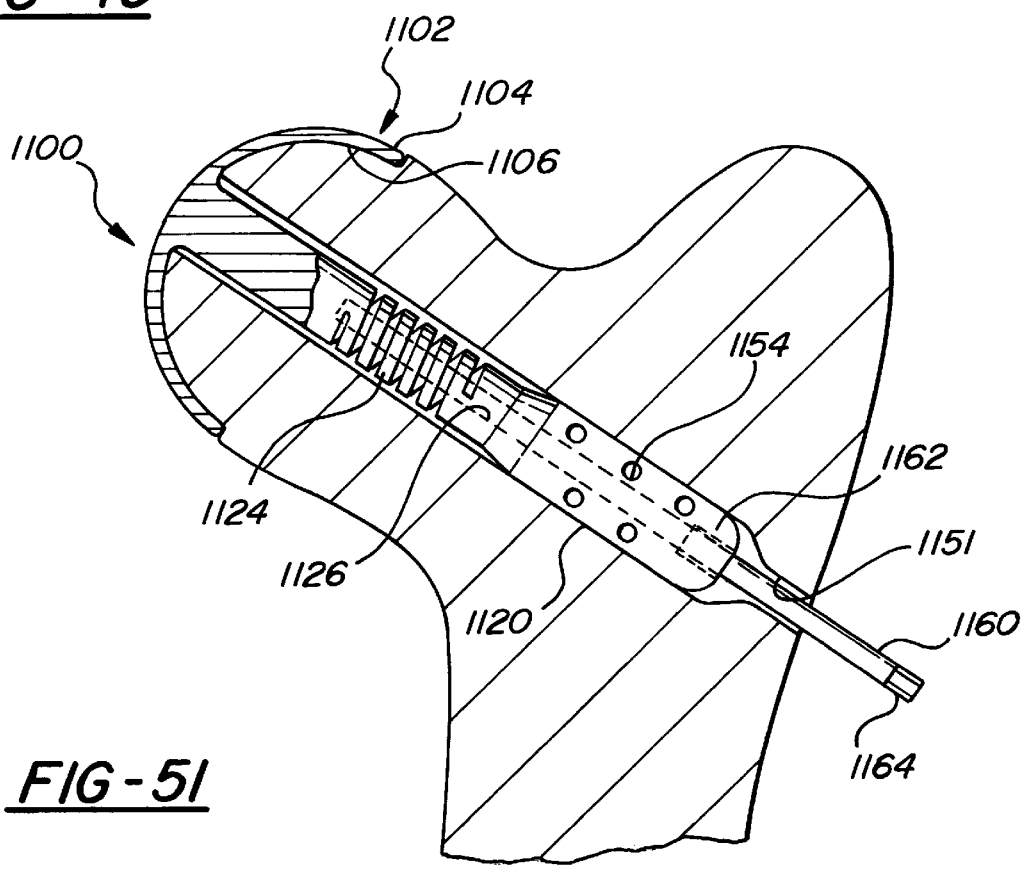
FIG. 51 shows the version of bone attachment assembly shown in FIG. 48, installed within a proximal femur.

FIG. 51 illustrates the installation of the version of bone attachment assembly shown in FIG. 48 within a human femur. The femoral head is first prepared to a spherical, cylindrical or conical configuration through methods well known to those skilled in the art. The configured femoral head may also include chamfered ends adjacent the spherical, cylindrical or conical configuration. A cavity 1150 is then reamed along the axis of the femoral neck by any of the methods described herein. An aperture 1151 is prepared through reaming, drilling or otherwise as an extension of the cavity 1150 passing through the cortex opposing the main body 1102. The aperture 1151 may be created from either cortex along the longitudinal axis of the cavity 1150. The aperture may preferably be of smaller diameter than the cavity 1150, and is preferably created after the cavity 1150 is created. Alternatively, the cavity 1150 may be prepared to extend entirely through the femur 1152.

An expansion rod is provided in FIG. 51 in an extended length form at 1160, with a centrally-located threaded portion 1162 for engaging the threaded recess 1128. The expansion rod 1160 may also preferably include an engagement configuration such as a hexagonally-shaped end 1164 for engagement by a wrench or other tool. The expansion rod 1160 is inserted into the aperture 1126 and threaded into the threaded recess 1128 to expand the compliant section 1124 to its intended force. The components of the bone attachment assembly 1100, including the anchor body 1120, the compliant section 1124 and main body 1102, including the articular portion 1104, are then inserted within the cavity 1150 and applied upon the prepared exterior surface of the femur. The expansion rod 1160 extends through the aperture 1151 and through the cortex proximate the anchor 1120. The aperture 1151 allows for any adjustment of expansion of the compliant section 1124 to be made. In the case where an extension rod of the type shown at 1130 in FIG. 48 is used, it can also be manipulated through the aperture 1151.

While the main body 1102, including the shoulder portion 1104, is held against the prepared femur surface, the anchor body 1120 is secured in place within the femur 1152 such as through the use of pins 1158, using similar method steps involving cross-drilling of apertures through the bone cortices and anchor body apertures 1122 and subsequent insertion of pins as previously described. Screws or other suitable fixation devices may also be used. Once the anchor body 1120 has been secured within the femur 1152, the expansion rod 1160 is removed from within the aperture 1126, through the aperture 1151 so as to allow the compliant section 1124 to exert force directly on the bony surfaces contacting the cross-pins and the main body 1102. Alternatively, it will be appreciated that a threaded traction rod may be integrally formed with the compliant section 1124 and expanded using a nut arrangement, in similar manner as before.

Figure 49:
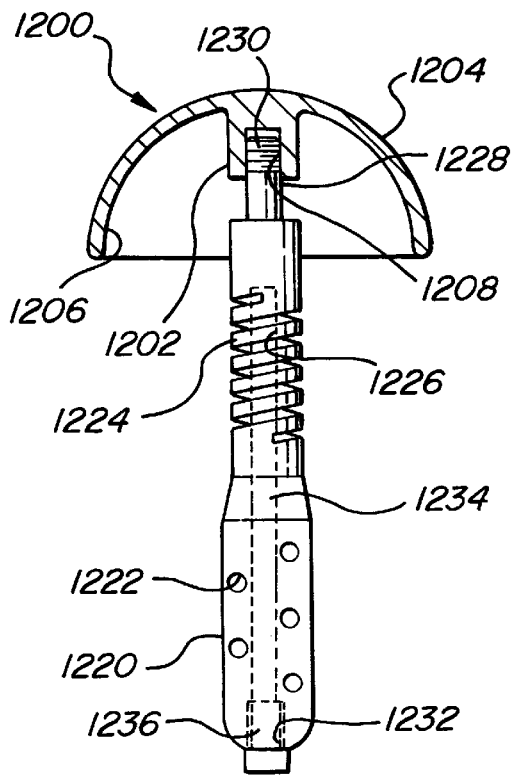
FIG. 49 is an alternative version of the bone attachment assembly shown in FIG. 48.

Another version of this embodiment of the present invention is shown in FIG. 49. Specifically, FIG. 49 illustrates a two-piece bone attachment assembly generally at 1200. The bone attachment assembly 1200 includes a main body 1202 having an articular portion 1204 which includes an interface surface 1206 in substantially the same shape as that described in connection with FIG. 48. In this arrangement, however, the main body 1202 contains a threaded recess 1208 for allowing assembly of the components of the bone attachment assembly 1200 during the surgical procedure.

The bone attachment assembly 1200 includes an anchor body 1220 having apertures 1222 suitable for cross-pinning, cross-screwing or the like. An integrally formed compliant section 1224 is also provided in a similar manner as before, and an aperture 1226 extends through the anchor body 1220 and the compliant section 1224, also in a similar manner as before. A connecting rod 1228 is provided at the near end of the compliant section 1224, and includes a threaded portion 1230 for engaging the threaded recess 1208 of the main body 1202. In a similar manner as before, the compliant section 1224 is expanded through the insertion of an expansion rod 1234 within the aperture 1226 and engaging the threaded portion 1236 of the expansion rod 1234 with a threaded recess 1232 located at the far end of the aperture 1226.

In the method involving this two-piece embodiment of the bone attachment assembly 1200, the femoral head is prepared substantially as before. A cavity and aperture are also prepared within the femur as before along the axis of the femoral neck. The expansion rod 1234 is inserted within the aperture 1226 and is threaded into the threaded recess 1232, thereby pre-expanding the compliant section 1224. The components are then inserted and placed upon to the remaining bone portion in similar manner as before. After the anchor body 1220 is affixed to the surrounding bone cortices with cross-pins or the like using the drill guide as before, the main body 1202 is then threaded onto the connecting rod 1228 snugly against the bone interface, and then the expansion rod 1234 is removed through the end of the bone aperture proximate the anchor 1220 so as to allow the compliant section 1224 to exert force directly on the bony surfaces contacting the cross-pins and the main body 1202. Alternatively, in this two-piece arrangement, the main body 1202 can be threadably attached to the compliant section 1224 before the cross-pinning has occurred and before the expansion rod is removed.

Figure 50:
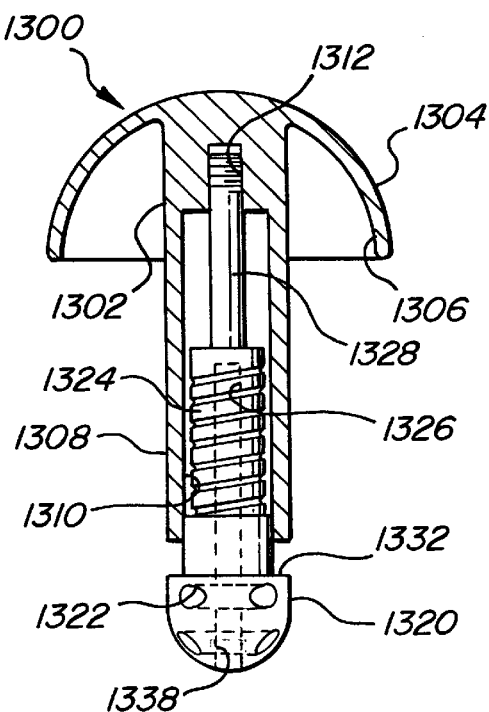
FIG. 50 is an alternative version of the bone attachment assembly shown in FIGS. 48 and 49, with a sleeve disposed for inhibiting non-axial relative displacement of the compliant section and main body.

FIG. 50 illustrates yet another version of this embodiment of the present invention, wherein a bone attachment assembly is provided generally at 1300. The bone attachment assembly 1300 includes a main body 1302 having an articular portion 1304 with an interface surface 1306 in similar configuration as before. In this arrangement, however, a cylindrically shaped sleeve 1308 is provided as an extension upon the main body 1302 in a similar manner as in previous embodiments. The sleeve 1308 is shown to include a recess 1310 with a threaded aperture 1312 at its near end. This arrangement also allows for separate assembly of these components during the surgical procedure.

The bone attachment assembly 1300 also includes an anchor body 1320, which is of a similar shape as the anchor body 520 shown in FIG. 31. The anchor body 1320 includes apertures 1322 and includes a step 1332 for engaging a suitable installation tool, and for acting as a stop against the far surface of the sleeve 1308 that regulates the amount of expansion for the compliant section 1324. The compliant section 1324 is integrally formed with the anchor body 1320 and an aperture 1326 extends through the anchor body 1320 and the compliant section 1324 in a similar manner as before. A connection rod 1328 is provided as an integral extension from the near end of the compliant section 1324. The connection rod 1328 includes a threaded portion 1330 suitable for engaging the threaded aperture 1312. The installation of this version of bone attachment assembly 1300 involves insertion of the compliant section 1324 into the recess 1310 and threading the threaded portion 1330 into the threaded aperture 1312. An expansion rod (not shown) having a threaded portion is used in similar manner as before for engaging a threaded recess 1338 located at the far end of the aperture 1326. Threading such an expansion rod into the aperture 1326 causes expansion of the compliant section 1324 in similar manner as before. In similar manner as before, the expansion rod is removed from within the aperture 1326 following installation and cross-pinning and application of the main body 1302, to activate the compliant force directly onto the bony surfaces adjacent the main body 1302 and the cross-pins.

Figure 52:
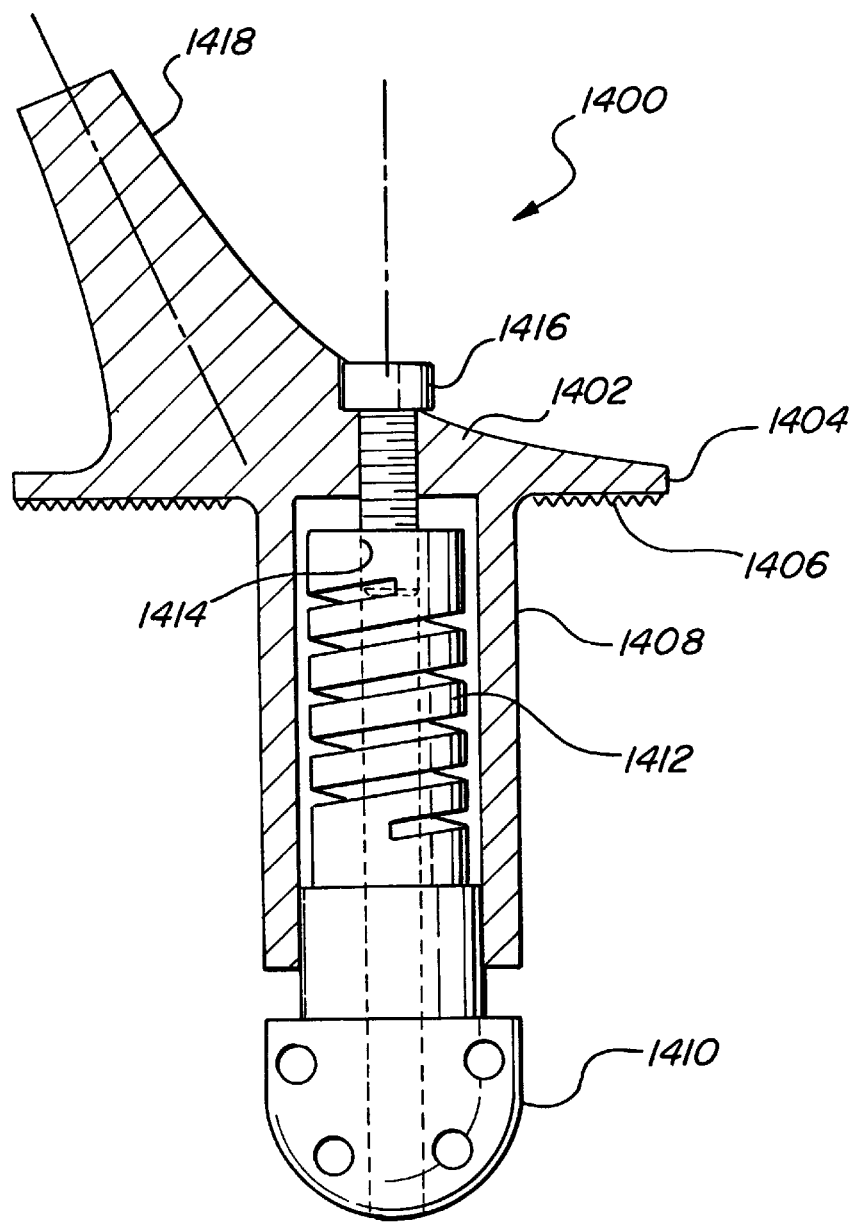
FIG. 52 is a partial cross-sectional view of a non-coaxial version of bone attachment assembly.

Yet another version of this embodiment of the present invention is shown in connection with FIG. 52. In this version, a bone attachment assembly is provided at 1400 in a non-coaxial configuration. The bone attachment assembly 1400 includes a main body 1402 having a shoulder portion 1404 and an interface surface surface 1406 with a bone ingrowth enhancing texture. A sleeve 1408 extends from the main body 1402 in similar manner as before. An anchor body 1410 and compliant section 1412 are integrally formed, with a threaded recess 1414 disposed at the near end of the compliant section 1412. A traction rod 1416 is also provided for expanding the compliant section 1412 relative to the main body 1402. In this arrangement, however, an extension 1418 is provided upon the main body 1402 in a non-coaxial relationship relative to the sleeve 1408. The traction rod 1416 is suitable for being inserted through the main body 1402 to the side of the extension 1418. This version is intended to demonstrate the ability of any component of the invention to be altered in its axial configuration relative to other components to achieve any advantage. In this arrangement, the non-coaxial configuration of the extension 1418 allows increased freedom of sleeve placement within the bone, thereby allowing positioning of a femoral head, for example, independent of the sleeve position. Furthermore, the orientation of the ingrowth interface may be independent from the axis of the extension 1418 and the sleeve 1408. It will be appreciated that the method steps applicable to this arrangement are substantially as previously described in connection with other similar configurations, and will not be repeated here.

It will be appreciated that any features of any of the embodiments and/or method steps set forth herein are intended to be substituted, shared and/or moved among the various versions and methods involving the assembly. As an example, it will be appreciated that any of the threaded anchor bodies described herein may be substituted for cross-pinned versions. Another contemplated arrangement involves the switching of positions of the compliant section and anchor, so that the anchor is threaded or cross-secured to the near side of the compliant section relative to the main body.

Yet another contemplated arrangement involves the ability of the compliant section to be switchable between extension and compression conditions, referring to the at-rest condition of the compliant section prior to engagement by a extension or compression rod, respectively. In the case of an extension compliant section, an extension rod expands or pulls the compliant section, such as by abutting a closed-ended aperture within the compliant section. In the case of a compression compliant section, a compression rod having a head or knob passes from the end opposite the main body through an aperture through the anchor body and compliant section to compress or push the already-expanded compliant section to a lesser degree of expansion. Force is applied to the compression version of compliant section by the knob or head against the end of the compliant section when the compression rod is threaded into a threaded recess in the main body. The present invention also contemplates the use of Belleville washers within a recess of a sleeve disposed integrally with or otherwise attached to the anchor body, as a substitute for the compliant section. The Bellevile washers are compressed by applying force to a plate or other device to the end washer such as by threading a compression rod with such a plate or other device through the washer section from a side opposite the main body. Thus, it will be appreciated that several methods are contemplated for the application of force in a compression or extension environment, using various compression and expansion implements, from either direction relative to the main body of the assembly.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A hip attachment assembly for attaching to a bone, said hip attachment assembly comprising:
   a hip component defining a main body, said hip component having an extension for mating with a ball, said hip component further including an inferior surface operable to engage a surface of the bone and a sleeve extending from said inferior surface, said hip component being formed from a single member;
   an anchor operable to anchor said bone attachment assembly to the bone, said anchor having a mating member; and
   a compliant portion operable to be expanded and contracted slidably disposed and contained within said sleeve;
   said sleeve being slidably engaged with said mating member to substantially inhibit non-axial deflection of said compliant member;
   said compliant portion being operably associated with said anchor and with said hip component.

2. The bone attachment assembly as set forth in claim 1, wherein said sleeve is integrally formed with said main body.

3. The bone attachment assembly as set forth in claim 1, wherein said anchor is capable of being secured within a first remaining bone portion by being cross-secured within a cavity of said first remaining bone portion by at least one engagement device disposed between said anchor and said first remaining bone portion.

4. The bone attachment assembly as set forth in claim 1, wherein at least a portion of said bone attachment assembly is operable for insertion within a cavity of said first remaining bone portion selected from the group consisting of an enlarged intermedullary cavity, a reamed bone cavity and a drilled bone cavity.

5. The bone attachment assembly as set forth in claim 1, wherein said compliant portion is sufficiently elastic such that it is more compliant than a section of said first remaining bone portion located between said anchor and said surface of said first remaining bone portion that engages said interface surface of said main body.

6. The bone attachment assembly as set forth in claim 1, wherein said interface surface of said main body includes at least one surface feature operable for inhibiting rotation of said main body with respect to said first remaining bone portion.

7. The bone attachment assembly as set forth in claim 1, wherein said main body is non-coaxial relative to said sleeve.

8. The bone attachment assembly as defined in claim 1 wherein said sleeve has a substantially cylindrical body with a cylindrical recess operable to receive said compliant portion.

9. The bone attachment assembly as defined in claim 1 wherein a traction rod axially extends from said compliant portion, said traction rod operable to be slidably received by said hip component to adjust a force applied to said compliant member.

10. The bone attachment assembly as defined in claim 1 wherein said anchor is operable to anchor said bone attachment assembly to the bone by use of at least one laterally extending cross pin passing through said anchor.

* * * * *